United States Patent
Chen et al.

(10) Patent No.: US 9,029,545 B2
(45) Date of Patent: May 12, 2015

(54) THIENOPYRIDINE NOX2 INHIBITORS

(75) Inventors: Deborah Chen, Commonwealth (SG); Kiew Ching Lee, Commonwealth (SG); Lamont Roscoe Terrell, King of Prussia, PA (US)

(73) Assignee: GlaxoSmithKline Intellectual Property Limited, Middlesex (GB)

( * ) Notice: Subject to any disclaimer, the term of this patent is extended or adjusted under 35 U.S.C. 154(b) by 245 days.

(21) Appl. No.: 13/516,252

(22) PCT Filed: Dec. 16, 2010

(86) PCT No.: PCT/US2010/060696
§ 371 (c)(1),
(2), (4) Date: Jun. 15, 2012

(87) PCT Pub. No.: WO2011/075559
PCT Pub. Date: Jun. 23, 2011

(65) Prior Publication Data
US 2012/0252805 A1    Oct. 4, 2012

Related U.S. Application Data

(60) Provisional application No. 61/287,798, filed on Dec. 18, 2009.

(51) Int. Cl.
*C07D 495/04* (2006.01)
*A61K 31/4365* (2006.01)

(52) U.S. Cl.
CPC .......... *C07D 495/04* (2013.01); *A61K 31/4365* (2013.01)

(58) Field of Classification Search
CPC .......................... C07D 513/04; A61K 31/4365
See application file for complete search history.

(56) References Cited

U.S. PATENT DOCUMENTS

2007/0082880 A1    4/2007    Boschelli et al.

FOREIGN PATENT DOCUMENTS

| EP | 1505068 | 2/2005 |
|----|---------|--------|
| EP | 1598354 | 11/2005 |

OTHER PUBLICATIONS

Montezano "Oxidative stress, Noxs, and hypertension: Experimental evidence and clinical controversies" Annals of Medicine, 2012; 44(Suppl 1): S2-S16.*
Julie, J.-P. "Transgenic mouse models of amyotrophic lateral sclerosis" Biochimica et Biophysica Acta 1762 (2006) 1013-1024.*

* cited by examiner

*Primary Examiner* — David K O Dell
(74) *Attorney, Agent, or Firm* — Haiyan Chen; William R. Majarian

(57) ABSTRACT

The present invention relates to novel NADPH oxidase II inhibitors and their use in the treatment of diseases mediated by the NADPH oxidase II enzyme.

10 Claims, No Drawings

THIENOPYRIDINE NOX2 INHIBITORS

This application is a 371 of International Application No. PCT/US2010/060696, filed 16 Dec. 2010, which claims the benefit of U.S. provisional application 61/287,798 filed 18 Dec. 2009.

The present invention relates to novel NADPH oxidase II inhibitors and their use in the treatment of diseases mediated by the NADPH oxidase II enzyme.

BACKGROUND OF THE INVENTION

Reactive oxygen species (ROS) are oxygen-derived small molecules including oxygen radicals such as superoxide, hydroxyl, peroxyl and alkoxyl. Through interactions with a variety of target molecules including small molecules as well as nucleic acids, proteins, lipids and carbohydrates, ROS play an important role in the regulation of diverse physiological processes. However, ROS can also irreversibly destroy or alter the function of target molecules. Excessive exposure to ROS induces oxidative stress and causes genetic mutations. ROS have been identified as a major contributor of cellular damage (Bedard & Krause (2007) *Physiol. Rev.* 87:245-313).

The NADPH oxidases (NOX) are transmembrane proteins that transport electrons across biological membranes to generate ROS from oxygen. Unlike other cellular elements such as mitochondria which generate ROS as a byproduct, the NOX enzymes generate ROS as their primary function. Seven members of the NOX family have been identified: NOX1 to NOX5, Duox1 and Duox2 (Bedard & Krause (2007) *Physiol. Rev.* 87:245-313).

NOX2, which was first identified in phagocytic cells and is often referred to as the phagocytic NOX, is also expressed in a variety of other cell types including neurons, cardiomyocytes, skeletal muscle myocytes, hepatocytes, endothelial cell and hematopoietic stem cells. Mutations in the human NOX2 gene cause chronic granulomatous disease (CGD), an immune disorder characterized by the inability of phagocytes to produce bacteria-destroying ROS. NOX2 deficient mice, which display pathological features similar to that of CGD patients, have been widely used as animal models (Sorce & Krause (2009) *Antioxid. Redox. Signal.* 11:2481-2504).

ROS overproduction by NOX2 has been implicated in the pathogenesis of a variety of central nervous system diseases including amyotrophic lateral sclerosis, Parkinson's disease, Alzheimer's disease, multiple sclerosis and Huntington's disease. Amyotrophic lateral sclerosis (ALS) is a progressive neurodegenerative disease that affects motor neurons. Although the cause of ALS is largely unknown, oxidative stress is believed to play a crucial role in the development of ALS. Studies have shown that NOX2 was activated in the spinal cord of ALS patients and mutant SOD1 transgenic mouse, which develops motor neuron degeneration comparable to those observed in ALS patients (Wu et al. (2006) *Proc. Natl. Acad. Sci. U.S.A.* 103:12132-12137). Recent studies in which mutant SOD1 mice were crossed with NOX2-deficient mice showed that NOX2 deficiency delayed neurodegeneration and increased lifespan of SOD1 mice, suggesting that NOX2 plays an important role in ALS pathogenesis (Marden et al. (2007) *J. Clin. Invest.* 117:2913-2919; Wu et al. (2006) *Proc. Natl. Acad. Sci. U.S.A.* 103:12132-12137). Parkinson's disease (PD) is a neurodegenerative disease characterized by progressive degeneration of dopaminergic neurons in the substantia nigra. Oxidative stress is believed to play an important role in the degeneration of dopaminergic neurons. Studies have shown that administration of lipopolysaccharide (LPS) resulted in the release of proinflammatory factors, the activation of NOX2 and the degeneration of dopaminergic neurons (Iravani et al. (2005) *Eur. J. Neurosci.* 22: 317-330; Qin et al. (2004) *J. Biol. Chem.* 279:1415-1421). In addition, NOX2 deficient mice were shown to be significantly protected against loss of dopaminergic neurons compared to wild-type mice (Qin et al. (2004) *J. Biol. Chem.* 279:1415-1421). The data thus suggest that NOX2 activation plays an important role in the loss of dopaminergic neurons in PD. NOX2 has also been implicated in the development of Alzheimer's disease (AD). Studies have shown that in the brain of AD patients, markers of oxidative stress increased with severity of the disease and NOX2 is activated (de la Monte & Wands (2006) *J. Alzheimers. Dis.* 9:167-181; Shimohama et al. (2000) *Biochem. Biophys. Res. Commun.* 273:5-9). In addition, studies in which the Tg2576 mice (an animal model of AD) were crossed with NOX2 deficient mice showed that oxidative stress and cerebrovascular dysfunction do not occur in Tg2576 mice deficient in NOX2 (Park et al. (2005) *J. Neurosci.* 25:1769-1777). There is also evidence that NOX2 is involved in the pathogenesis of multiple sclerosis (Sorce & Krause (2009) *Antioxid. Redox. Signal.* 11:2481-2504) and Huntington's disease (Stack et al. (2008) *Ann. N.Y. Acad. Sci.* 1147:79-92).

ROS overproduction by NOX2 has also been implicated in the pathogenesis of spinal cord injury (Kim et al. (2010) *Proc. Natl. Acad. Sci. U.S.A.* 107:14851-14856) and traumatic brain injury (Dohi et al. (2010) *J. Neuroinflamm.* 7:41).

In addition, ROS overproduction by NOX2 has been implicated in the pathogenesis of ocular diseases including diabetic retinopathy (Al-Shabrawey et al. (2008) *IOVS* 49:3231-3238; 3239-3244).

ROS overproduction by NOX2 has also been implicated in the pathogenesis of a number of cardiovascular diseases including hypertension, atherosclerosis, cardiac hypertrophy and cardiac fibrosis. Studies have shown renovascular hypertension was significantly reduced in the NOX2 deficient mice (Jung et al. (2004) *Circulation* 109: 1795-1801). Human atherosclerotic plaques have been found to express large amounts of NOX2 (Zhou et al. (2006) *Hypertension* 47:81-86). Studies have also shown that NOX2 plays an important role in angiotensin II-induced cardiac hypertrophy and cardiac fibrosis (Bendall et al. (2002) *Circulation* 105:293-296; Johar et al. (2006) *FASEB J.* 20:1546-1548). In addition, ROS production by NOX2 is also believed to be involved in the pathogenesis of stroke. Studies have shown that brain injury resulted from stroke induced in NOX2 deficient mice was significantly less than that in the wild-type mice (Walder et al. (1997) *Stroke* 28:2252-2258).

One approach to the treatment of those diseases associated with ROS overproduction by NOX2 is to search for compounds that inhibit NOX2.

SUMMARY OF THE INVENTION

The invention is directed to novel NOX2 inhibitors and their use in the treatment of diseases mediated by NOX2. Specifically, the invention is directed to compounds according to Formula I.

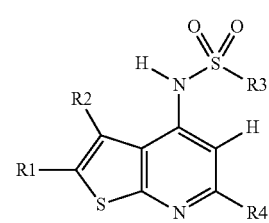

Formula I wherein R1, R2, R3 and R4 are defined below, and to pharmaceutically-acceptable salts thereof.

In another aspect, this invention provides for the use of the compounds of Formula I for the treatment of diseases mediated by NOX2. Examples of such diseases include neurodegenerative diseases such as amyotrophic lateral sclerosis, Parkinson's disease, Alzheimer's disease and Huntington's disease; neuroinflammatory diseases such as multiple sclerosis; cardiovascular diseases such as hypertension, atherosclerosis, cardiac hypertrophy, cardiac fibrosis and stroke; ocular diseases such as diabetic macular edema, diabetic retinopathy, age-related macular degeneration and glaucoma; spinal cord injury; and traumatic brain injury. In yet another aspect, the invention is directed to methods of treating such diseases.

DETAILED DESCRIPTION OF THE INVENTION

Terms and Definitions

In describing the invention, chemical elements are identified in accordance with the Periodic Table of the Elements.

"Alkoxy" refers to the group —O—R where R is alkyl having the specified number of member atoms. Examples of alkoxy include methoxy, ethoxy and propoxy.

"Alkyl" refers to a monovalent saturated hydrocarbon chain having the specified number of member atoms. For example, C1-C6 alkyl refers to an alkyl group having from 1 to 6 member atoms. Alkyl groups may be optionally substituted with one or more substituent as defined herein. Alkyl groups may be straight or branched.

Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Alkynyl" refers to an unsaturated hydrocarbon chain having the specified number of member atoms and having one or more carbon-carbon triple bond within the chain. For example, C2-C6 alkynyl refers to an alkynyl group having from 2 to 6 member atoms. In certain embodiments alkynyl groups have one carbon-carbon triple bond within the chain. In other embodiments, alkynyl groups have more than one carbon-carbon triple bond within the chain. For the sake of clarity, unsaturated hydrocarbon chains having one or more carbon-carbon triple bond within the chain and one or more carbon-carbon double bond within the chain are alkynyl groups. Alkynyl groups may be optionally substituted with one or more substituents as defined herein. Alkynyl groups may be straight or branched. Representative branched alkynyl groups have one, two or three branches. Alkynyl includes ethynyl, propynyl, butynyl, pentynyl and hexynyl.

"Cycloalkyl" refers to a saturated hydrocarbon ring having the specified number of member atoms. Cycloalkyl groups are monocyclic ring systems. For example, C3-C6 cycloalkyl refers to a cycloalkyl group having from 3 to 6 member atoms. Cycloalkyl groups may be optionally substituted with one or more substituent as defined herein. Cycloalkyl includes cyclopropyl, cyclobutyl, cyclopentyl, and cyclohexyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" refers to the time required for half of a quantity of a substance to be converted to another chemically distinct species in vitro or in vivo.

"Halo" refers to the halogen radicals fluoro, chloro, bromo, and iodo.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituent as defined herein. Heteroaryl groups are monocyclic ring systems or are fused or bridged bicyclic ring systems. Monocyclic heteroaryl rings have from 5 to 7 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, and naphthyridinyl.

"Heteroatom" refers to a nitrogen, sulphur, or oxygen atom.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituent as defined herein. Heterocycloalkyl groups are monocyclic ring systems or are fused, spiro, or bridged bicyclic ring systems. Monocyclic heterocycloalkyl rings have from 4 to 7 member atoms. Bicyclic heterocycloalkyl rings have from 7 to 11 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,4-dioxanyl, 1,3-oxathiolanyl, 1,3-oxathianyl, 1,3-dithianyl, azetidinyl, azabicylo[3.2.1]octyl, azabicylo[3.3.1]nonyl, azabicylo[4.3.0]nonyl, and oxabicylo[2.2.1]heptyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted, or the group may be substituted with one or more substituent as defined.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Suitable substituents are defined herein for each substituted or optionally substituted group.

Compounds

The present invention provides, in a first aspect, a compound of Formula I or a pharmaceutically acceptable salt thereof.

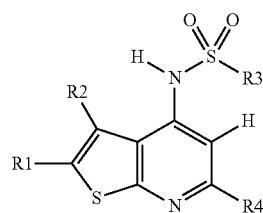

Formula I wherein:

R1 is selected from the group consisting of:
H, halo, CN, $(CH_2)_n NRaRa$, $C(O)NRaRa$, $C(O)ORb$, $NRbC(O)Rb$, $(CH_2)_m ORb$,
C1-C6 alkyl optionally substituted with heterocycloalkyl, heterocycloalkyl,
C1-C6 alkynyl optionally substituted with OH, C1-C3 alkoxy, NRaRa or heterocycloalkyl,
$(CH_2)_n Rc$ wherein Rc is optionally substituted with one or more substituents selected from the group consisting of C1-C3 alkoxy, C1-C3 alkyl, NRaRa and halo, and
$(CH_2)_n Rd$ wherein Rd is optionally substituted with one or more substituents selected from the group consisting of C1-C3 alkoxy, C1-C3 alkyl, NRaRa and halo;

R2 is selected from the group consisting of:
H, halo, CN, C(O)NRaRa,
C1-C6 alkyl,
heterocycloalkyl,
$(CH_2)_n Rc$ wherein Rc is optionally substituted with one or more substituents selected
from the group consisting of C1-C3 alkoxy, $(CH_2)_n NRaC(O)ORa$, $(CH_2)_n NRaRa$, halo,
C1-C4 alkyl optionally substituted with one to three F, and heterocycloalkyl optionally substituted with C(O)ORb, and
$(CH_2)_n Rd$ wherein Rd is optionally substituted with one or more substituents selected
from the group consisting of C1-C4 alkyl, C1-C3 alkoxy, halo, heterocycloalkyl and $(CH_2)_n NRaRa$;

R3 is selected from the group consisting of:
C1-C6 alkyl optionally substituted with Rc wherein Rc is optionally substituted with halo,
heterocycloalkyl optionally substituted with one or more substituents selected from the
group consisting of halo and C(O)ORb wherein Rb is optionally substituted with phenyl,
cycloalkyl,
Rc optionally substituted with one or more substituents selected from the group consisting of C1-C3 alkoxy, NRaRa, $NO_2$, halo, and C1-C4 alkyl optionally substituted
with one to three F, and
Rd optionally substituted with one or more substituents selected from the group consisting of C1-C4 alkyl, C1-C3 alkoxy, halo and phenyl;

R4 is H, C1-C6 alkyl, C1-C3 alkoxy, halo, CN or OH;
each Ra is H or C1-C6 alkyl or both Ra groups, independently in each instance, taken together with the nitrogen atom to which they are attached form a 5 to 7 membered heterocycloalkyl ring;
each Rb is H or C1-C6 alkyl;
each Rc is phenyl;
each Rd is heteroaryl;
each m is 1 or 2; and
each n is 0, 1, 2 or 3.

In one embodiment, R1 is H, CN, halo, C1-C6 alkyl optionally substituted with heterocycloalkyl, C1-C6 alkynyl optionally substituted with OH, NRaRa or heterocycloalkyl, C(O)NRaRa, C(O)ORb, NRbC(O)Rb, heterocycloalkyl, $(CH_2)_n$ Rc, or $(CH_2)_n Rd$, wherein said Rc is optionally substituted with C1-C3 alkoxy, said Rd is optionally substituted with one or more C1-C3 alkyl.

In another embodiment, R1 is C1-C3 alkyl or heteroaryl.
In yet another embodiment, R1 is pyrazolyl.

In one embodiment, R2 is H, halo, CN, C(O)NRaRa, C1-C6 alkyl, $(CH_2)_n Rc$ or $(CH_2)_n Rd$, wherein said Rc is optionally substituted with one or more substituents selected from the group consisting of C1-C3 alkoxy, $(CH_2)_n NRaC(O)ORa$, $(CH_2)_n NRaRa$, halo, C1-C4 alkyl optionally substituted with one to three F, and heterocycloalkyl optionally substituted with C(O)ORb, said Rd is optionally substituted with one or more substituents selected from the group consisting of C1-C4 alkyl, C1-C3 alkoxy, heterocycloalkyl and $(CH_2)_n NRaRa$.

In another embodiment, R2 is phenyl or pyridinyl optionally substituted with one or more substituents selected from the group consisting of C1-C3 alkoxy, halo, heterocycloalkyl and $(CH_2)_n NRaRa$.

In yet another embodiment, R2 is phenyl substituted with dimethylamino, pyrrolidinyl or morpholinyl.

In yet another embodiment, R2 is pyridinyl substituted with dimethylamino, pyrrolidinyl or morpholinyl.

In one embodiment, R3 is C1-C6 alkyl optionally substituted with Rc, cycloalkyl, heterocycloalkyl optionally substituted with halo or C(O)ORb, $(CH_2)_n Rc$, or $(CH_2)_n Rd$, wherein said Rb is optionally substituted with phenyl, said Rc is optionally substituted with one or more substituents selected from the group consisting of halo, $NO_2$, C1-C3 alkoxy and C1-C4 alkyl optionally substituted with one or more F, said Rd is optionally substituted with one or more substituents selected from the group consisting of C1-C4 alkyl, halo and phenyl.

In another embodiment, R3 is phenyl substituted with one or more halo or C1-C3 alkoxy.

In yet another embodiment, R3 is phenyl substituted with one or more Cl.

In one embodiment, R4 is H, C1-C6 alkyl, halo, CN or C1-C3 alkoxy.

In another embodiment, R4 is methyl.

In one embodiment, R1 is pyrazolyl, R2 is phenyl substituted with dimethylamino, pyrrolidinyl or morpholinyl, R3 is phenyl substituted with one or more Cl, and R4 is methyl.

In another embodiment, R1 is pyrazolyl, R2 is pyridinyl substituted with dimethylamino, pyrrolidinyl or morpholinyl, R3 is phenyl substituted with one or more Cl, and R4 is methyl.

The meaning of any functional group or substituent thereon at any one occurrence in Formula I, or any subformula thereof, is independent of its meaning, or any other functional group's or substituent's meaning, at any other occurrence, unless stated otherwise.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof.

The compounds of Formula I may exist as tautomers. Where tautomers exist, whether in equilibrium or predominately in one form, each tautomeric form and mixtures thereof are included in the present invention.

In certain embodiments, compounds according to Formula I may contain an acidic functional group. In certain other embodiments, compounds according to Formula I may contain a basic functional group. Thus, the skilled artisan will appreciate that pharmaceutically-acceptable salts of the compounds according to Formula I may be prepared. Indeed, in certain embodiments of the invention, pharmaceutically-acceptable salts of the compounds according to Formula I may be preferred over the respective free base or free acid because such salts may impart greater stability or solubility to the molecule thereby facilitating formulation into a dosage form. Accordingly, the invention is further directed to the use of pharmaceutically-acceptable salts of the compounds according to Formula I.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, the term "compounds of the invention" means both the compounds according to Formula I and the pharmaceutically-acceptable salts thereof. The term "a compound of the invention" also appears herein and refers to both a compound according to Formula I and its pharmaceutically-acceptable salts.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compounds of the invention have a pIC50 value of at least 4 in at least one of the suitable assays for determining the activity of a NOX2 inhibitor. Examples of such suitable assays include the fluorescence assay and the absorbance assay described herein.

Compound Preparation

The compounds according to Formula I are prepared using conventional organic syntheses. Suitable synthetic routes are depicted below in the following general reaction schemes. Starting materials and reagents depicted in the general reaction schemes below are commercially available or can be made from commercially available starting materials using methods known to those skilled in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Scheme 1 represents a general reaction scheme for preparing intermediates and certain compounds of Formula I. Amide 1.2 can be obtained by treatment of the corresponding acid chloride 1.1 with N,O-dimethylhydroxylamine in the presence of a base (such as pyridine) in a solvent (such as DCM) at temperatures between 0 and 50° C. Intermediate 1.4 can then be prepared by treatment of amide 1.2 with halide 1.3 in the presence of a metallating agent (such as n-BuLi) in a solvent (such as THF) at temperatures between −78 and 0° C.

Intermediate 1.4 can also be obtained by treatment of the corresponding aldehyde 1.5 with Grignard reagent 1.6 in a solvent (such as THF or Et$_2$O) at temperatures between 0 and 50° C. followed by oxidation under appropriate conditions (such as oxalyl chloride/DMSO/Et$_3$N/DCM).

Intermediate 1.7 can be obtained by treatment of the corresponding ketone 1.4 with malonitrile in hexamethyldisilazane and an acid (such as acetic acid) at temperatures between 20 and 80° C. Thiophene intermediate 1.8 can be obtained from 1.7 by treatment with sulfur in the presence of a base (such as NaHCO$_3$) in solvents (such as THF/water) at temperatures between 20 and 50° C.

Thienopyridine intermediate 1.10 can be obtained by treatment of intermediate 1.8 with methyl ketone 1.9 in the presence of a reagent (such as SnCl$_4$) in a solvent (such as toluene) at temperatures between 20 and 160° C.

Compound I(a) (wherein R1 is not halo and R2 is not halo) can be obtained by treatment of intermediate 1.10 with a sulfonyl chloride 1.11 in the presence of a base (such as LiHMDS, KOtBu or NaOtBu) in a solvent (such as THF, DMF) at temperatures between 20 and 50° C.

Where a protecting group (such as Cbz) is present in I(a) this can be deprotected under appropriate conditions (such as hydrogenation using a Pd/C catalyst) in a solvent (such as ethanol, methanol and acetic acid).

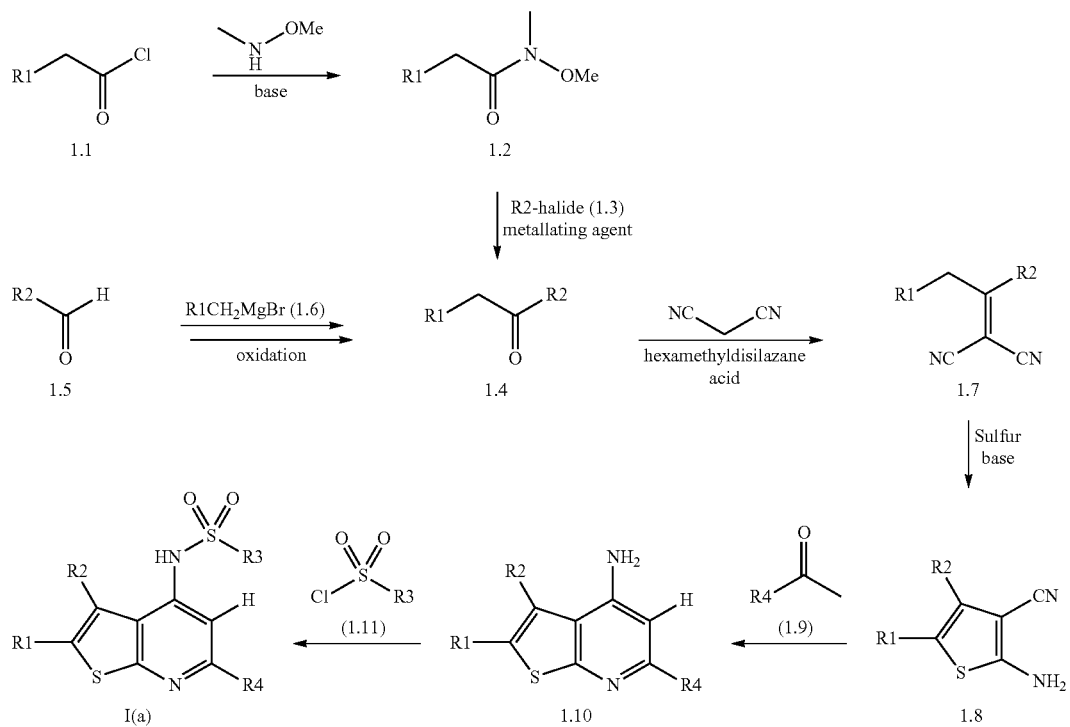

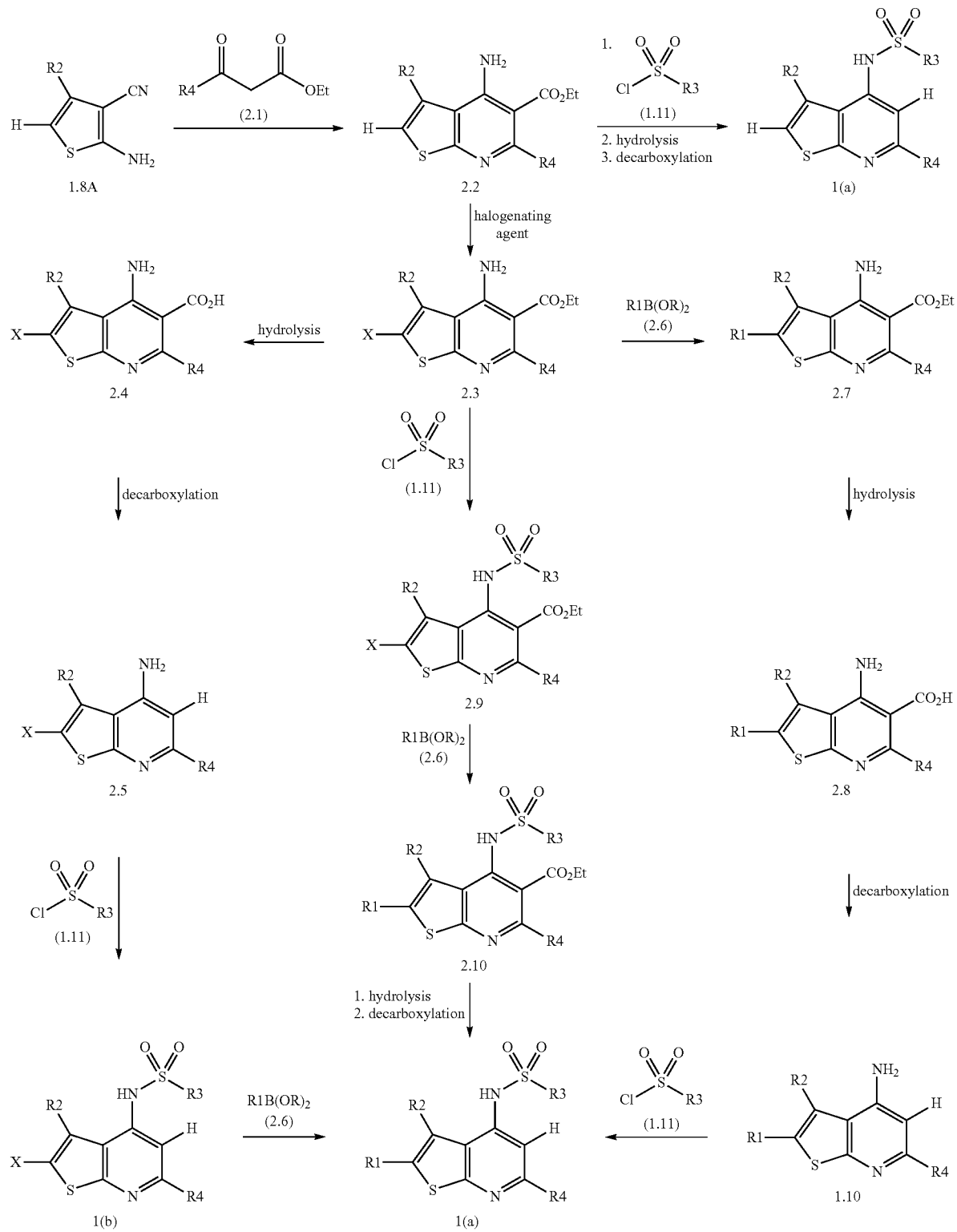

Scheme 2

Scheme 2 represents another general reaction scheme for preparing intermediates and certain compounds of Formula I. In Scheme 2, X is halo which represents R1. Thienopyridine intermediate 2.2 can be obtained by treatment of thiophene 1.8A with a ketoester 2.1 in the presence of a reagent (such as SnCl$_4$) in a solvent (such as toluene) at temperatures between 20 and 160° C. 2.2 can then be converted to 2.3 in the presence of an appropriate halogenating agent (such as N-bromosuccinimide) in a solvent (such as DCM).

Intermediate 2.3 can then be converted to acid 2.4 under suitable hydrolysis conditions such as base (such as NaOH) in a solvent (such as water, DMSO or EtOH) at temperatures between 50 and 170° C. Thienopyridine intermediate 2.5 can then be obtained from acid 2.4 under suitable conditions (such as heating to temperatures between 150 and 220° C. in diphenylether or Cu/quinoline).

Compound I(b) can be obtained by treatment of intermediate 2.5 with a sulfonyl chloride 1.11 in the presence of a base (such as LiHMDS, KOtBu or NaOtBu) in a solvent (such as THF, DMF) at temperatures between 20 and 50° C.

Compound I(a) can be obtained by treatment of compound I(b) with a boronic acid or ester 2.6 in the presence of a catalyst (such as $PdCl_2(dppf).DCM$, $Pd(PPh_3)_4$, $Pd(PPh_3)_2Cl_2$ or $Pd(OAc)_2$/Xantphos) and a base (such as $Cs_2CO_3$, $Na_2CO_3$ or $K_2CO_3$) in a solvent (such as DMF, water, acetonitrile, toluene or 1,4-dioxane) at temperatures between 50 and 120° C.

Treatment of intermediate 2.3 with a boronic acid or ester 2.6 in the presence of a catalyst (such as $PdCl_2(dppf).DCM$, $Pd(PPh_3)_4$ or $Pd(PPh_3)_2Cl_2$) and a base (such as $K_2CO_3$ or $Cs_2CO_3$) in a solvent (such as acetonitrile, 1,4-dioxane, toluene or water) at temperatures between 50 and 160° C. can give thienopyridine 2.7. Intermediate 2.7 can then be converted to acid 2.8 under suitable hydrolysis conditions such as base (such as NaOH) in a solvent (such as water, ethanol or DMSO) at temperatures between 50 and 170° C. Intermediate 1.10 can be obtained from acid 2.8 under suitable conditions (such as heating to temperatures between 150 and 220° C. in diphenylether).

Compound I(a) can be obtained by treatment of intermediate 1.10 with a sulfonyl chloride 1.11 in the presence of a base (such as LiHMDS, KOtBu or NaOtBu) in a solvent (such as THF or DMF) at temperatures between 20 and 50° C.

Treatment of 2.3 with a sulfonyl chloride 1.11 in the presence of a base (such as LiHMDS, KOtBu or NaOtBu) in a solvent (such as THF or DMF) at temperatures between 20 and 50° C. gives 2.9. Treatment of intermediate 2.9 with a boronic acid or ester 2.6 in the presence of a catalyst (such as $PdCl_2(dppf).DCM$, $Pd(PPh_3)_4$ or $Pd(PPh_3)_2Cl_2$) and a base (such as $K_2CO_3$ or $Cs_2CO_3$) in a solvent (such as acetonitrile, 1,4-dioxane, toluene, DMF or water) at temperatures between 50 and 160° C. can afford thienopyridine 2.10. In the case where R1 is a pyrazole protected with a Boc group, the Boc is removed under these conditions. Intermediate 2.10 can then be converted to I(a) under suitable hydrolysis conditions such as base (such as NaOH) in a solvent (such as water, ethanol or DMSO) at temperatures between 50 and 170° C. followed by decarboxylation under appropriate conditions (such as heating to temperatures between 150 and 220° C. in diphenylether) optionally with a co-solvent (such as DMSO).

Treatment of 2.2 with a sulfonyl chloride 1.11 in the presence of a base (such as LiHMDS, KOtBu or NaOtBu) in a solvent (such as THF or DMF) at temperatures between 20 and 50° C. followed by suitable hydrolysis conditions such as base (such as NaOH) in a solvent (such as water, ethanol or DMSO) at temperatures between 50 and 170° C. followed by decarboxylation under appropriate conditions (such as heating to temperatures between 150 and 220° C. in diphenylether) optionally with a co-solvent (such as DMSO) can give I(a).

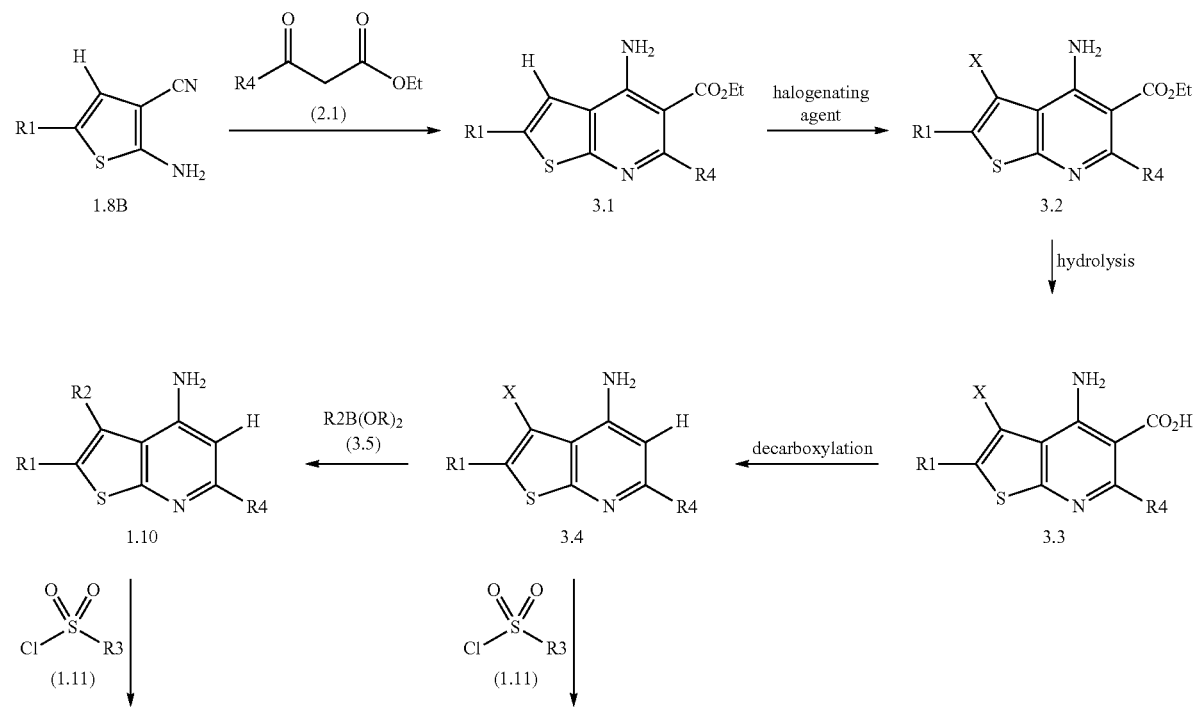

Scheme 3

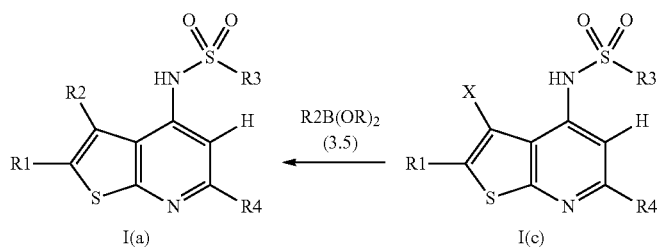

Scheme 3 represents another general reaction scheme for preparing intermediates and certain compounds of Formula I. In Scheme 3, X is halo which represents R2. Intermediate 3.1 can be obtained by treatment of intermediate 1.8B in the presence of a reagent (such as SnCl₄) in a solvent (such as toluene) at temperatures between 20 and 160° C. Intermediate 3.1 can then be converted to halide 3.2 in the presence of an appropriate halogenating agent (such as N-bromosuccinimide) in a solvent (such as DCM). 3.2 can then be converted to acid 3.3 under suitable hydrolysis conditions such as base (such as NaOH) in a solvent (such as water, ethanol or DMSO) at temperatures between 50 and 170° C. Decarboxylation of acid 3.3 can then be carried out under suitable conditions such as heating to temperatures between 150 and 220° C. in diphenylether to give thienopyridine 3.4.

Intermediate 1.10 can then be obtained from 3.4 by reaction with a boronic acid or ester 3.5 in the presence of a catalyst (such as PdCl₂(dppf).DCM, Pd(PPh₃)₄ or Pd(PPh₃)₂Cl₂) and a base (such as K₂CO₃ or Cs₂CO₃) in a solvent (such as acetonitrile, 1,4-dioxane, toluene, DMF or water) at temperatures between 70 and 160° C.

Compound I(a) can be obtained by treatment of intermediate 1.10 with a sulfonyl chloride 1.11 in the presence of a base (such as LiHMDS, KOtBu or NaOtBu) in a solvent (such as THF or DMF) at temperatures between 20 and 50° C.

Compound I(c) can be obtained by treatment of intermediate 3.4 with a sulfonyl chloride 1.11 in the presence of a base (such as KOtBu) in a solvent (such as THF or DMF) at temperatures between 20 and 50° C. Compound I(c) can then be converted to compound I(a) by treatment of compound I(c) with a boronic acid or ester 3.5 in the presence of a catalyst (such as PdCl₂(dppf).DCM, Pd(PPh₃)₄ or Pd(PPh₃)₂Cl₂) and a base (such as Cs₂CO₃ or K₂CO₃) in a solvent (such as 1,4-dioxane, toluene, DMF or water) at temperatures between 100 and 190° C.

Where a protecting group (such as Boc) is present in I(a) this can be deprotected under appropriate conditions (such as 4M HCl or TFA) optionally in a solvent (such as DCM or 1,4-dioxane).

Scheme 4

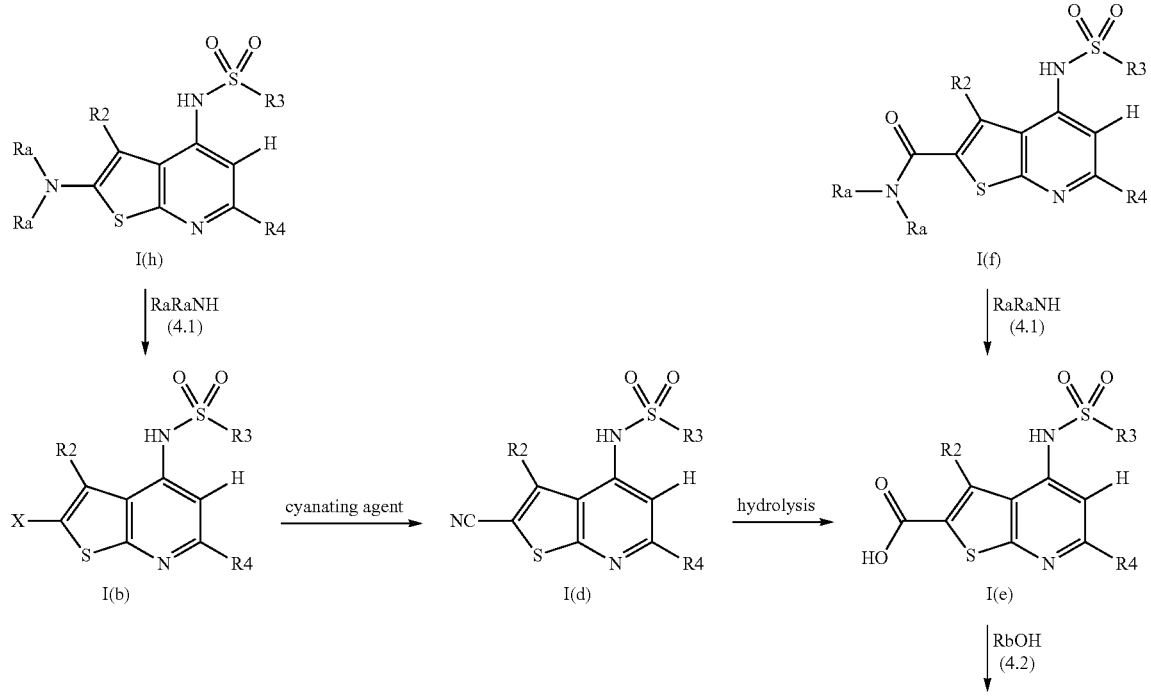

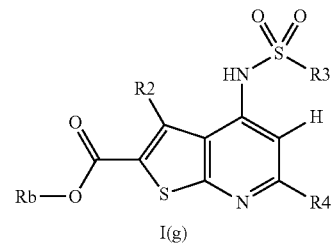

Scheme 4 represents another general reaction scheme for preparing intermediates and certain compounds of Formula I. In Scheme 4, X is halo which represents R1. Compound I(d) (wherein R1 is CN) can be obtained by treatment of compound I(b) with a cyanating agent (such as potassium ferrocyanide) in the presence of a catalyst (such as copper(I) iodide) in a solvent (such as 1-methylimidazole) at temperatures between 100 and 160° C. Compound I(e) (wherein R1 is COOH) can be obtained from compound I(d) under hydrolysis conditions (such as conc HCl or 4M HCl in 1,4-dioxane) in a solvent (such as water or 1,4-dioxane) at temperatures between 20 and 160° C. Compound I(f) (wherein R1 is CONRaRa) can be obtained by treatment of compound I(e) with an amine 4.1 under suitable coupling conditions (such as oxalyl chloride/DMF) in a solvent (such as DCM), at temperatures between 0 and 50° C. Compound I(g) (wherein R1 is COORb) can be obtained from compound I(e) by treatment with an alcohol 4.2 under appropriate ester formation conditions (such as conc sulfuric acid) in a solvent (such as water) at temperatures between 20 and 100° C.

Compound I(h) (wherein R1 is NRaRa) can be obtained by treatment of compound I(b) with an amine 4.1 in the presence of a catalyst (such as $Pd_2(dba)_3$), a ligand (such as 2-di-t-butylphosphino-2',4',6'-triisopropylbiphenyl) and a base (such as $Cs_2CO_3$) in a solvent (such as THF) at temperatures between 50 and 100° C.

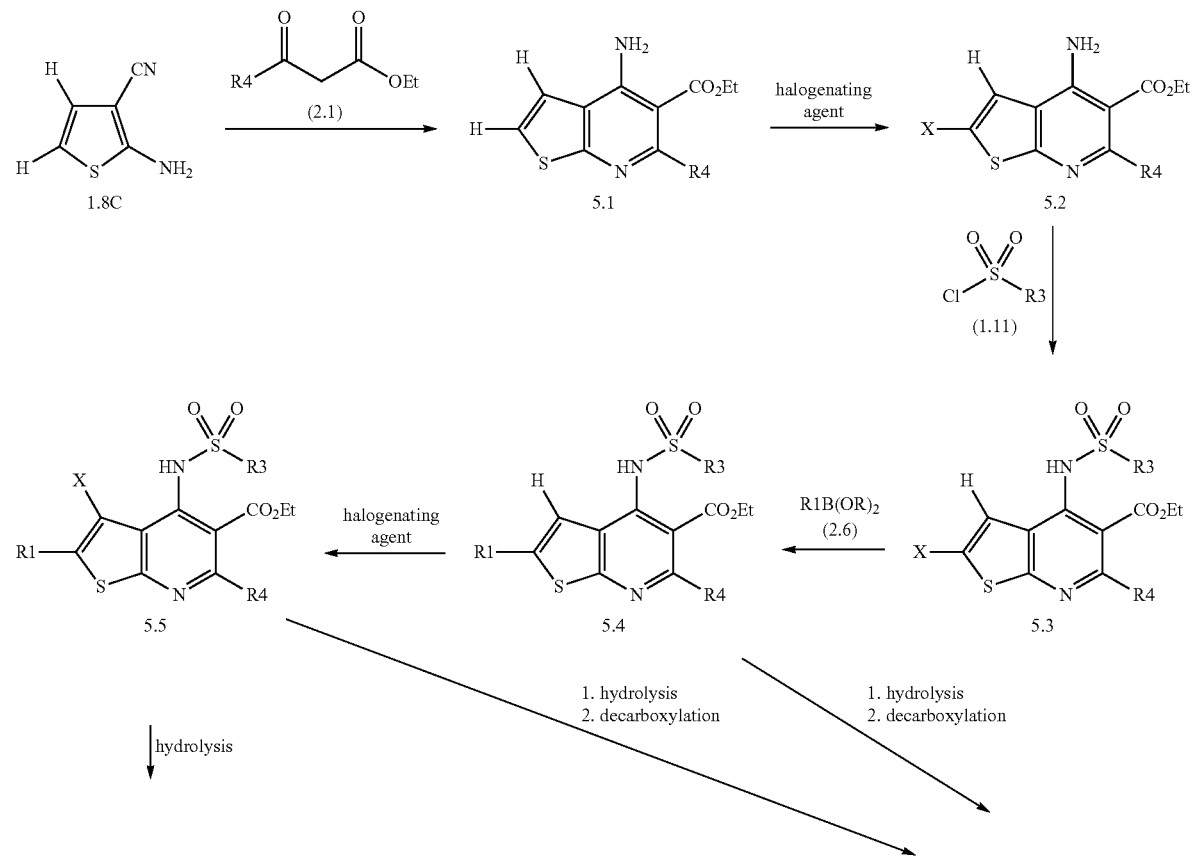

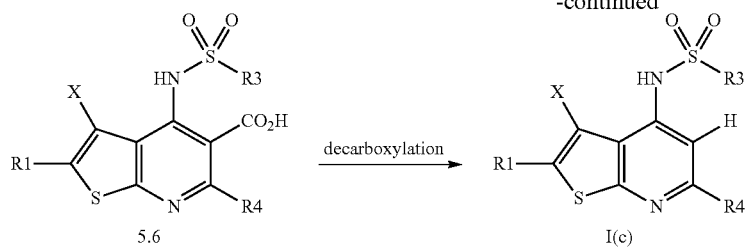
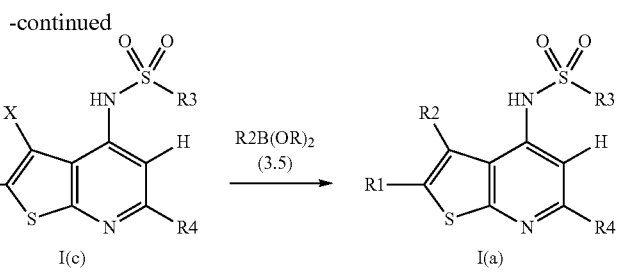

Scheme 5 represents another general reaction scheme for preparing intermediates and certain compounds of Formula I. In Scheme 5, X is halo which represents R2. Intermediate 5.1 can be obtained by treatment of intermediate 1.8C with a ketoester 2.1 in the presence of a reagent (such as $SnCl_4$) in a solvent (such as toluene) at temperatures between 20 and 160° C. 5.1 can then be converted to 5.2 in the presence of an appropriate halogenating agent (such as bromine or N-bromosuccinimide) in a solvent (such as acetic acid or DCM). Intermediate 5.3 can be obtained by treatment of intermediate 5.2 with a sulfonyl chloride 1.11 in the presence of a base (such as LiHMDS, KOtBu or NaOtBu) in a solvent (such as THF or DMF) at temperatures between 20 and 50° C. Intermediate 5.4 can then be obtained by treatment of intermediate 5.3 with a boronic acid or ester 2.6 in the presence of a catalyst (such as $PdCl_2(dppf).DCM$, $Pd(PPh_3)_4$ or $Pd(PPh_3)_2Cl_2$) and a base (such as $Cs_2CO_3$ or $K_2CO_3$) in a solvent (such as 1,4-dioxane, DMF or water) at temperatures between 100 and 190° C. 5.4 can be converted to halide 5.5 in the presence of an appropriate halogenating agent (such as bromine or N-bromosuccinimide) in a solvent (such as $CHCl_3$) at temperatures between 20 and 80° C. Hydrolysis and decarboxylation of 5.4 or 5.5 under suitable conditions such as base (such as NaOH) in a solvent (such as water or DMSO) at temperatures between 50 and 170° C. followed by heating to temperatures between 150 and 220° C. optionally in solvent (such as diphenylether, DMF or quinoline) gives directly compound I(a). Alternatively, intermediate 5.5 can then be converted to 5.6 under suitable hydrolysis conditions such as base (such as NaOH) in a solvent (such as water or DMSO) at temperatures between 50 and 170° C. Subsequent heating to temperatures between 150 and 220° C. in solvent (such as diphenylether, DMF or quinoline) gives compound I(c). Where appropriate (such as when R1 is pyrazole) the R1 moiety of compound I(c) can be protected with using a reagent (such as $Boc_2O$ or SEMCl) in the presence of base (such as $Et_3N$, DMAP or NaH) in a solvent (such as acetonitrile or THF) at temperatures between 20 and 50° C. I(c) (or a protected version as described above) was then treated with a boronic acid or ester 3.5 in the presence of a catalyst (such as $PdCl_2(dppf).DCM$, $Pd(PPh_3)_4$ or $Pd(PPh_3)_2Cl_2$) and a base (such as $Cs_2CO_3$ or $K_2CO_3$) in a solvent (such as 1,4-dioxane, DMF or water) at temperatures between 100 and 190° C. to give compound I(a). In the case where R1 is a pyrazole protected with a Boc group, the Boc is removed under these conditions.

I(c) (wherein X is Br) can be converted into I(c) (wherein X is F) using an appropriate reagent (such as nBuLi) in a solvent (such as THF) at an appropriate temperature (such as −78° C.) followed by the addition of a fluorinating agent (such as N-fluorobenzenesulfonimide). Where a protecting group (such as Boc) is present in I(a) this can be deprotected under appropriate conditions (such as 4M HCl or TFA) optionally in a solvent (such as DCM or 1,4-dioxane).

Scheme 6

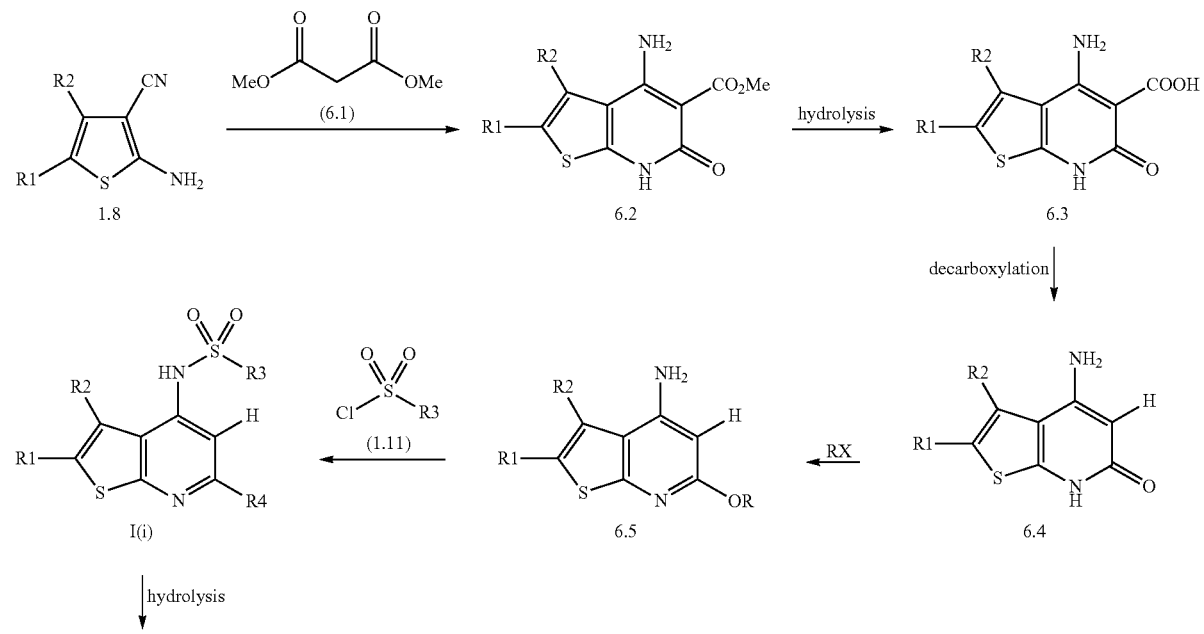

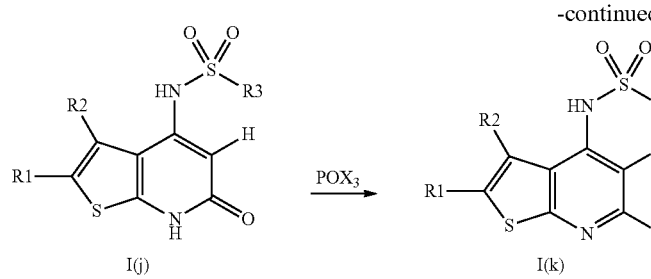
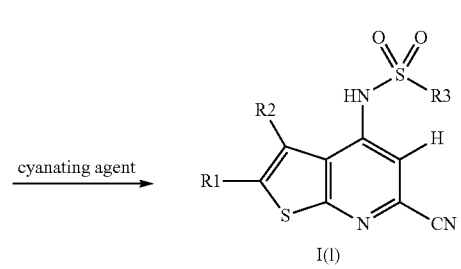

Scheme 6 represents another general reaction scheme for preparing intermediates and certain compounds of Formula I. In Scheme 6, X is halo which represents R4. Intermediate 6.2 can be obtained by treatment of intermediate 1.8 with dimethyl malonate 6.1 in the presence of a reagent (such as SnCl$_4$) in a solvent (such as toluene) at temperatures between 20 and 160° C. 6.2 can then be converted to thienopyridone 6.4 under suitable hydrolysis conditions such as base (such as NaOH) in a solvent (such as water, ethanol or DMSO) at temperatures between 50 and 170° C. followed by decarboxylation under suitable conditions such as heating to temperatures between 150 and 220° C. in diphenylether. Thienopyridone 6.4 can then be alkylated with alkylating agent (such as MeI) in the presence of base (such as K$_2$CO$_3$) in a solvent (such as DMF) a temperatures between 20 and 120° C. to give intermediate 6.5. Compound I(i) can be obtained by treatment of intermediate 6.5 with a sulfonyl chloride 1.11 in the presence of a base (such as LiHMDS, KOtBu or NaOtBu) in a solvent (such as THF) at temperatures between −78 and 50° C. Compound I(j) can then be obtained from compound I(i) under hydrolysis conditions (such as conc HCl or 4M HCl in 1,4-dioxane) in a solvent (such as water or 1,4-dioxane) at temperatures between 20 and 160° C. Compound I(j) can then be converted to compound I(k) in the presence of an appropriate reagent (such as POCl$_3$, or phenylphosphonic dichloride) at temperatures between 20 and 220° C. Compound I(l) (wherein R4 is CN) can be obtained by treatment of compound I(k) with a cyanating agent (such as potassium ferrocyanide) in the presence of a catalyst (such as copper(I) iodide) in a solvent (such as 1-methylimidazole) at temperatures between 100 and 160° C.

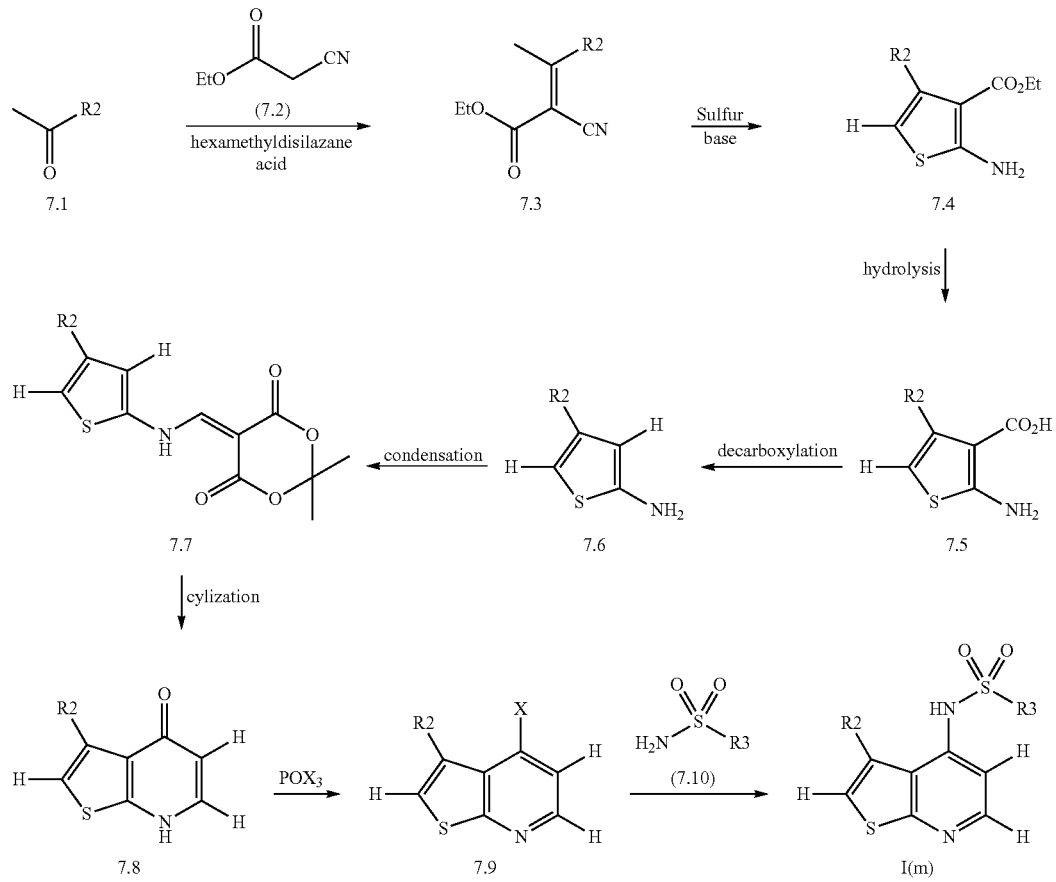

Scheme 7 represents another general reaction scheme for preparing intermediates and certain compounds of Formula I. Intermediate 7.3 can be obtained by treatment of the corresponding ketone 7.1 with ethyl cyanoacetate 7.2 in hexamethyldisilazane and an acid (such as acetic acid) at temperatures between 20 and 80° C. Thiophene intermediate 7.4 can be obtained from 7.3 by treatment with sulfur in the presence of a base (such as NaHCO$_3$) in solvents (such as THF/water) at temperatures between 20 and 50° C. 7.4 can then be converted to thiophene 7.6 under suitable conditions such as base (such as KOH) in a solvent (such as water, ethanol or DMSO) at temperatures between 20 and 120° C. Intermediate 7.7 was obtained by condensing intermediate 7.6 with Meldrum's acid and a reagent (such as trimethyl orthoformate) at temperatures between 20 and 120° C. Intermediate 7.7 was then cyclized under suitable conditions (such as heating) at temperatures between 150 and 220° C. in diphenylether to give thienylpyridone 7.8 which was then converted to intermediate 7.9 (wherein X is halo) in the presence of an appropriate reagent (such as POCl$_3$) at temperatures between 20 and 120° C. Compound I(m) can be obtained by treatment of intermediate 7.9 with sulfonamide 7.10 in the presence of a catalyst (such as Pd(OAc)$_2$), a ligand (such as Xantphos) and a base (such as Cs$_2$CO$_3$) in a solvent (such as 1,4-dioxane) at temperatures between 20 and 150° C.

temperatures between 50 and 170° C. Decarboxylation of acid 8.4 can then be carried out under suitable conditions such as heating to temperatures between 150 and 220° C. in Cu/quinoline to give thienopyridine I(n). Compound I(o) can be obtained from I(n) by treatment with an acid chloride 8.5 under appropriate amide formation conditions such as base (such as Et$_3$N) in a solvent (such as DCM) at temperatures between 20 and 50° C.

Scheme 9

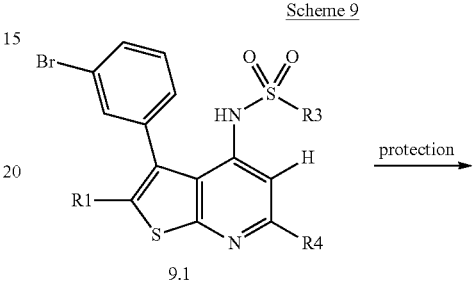

Scheme 8

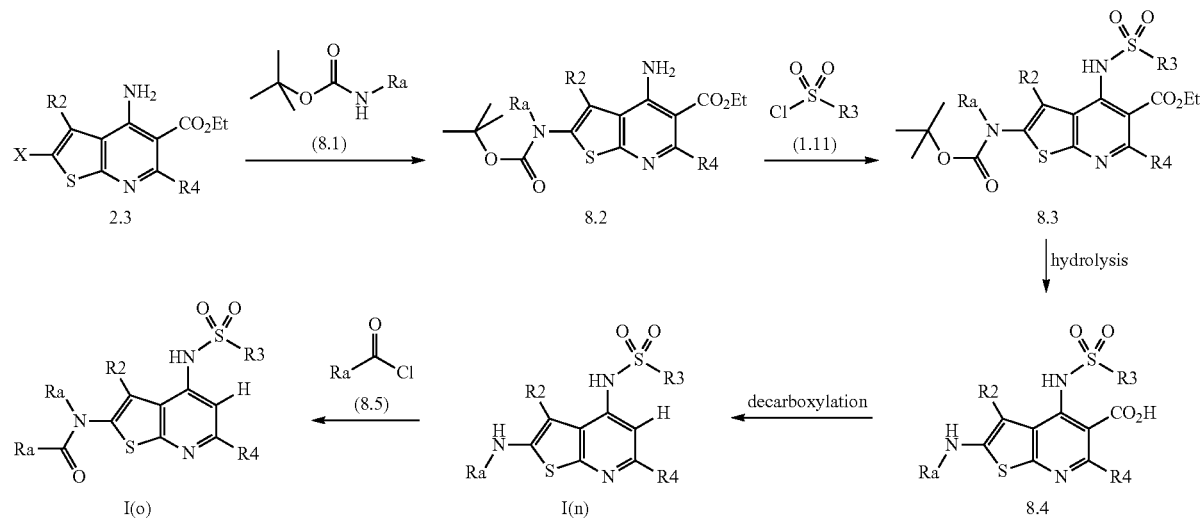

Scheme 8 represents another general reaction scheme for preparing intermediates and certain compounds of Formula I. In Scheme 8, X is halo which represents R1. Intermediate 8.2 can be obtained by treatment of intermediate 2.3 (which may be prepared as described in Scheme 2) with a protected amine (such as 8.1) in the presence of a catalyst (such as Pd$_2$(dba)$_3$), a ligand (such as Xantphos) and a base (such as Cs$_2$CO$_3$) in a solvent (such as 1,4-dioxane) at temperatures between 20 and 120° C. Intermediate 8.3 can be obtained by treatment of intermediate 8.2 with a sulfonyl chloride 1.11 in the presence of a base (such as NaOtBu) in a solvent (such as THF or DMF) at temperatures between 20 and 50° C. 8.3 can then be converted to acid 8.4 under suitable hydrolysis conditions such as base (such as NaOH) in a solvent (such as water or DMSO) at -continued

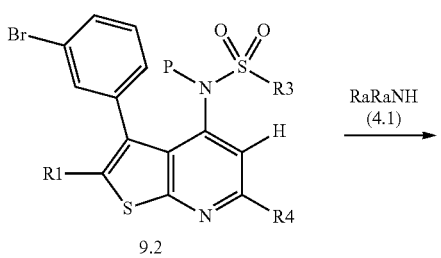

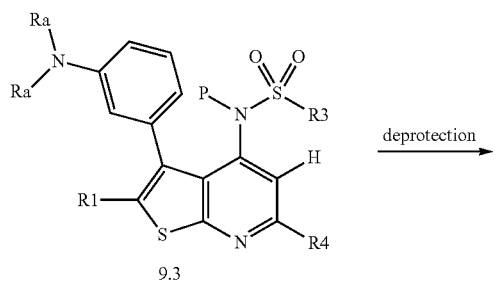

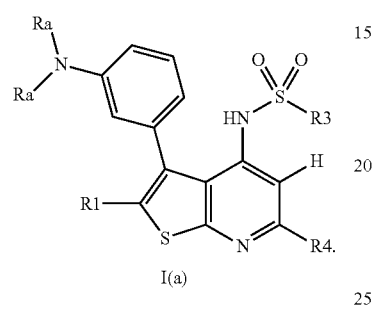

Scheme 9 represents another general reaction scheme for preparing intermediates and certain compounds of Formula I. Compound 9.1 (which may be prepared as described in Scheme 2) is converted to intermediate 9.2 (where P is a protecting group) using an appropriate protecting group (such as SEMCl) in the presence of base (such as DIPEA) in a solvent (such as DCM) at temperatures between 20 and 50° C. In some cases (such as when R1 is pyrazole), a free NH group present in the R1 moiety may also be protected under these conditions. Intermediate 9.3 can be obtained by treatment of intermediate 9.2 with an amine 4.1 in the presence of a catalyst (such as $Pd_2(dba)_3$), a ligand (such as BINAP) and a base (such as NaOtBu) in a solvent (such as toluene) at temperatures between 20 and 120° C. Compound I(a) can be obtained by deprotection of intermediate 9.3 (including deprotection of the R1 moiety where appropriate) with an acid (such as TFA) optionally in solvent (such as DCM).

Scheme 10

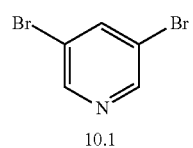

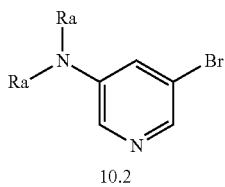

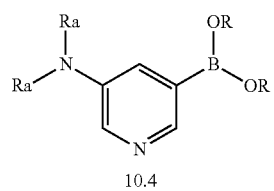

Scheme 10 represents a general reaction scheme for preparing intermediate 10.4. Intermediate 10.2 can be obtained by treatment of intermediate 10.1 with an amine 4.1 in the presence of a catalyst (such as $Pd_2(dba)_3$), a ligand (such as BINAP) and a base (such as NaOtBu) in a solvent (such as toluene) at temperatures between 20 and 120° C. Intermediate 10.4 can be obtained by treatment of intermediate 10.2 with bis pinacol boronic ester 10.3 in the presence of a catalyst (such as $PdCl_2(dppf).DCM$, $Pd(PPh_3)_4$ or $Pd(PPh_3)_2Cl_2$) and a base (such as potassium acetate) in a solvent (such as DMF or 1,4-dioxane) at temperatures between 100 and 120° C.

Scheme 11

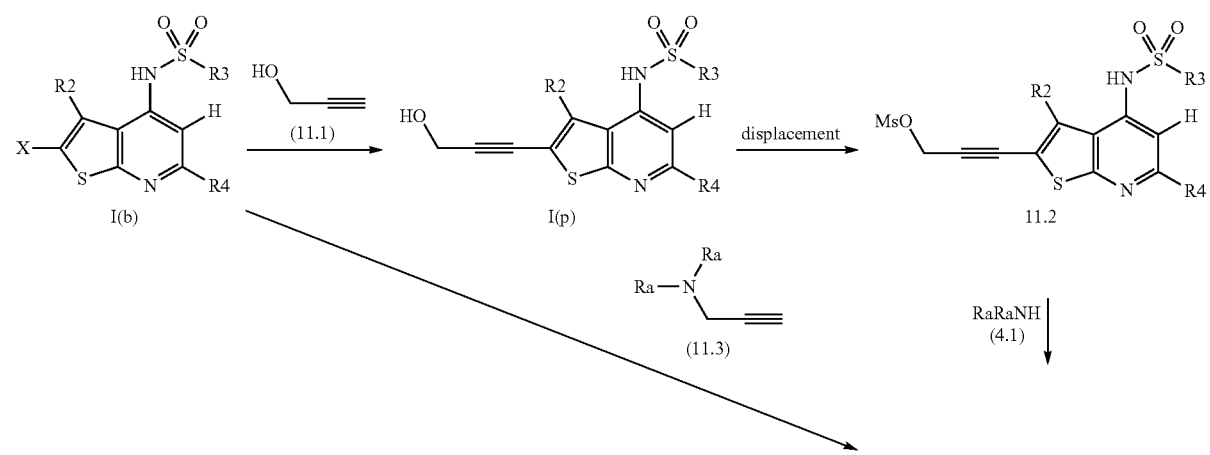

-continued

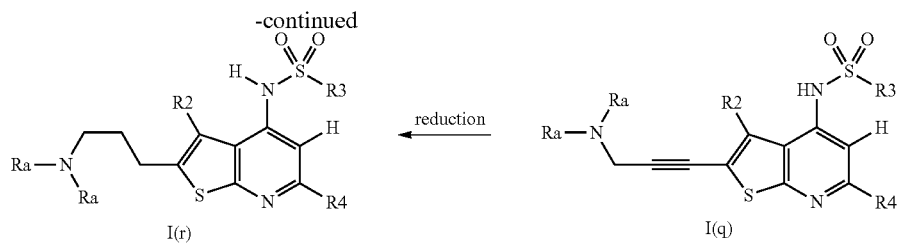

I(r)    I(q)

Scheme 11 represents another general reaction scheme for preparing intermediates and certain compounds of Formula I. In Scheme 11, X is halo which represents R1. Compound I(p) can be obtained by treatment of compound I(b) with a propargyl alcohol 11.1 in the presence of a catalyst (such as copper(I) iodide, Pd(PPh$_3$)$_2$Cl$_2$) and a base (such as Et$_3$N) in a solvent (such as THF) at temperatures between 20 and 80° C. Compound I(p) can be converted into 11.2 by displacement with a reagent (such as methane sulfonyl chloride) in the presence of base (such as Hunig's base) in a solvent (such as THF) at temperatures between 0 and 20° C. Compound I(q) can be obtained by treatment of intermediate 11.2 with an amine 4.1 in a solvent (such as THF), at temperatures between 20 and 70° C. Alternatively, I(q) can be obtained directly from I(b) with an appropriate alkyne (such as 11.3) in the presence of a catalyst (such as copper(I) iodide, Pd(PPh$_3$)$_2$Cl$_2$) and a base (such as Et$_3$N) in a solvent (such as THF) at temperatures between 20 and 80° C. Compound I(r) can be obtained from compound I(q) by reduction under suitable reduction condition (such as palladium on carbon) in a solvent (such as EtOH) at temperatures between 20-30° C.

Scheme 12

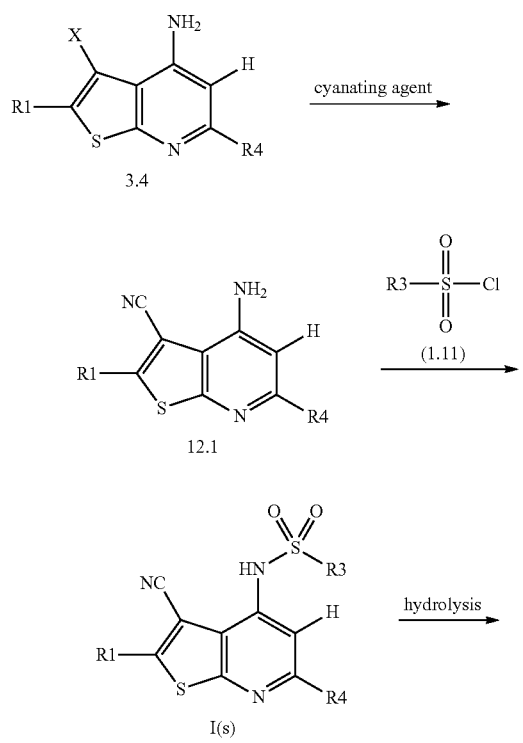

-continued

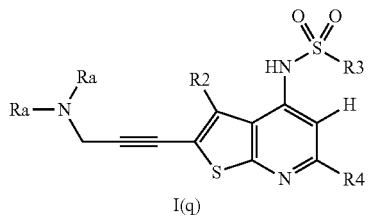

I(t)

Scheme 12 represents another general reaction scheme for preparing intermediates and certain compounds of Formula I. In Scheme 12, X is halo which represents R2. Intermediate 12.1 (wherein R2 is CN) can be obtained by treatment of intermediate 3.4 with a cyanating agent (such as zinc cyanide) in the presence of a catalyst (such as Pd(PPh$_3$)$_4$,) in a solvent (such as DMF) at temperatures between 100 and 160° C. Compound I(s) can be obtained by treatment of intermediate 12.1 with a sulfonyl chloride 1.11 in the presence of a base (such as KOtBu) in a solvent (such as THF or DMF) at temperatures between 20 and 50° C. Compound I(t) (wherein R2 is CONH$_2$) can be obtained from compound I(s) under hydrolysis conditions (such as 3M NaOH in water) in a solvent (such as DMSO) at temperatures between 20 and 160° C.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Abbreviations

Cbz: Carboxybenzyl; DCM: Dichloromethane; DMF: N,N-Dimethylformamide; DMSO: Dimethyl sulfoxide; h: Hour(s); HCl: Hydrochloric acid; HPLC: High Performance Liquid Chromatography; LCMS: Liquid Chromatography Mass Spectrometry; LiHMDS: Lithium bis(trimethylsilyl) amide; M: Molarity; MDAP: Mass Directed Auto Purification system; NMR: Nuclear Magnetic Resonance; Pd$_2$(dba)$_3$: Tris(dibenzylideneacetone)dipalladium(0); PdCl$_2$(dppf). DCM:1,1'-bis(diphenylphosphino)-ferrocene-palladium(II) dichloride dichloromethane; Pd(PPh$_3$)$_2$Cl$_2$: bis(triphenylphosphine)palladium(II) chloride; RT: Room temperature; Rt: Retention time; TFA: Trifluoroacetic acid; THF: Tetrahydrofuran; xantphos: 4,5-Bis(diphenylphosphino)-9, 9-dimethylxanthene; SEMCl: 2-(Trimethylsilyl)ethoxymethyl chloride; M: Molarity; DIPEA: N,N-Diisopropylethylamine; BINAP: 2,2'-bis(diphenylphosphino)-1,1'- binaphthyl; Hunig's base: N,N-Diisopropylethylamine; SCX: Strong Cationic Exchange resin; DMAP: 4-Dimethylaminopyridine; Boc$_2$O: Di-tert-butyl dicarbonate; Xantphos: 4,5-Bis(diphenylphosphino)-9,9-dimethylxanthene.

All other abbreviations and symbols utilized herein are in accordance with the common usage of such abbreviations and symbols by those skilled in the chemical and biological arts.

Conditions for LCMS and HPLC
LCMS (A) and MDAP:
1) Basic Conditions:
Mobile phase: water 0.2% diethylamine-acetonitrile 0.2% diethylamine; Column: xBridge™ C18 30×100 mm—5 microns;
Detection: MS and photodiode array detector (PDA)
2) Acidic Conditions:
Mobile phase: water 0.2% formic acid-acetonitrile 0.2% formic acid
Column: xBridge™ C18 30×100 mm—5 microns
Detection: MS and photodiode array detector (PDA)

LCMS (B) was conducted on an Agilent 1100 Series LC/MSD SL or VL using electrospray positive [ES+ve to give MH$^+$] equipped with a Sunfire C$_{18}$ 5.0 μm column (3.050 mm×50 3.0 mm, i.d.), eluting with 0.05% TFA in water (solvent A) and 0.05% TFA in acetonitrile (solvent B), using the following elution gradient 10%-99% (solvent B) over 3.0 minutes and holding at 99% for 1.0 minutes at a flow rate of 1.0 mL/minutes.

Preparative HPLC (A) was conducted on a Gilson instrument using a Sunfire Prep C18 column (5 uM, 30×100 mm, i.d.) eluting with water (+0.1% TFA)/acetonitrile (+0.1% TFA) (20%→60%, 50 mL/min) over a 12-minute gradient.

Preparative HPLC (B) was conducted on a Waters instrument using a Sunfire Prep C18 column (5 uM, 30×150 mm, i.d.) eluting with water (+0.1% TFA)/acetonitrile (+0.1% TFA) (20%→60%, 45 mL/min) over a 14-minute gradient.

Description 1

1-[3-(Methyloxy)phenyl]-1-propanone

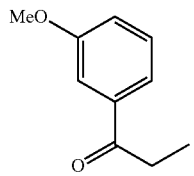

To a stirred solution of 3-(methyloxy)benzaldehyde (0.895 mL, 7.34 mmol) in diethyl ether (10 mL) cooled in an ice bath was added ethylmagnesium bromide (1.0M solution in THF) (11.02 mL, 11.02 mmol), the solution was stirred for 3 h in an ice bath, after which aqueous HCl (0.6M) (20 mL) was added. The aqueous layer was then extracted with DCM (4×30 mL), the combined organic extracts were dried over a phase separating column and concentrated. The residue was used in the next step without any further purification. To a solution of oxalyl chloride (0.964 mL, 11.02 mmol) in DCM (4 mL) cooled to −78° C. was added DMSO (1.042 mL, 14.69 mmol) dropwise, followed by a solution of the material isolated in the first step in DCM (6 mL). The resulting mixture was stirred for 1 h at −78° C. before the addition of triethylamine (5.12 mL, 36.7 mmol), after which the reaction mixture was stirred at −78° C. for 1 h. The reaction was quenched at −78° C. by water (20 mL). The aqueous layer was then extracted with DCM (3×50 mL), the combined organic extracts were dried over a phase separating column and concentrated. Purification by chromatography on silica gel, eluting with a gradient of 0-25% ethyl acetate in cyclohexane, afforded the title compound (1.126 g). LCMS (A) m/z: 165 [M+1]$^+$, Rt 1.32 min (basic).

Description 2

{1-[3-(Methyloxy)phenyl]propylidene}propanedinitrile

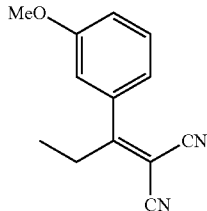 [SMILES: CCC(=C(C#N)C#N)c1cccc(OC)c1]

Hexamethyldisilazane (5.51 mL, 26.3 mmol) was added dropwise to acetic acid (11.30 mL, 197 mmol) at RT under nitrogen. The resulting solution was then added to a solution of 1-[3-(methyloxy)phenyl]-1-propanone (Description 1) (2.7 g, 16.44 mmol) and malonitrile (2.173 g, 32.9 mmol) in acetic acid (10 mL). The reaction mixture was stirred at 70° C. for 12 h. The reaction mixture was cooled to RT then diluted with water (30 mL), the aqueous layer was then extracted with DCM (3×50 mL) and the combined organic extracts were dried over a phase separating column and concentrated. Purification by chromatography on silica gel, eluting with a gradient of 0-20% ethyl acetate in cyclohexane, afforded the title compound (3.13 g). LCMS (A) m/z: 211 [M−1]$^−$, Rt 1.40 min (basic).

Description 3

2-Amino-5-methyl-4-[3-(methyloxy)phenyl]-3-thiophenecarbonitrile

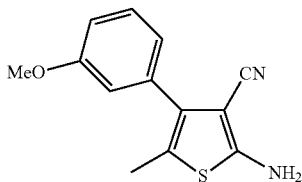 [SMILES: COc1cccc(-c2c(C)sc(N)c2C#N)c1]

To a stirred suspension of 1-[3-(methyloxy)phenyl]propylidene}propanedinitrile (Description 2) (1.2 g, 5.65 mmol) and sulfur (0.218 g, 6.78 mmol) in THF (8 mL) at 35° C. was added a solution of NaHCO$_3$ (0.570 g, 6.78 mmol) in water (4 mL). The reaction mixture was stirred at 35° C. for 16 h. The reaction mixture was cooled to RT then diluted with water (25 mL), the aqueous layer was then extracted with DCM (4×40 mL), and the combined organic extracts were dried over a phase separating column and concentrated. Purification by chromatography on silica gel, eluting with a gradient of 0-25% ethyl acetate in cyclohexane, afforded the title compound (1.3 g). LCMS (A) m/z: 245 [M+1]$^+$, Rt 1.33 min (basic).

Description 4

2,6-Dimethyl-3-[3-(methyloxy)phenyl]thieno[2,3-b]pyridin-4-amine

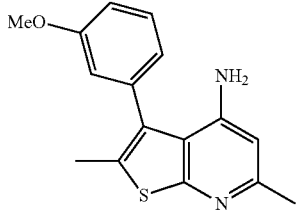 [SMILES: COc1cccc(-c2c(C)sc3nc(C)cc(N)c23)c1]

To a solution of 2-amino-5-methyl-4-[3-(methyloxy)phenyl]-3-thiophenecarbonitrile (Description 3) (260 mg, 1.064 mmol) in toluene (2.5 mL), were added at RT, acetone (0.094 mL, 1.277 mmol) and SnCl$_4$ (0.150 mL, 1.277 mmol), the reaction mixture was stirred for 5 min at RT then for 15 min at 150° C. in a microwave. The reaction mixture was cooled to RT then diluted with aqueous NaOH (1M) until the solution turned basic. The aqueous layer was then extracted with DCM (3×30 mL), the combined organic extracts were dried over a phase separating column and concentrated. Purification by chromatography on silica gel, eluting with a gradient of 0-30% ethyl acetate in cyclohexane, afforded the title compound (167 mg). LCMS (A) m/z: 285 [M+1]$^+$, Rt 1.20 min (basic).

Description 5

Ethyl 4-amino-2,6-dimethylthieno[2,3-b]pyridine-5-carboxylate

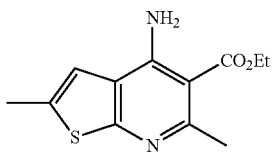 [SMILES: CCOC(=O)c1c(C)nc2sc(C)cc2c1N]

To a solution of 2-amino-5-methyl-3-thiophenecarbonitrile (5 g, 36.2 mmol), ethyl 3-oxobutanoate (5.49 mL, 43.4 mmol) in toluene (200 mL) was added SnCl$_4$ (5.10 mL, 43.4 mmol). The resulting mixture was refluxed for 2 h after which the heater was switched off. SnCl$_4$ (2.123 mL, 18.09 mmol) was added and the mixture refluxed for another 4 h. The solution was cooled and aqueous NaOH (5M) was added until the solution turned basic. Ethyl acetate (100 mL) was added and washed with water (3×30 mL). The organic layer was dried over MgSO$_4$, filtered and solvent removed in vacuo. Purification by chromatography on silica gel, eluting with a gradient of 0-50% ethyl acetate in cyclohexane afforded the title compound (6.48 g). LCMS (A) m/z: 251 [M+1]$^+$, Rt 0.74 min (acidic).

Description 6

Ethyl 4-amino-3-bromo-2,6-dimethylthieno[2,3-b]pyridine-5-carboxylate

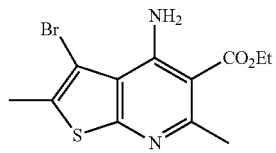 [SMILES: CCOC(=O)c1c(C)nc2sc(C)c(Br)c2c1N]

To a stirred solution of ethyl 4-amino-2,6-dimethylthieno[2,3-b]pyridine-5-carboxylate (6.44 g, 25.7 mmol) (Description 5) in DCM (110 mL), was added N-bromosuccinimide (9.16 g, 51.5 mmol) and the resulting mixture was stirred for 1 h. The mixture was concentrated and the solid that precipitated was filtered and washed with DCM (3×10 mL), to afford the title compound (9.44 g). LCMS (A) m/z: 329/331 [M+1]$^+$, Rt 1.22 min (acidic).

Description 7

4-Amino-3-bromo-2,6-dimethylthieno[2,3-b]pyridine-5-carboxylic acid

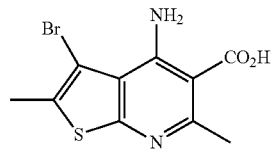 [SMILES: Cc1nc2sc(C)c(Br)c2c(N)c1C(=O)O]

To a solution of ethyl 4-amino-3-bromo-2,6-dimethylthieno[2,3-b]pyridine-5-carboxylate (5 g, 15.19 mmol) (Description 6) in ethanol (50 mL) was added aqueous NaOH (3M) (20.25 mL, 60.8 mmol) and the mixture stirred at 100° C. for 1 h. The reaction mixture was cooled and combined with material (4.43 g) from a similar reaction. The combined solution was acidified with aqueous HCl (1M) to pH 6-7. Ethanol was removed in vacuo. Water (50 mL) was added and the mixture extracted with DCM (5×50 mL). The combined organics were dried over MgSO$_4$, filtered and solvent removed in vacuo, to afford the title compound (2.98 g). LCMS (A) m/z: 301/303 [M+1]$^+$, Rt 0.73 min (acidic).

Description 8

3-Bromo-2,6-dimethylthieno[2,3-b]pyridin-4-amine

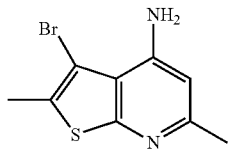

To 4-amino-3-bromo-2,6-dimethylthieno[2,3-b]pyridine-5-carboxylic acid (1.95 g, 6.47 mmol) (Description 7) was added diphenyl ether (15 mL, 94 mmol) and the mixture heated at 200° C. for 4 h. This crude mixture was cooled and combined with material (1 g) from a similar reaction. Purification by chromatography on silica gel, eluting with a gradient of 0-50% ethyl acetate in cyclohexane afforded the title compound (1.82 g). LCMS (A) m/z: 257/259 [M+1]⁺, Rt 0.67 min (acidic).

Description 9

3-(3-Chlorophenyl)-2,6-dimethylthieno[2,3-b]pyridin-4-amine

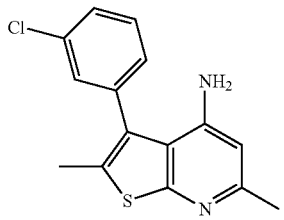 [SMILES: Cc1cc(N)c2c(-c3cccc(Cl)c3)c(C)sc2n1]

Under nitrogen, 3-bromo-2,6-dimethylthieno[2,3-b]pyridin-4-amine (170 mg, 0.661 mmol) (Description 8) was dissolved in toluene (6 mL) and (3-chlorophenyl)boronic acid (155 mg, 0.992 mmol), PdCl$_2$(dppf).DCM (54.0 mg, 0.066 mmol) and Cs$_2$CO$_3$ (646 mg, 1.983 mmol) were added and the mixture heated in a microwave at 150° C. for 30 min. The reaction mixture was combined with the material (30 mg) from similar reaction. Water (20 mL) was added and the mixture extracted with ethyl acetate (3×15 mL). The organic layer was dried over MgSO$_4$, filtered and solvent removed in vacuo. Purification by chromatography on silica gel, eluting with a gradient of 0-50% ethyl acetate in cyclohexane, afforded the title compound (204.4 mg). LCMS (A) m/z: 291 [M+1]⁺, Rt 0.84 min (acidic).

Description 10

2,6-Dimethyl-3-phenylthieno[2,3-b]pyridin-4-amine

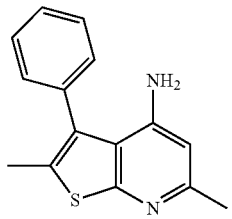

Following the general method as outlined in Description 9, starting from phenylboronic acid (71.1 mg, 0.583 mmol), the title compound was prepared (92 mg). LCMS (A) m/z: 256 [M+1]⁺, Rt 0.78 min (acidic).

Description 11

1,1-Dimethylethyl 4-[3-(4-amino-2,6-dimethylthieno[2,3-b]pyridin-3-yl)phenyl]-1-piperazinecarboxylate

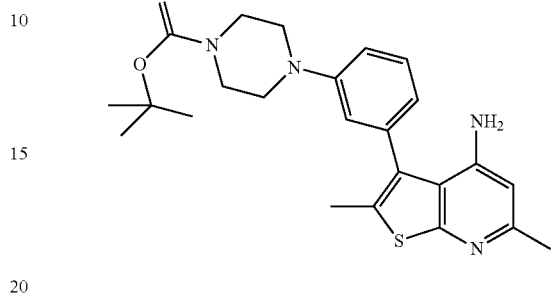

Under nitrogen, 3-bromo-2,6-dimethylthieno[2,3-b]pyridin-4-amine (130 mg, 0.506 mmol) (Description 8) was dissolved in 1,4-dioxane (3 mL) and water (1 mL) and 1,1-dimethylethyl 4-[3-(4,4,5,5-tetramethyl-1,3,2-dioxaborolan-2-yl)phenyl]-1-piperazinecarboxylate (294 mg, 0.758 mmol), tetrakis(triphenylphosphine)palladium(0) (58.4 mg, 0.051 mmol) and potassium carbonate (210 mg, 1.517 mmol) were added. The mixture was then heated in a microwave at 120° C. for 30 min. Ethyl acetate (10 mL) was added and the mixture washed with water (2×5 mL). The organic layer was dried over MgSO$_4$, filtered and solvent removed in vacuo. Purification by chromatography on silica gel, eluting with a gradient of 0-70% ethyl acetate in cyclohexane, afforded the title compound (197 mg). LCMS (A) m/z: 439 [M+1]⁺, Rt 0.99 min (acidic).

Description 12

{1-[3-(Methyloxy)phenyl]ethylidene}propanedinitrile

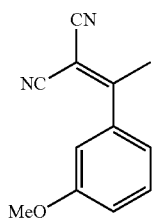

To a stirred solution of acetic acid (60 mL) was added hexamethyldisilazane (26.2 mL, 125 mmol) dropwise over 30 min with temperature kept below 40° C. throughout addition. This resulting solution was subsequently added to a stirred solution of malononitrile (13.50 g, 204 mmol) and 3-methoxyacetophenone (13.71 mL, 100 mmol) in acetic acid (30 mL). The final reaction mixture heated to 70° C. under nitrogen for 16 h. The reaction mixture was cooled to RT, partitioned between toluene and water (150 mL each). The aqueous layer was separated and re-extracted with toluene (2×60 mL). The combined organic layer was dried over Na$_2$SO$_4$ and solvent removed in vacuo, to afford the title compound (20 g). LCMS (A) m/z: 199 [M+1]⁺, Rt 1.20 min (acidic).

Description 13

2-Amino-4-[3-(methyloxy)phenyl]-3-thiophenecarbonitrile

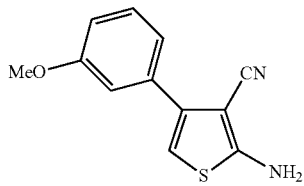 [SMILES: COc1cccc(-c2csc(N)c2C#N)c1]

To a stirred suspension of {1-[3-(methyloxy)phenyl]ethylidene}propanedinitrile (20 g, 101 mmol) (Description 12) and sulfur (3.88 g, 121 mmol) in THF (100 mL) at 35° C. was added NaHCO₃ (9.32 g, 111 mmol) pre-dissolved in water (80 mL). The resulting mixture was stirred at 35° C. under nitrogen for 45 min. Water (150 mL) was added and the mixture extracted with ethyl acetate (2×100 mL). The combined organic layer was dried over Na₂SO₄ and the solvent was removed in vacuo. The residue was triturated with diethyl ether, to afford the title compound (15 g). The supernatant liquid from the trituration was isolated and purified by chromatography on silica gel, eluting with a gradient of 0-40% ethyl acetate in cyclohexane, to afford an additional quantity of the title compound (6.7 g). LCMS (A) m/z: 231 [M+1]⁺, Rt 1.14 min (acidic).

Description 14

Ethyl 4-amino-6-methyl-3-[3-(methyloxy)phenyl]thieno[2,3-b]pyridine-5-carboxylate

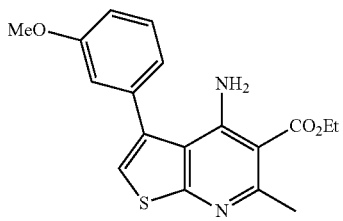 [SMILES: CCOC(=O)c1c(C)nc2scc(-c3cccc(OC)c3)c2c1N]

A mixture of 2-amino-4-[3-(methyloxy)phenyl]-3-thiophenecarbonitrile (1 g, 4.34 mmol) (Description 13), ethyl acetoacetate (0.550 mL, 4.34 mmol) and SnCl₄ (1.019 mL, 8.68 mmol) in toluene (25 mL) was stirred at RT for 30 min followed by reflux for 3 h. After cooling to RT, the mixture was quenched with 2M NaOH (50 mL) and extracted with ethyl acetate (3×40 mL). The combined organics were washed with brine (50 mL), dried and concentrated. Purification by chromatography on silica gel, eluting with a gradient of 0-50% ethyl acetate in cyclohexane, to give the title compound (915 mg). LCMS (A) m/z: 343 [M+1]⁺, Rt 1.25 min (acidic).

Description 15

Ethyl 4-amino-2-bromo-6-methyl-3-[3-(methyloxy)phenyl]thieno[2,3-b]pyridine-5-carboxylate

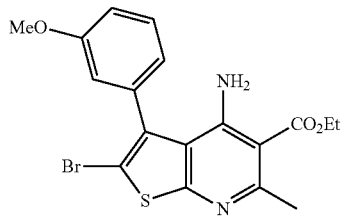

To a stirred solution of ethyl 4-amino-6-methyl-3-[3-(methyloxy)phenyl]thieno[2,3-b]pyridine-5-carboxylate (865 mg, 2.53 mmol) (Description 14) in DCM (18 mL), was added N-bromosuccinimide (540 mg, 3.03 mmol) and the resulting mixture stirred for 45 min at RT. The mixture was concentrated and purified by chromatography on silica gel, eluting with a gradient of 0-20% ethyl acetate in cyclohexane, to give the title compound (1.02 g). LCMS (A) m/z: 421/423 [M+1]⁺, Rt 1.57 min (acidic).

Description 16

4-Amino-2-bromo-6-methyl-3-[3-(methyloxy)phenyl]thieno[2,3-b]pyridine-5-carboxylic acid

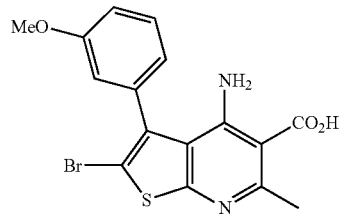 [SMILES: CCOC(=O)c1c(C)nc2sc(Br)c(-c3cccc(OC)c3)c2c1N]

A mixture of ethyl 4-amino-2-bromo-6-methyl-3-[3-(methyloxy)phenyl]thieno[2,3-b]pyridine-5-carboxylate (700 mg, 1.661 mmol) (Description 15) in DMSO (7 mL) and aqueous NaOH (2M) (4.15 mL, 8.31 mmol) was heated at 150° C. for 1 h. The mixture was cooled to RT, diluted with water (20 mL) and acidified with formic acid to pH 6. The mixture was then extracted with ethyl acetate (5×30 mL) and the combined organics washed with brine (2×30 mL), dried and concentrated, to give the title compound (513 mg). LCMS (A) m/z: 393/395 [M+1]⁺, Rt 1.04 min (acidic).

Description 17

2-Bromo-6-methyl-3-[3-(methyloxy)phenyl]thieno[2,3-b]pyridin-4-amine

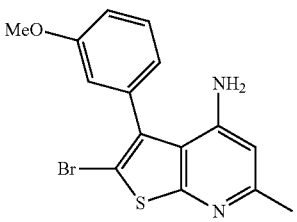 [SMILES: COc1cccc(-c2c(Br)sc3nc(C)cc(N)c23)c1]

A mixture of 4-amino-2-bromo-6-methyl-3-[3-(methyloxy)phenyl]thieno[2,3-b]pyridine-5-carboxylic acid (400 mg, 1.017 mmol) (Description 16), copper (194 mg, 3.05 mmol) and quinoline (3 mL, 25.3 mmol) was heated in a microwave at 180° C. for 30 min and then 190° C. for 30 min. After cooling to RT, the mixture was purified by chromatography on silica gel, eluting with a gradient of 40-60% ethyl acetate in cyclohexane, to give the title compound (214 mg). LCMS (A) m/z: 349/351 [M+1]⁺, Rt 1.08 min (acidic).

Alternatively, 4-amino-2-bromo-6-methyl-3-[3-(methyloxy)-phenyl]thieno-[2,3-b]pyridine-5-carboxylic acid (856 mg, 2.177 mmol) (Description 16) in diphenyl ether (8 mL, 50.3 mmol) was heated at 200° C. for 4.5 h and stand at RT overnight for 16 h. The mixture was purified by chromatography on silica gel, eluting with a gradient of 0-100% ethyl acetate in cyclohexane, to give the title compound (471 mg).

Description 18

3-Methyl-1-[3-(methyloxy)phenyl]-1-butanone

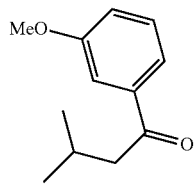

To a stirred solution of 3-(methyloxy)benzaldehyde (4.77 g, 35 mmol) in diethyl ether (100 mL) at 0° C. was added bromo(2-methylpropyl)magnesium (21 mL, 42 mmol). The solution was stirred for 10 min at 0° C. and then worked-up with 0.6M HCl (150 mL) and ethyl acetate (200 mL), to afford a crude material. In another round bottom flask of oxalyl chloride (4.60 mL, 52.5 mmol) in DCM (150 mL) at −78° C. was added DMSO (4.97 mL, 70.0 mmol), dissolved in dry DCM (20 mL), followed by a solution of the above crude material dissolved in dry DCM (25 mL). The resulting mixture was stirred for 1 h at −78° C., then triethylamine (24.39 mL, 175 mmol) was added and the solution stirred at −78° C. for 1 h. The reaction was quenched at −78° C. and the product was extracted by DCM and washed with water/brine. The crude material was purified by chromatography on silica gel, eluting with a gradient of 0-50% ethyl acetate in hexane, to afford the title compound (4.12 g). LCMS (B) m/z: 193 [M+1]⁺, Rt 3.11 min.

Description 19

{3-Methyl-1-[3-(methyloxy)phenyl]butylidene}propanedinitrile

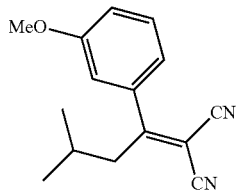 [SMILES: COc1cccc(C(CC(C)C)=C(C#N)C#N)c1]

To a stirred solution of acetic acid (14.36 mL, 251 mmol), was added hexamethyldisilazane (7.01 mL, 33.5 mmol) dropwise. The resulting solution was added to a solution of 3-methyl-1-[3-(methyloxy)phenyl]-1-butanone (4.02 g, 20.91 mmol) (Description 18) and malononitrile (2.76 g, 41.8 mmol) in acetic acid (15 mL). The mixture was stirred for 7 h at 70° C. The solution was cooled to RT and partitioned between toluene (167 mL) and water (130 mL). The aqueous layer was further extracted with toluene (70 mL). The combined organic layers were concentrated, and purified by chromatography on silica gel, eluting with DCM, to afford the title compound (4.42 g). LCMS (B) m/z: 241 [M+1]⁺, Rt 3.14 min.

Description 20

2-Amino-5-(1-methylethyl)-4-[3-(methyloxy)phenyl]-3-thiophenecarbonitrile

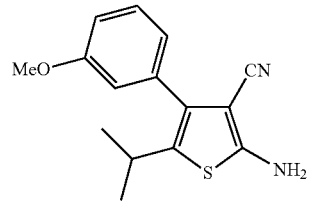 [SMILES: COc1cccc(-c2c(C(C)C)sc(N)c2C#N)c1]

To a stirred suspension of {3-methyl-1-[3-(methyloxy)phenyl]butylidene}propanedinitrile (4.4 g, 18.31 mmol) (Description 19) and sulfur (0.705 g, 21.97 mmol) in THF (30 mL) at 35° C. was added NaHCO₃ (1.846 g, 21.97 mmol) in water (15 mL), slowly. The resulting mixture was stirred overnight at 60° C. Water (60 mL) was added and the product extracted with ethyl acetate (2×100 mL). The crude material was triturated by diethyl ether (2×50 mL), to afford the title compound (4.32 g). LCMS (B) m/z: 273 [M+1]⁺, Rt 3.04 min.

Description 21

6-Methyl-2-(1-methylethyl)-3-[3-(methyloxy)phenyl]thieno[2,3-b]pyridin-4-amine

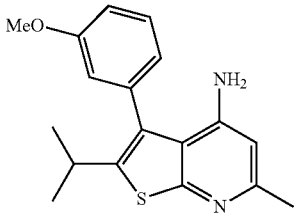 [SMILES: COc1cccc(-c2c(C(C)C)sc3nc(C)cc(N)c23)c1]

Following general method outlined in Description 4, starting from 2-amino-5-(1-methylethyl)-4-[3-(methyloxy)phenyl]-3-thiophenecarbonitrile (1089 mg, 4.0 mmol) (Description 20), the title compound (611 mg) was isolated. LCMS (B) m/z: 313 [M+1]⁺, Rt 2.20 min.

Description 22

{1-[3,4-Bis(methyloxy)phenyl]ethylidene}propanedinitrile

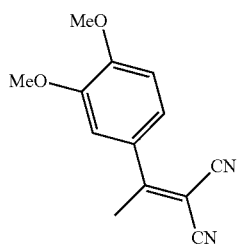 [SMILES: COc1ccc(C(C)=C(C#N)C#N)cc1OC]

Following general method outlined in Description 19, starting from 3,4-dimethoxyacetophenone (1.8 g, 9.99 mmol), the title compound (2.2 g) was isolated. LCMS (B) m/z: 229 [M+1]⁺, Rt 2.68 min.

Description 23

2-Amino-4-[3,4-bis(methyloxy)phenyl]-3-thiophenecarbonitrile

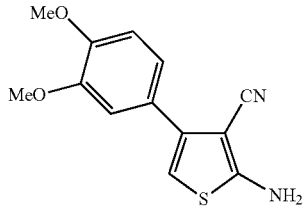 [SMILES: COc1ccc(-c2csc(N)c2C#N)cc1OC]

Following general method outlined in Description 20, starting from {1-[3,4-bis(methyloxy)phenyl]ethylidene}propanedinitrile (1.8 g, 7.89 mmol) (Description 22), the title compound (1.5 g) was isolated. LCMS (B) m/z: 261 [M+1]⁺, Rt 2.49 min.

Description 24

3-[3,4-Bis(methyloxy)phenyl]-6-methylthieno[2,3-b]pyridin-4-amine

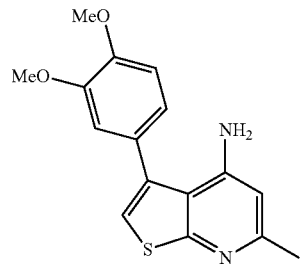 [SMILES: COc1ccc(-c2csc3nc(C)cc(N)c23)cc1OC]

Following general method outlined in Description 4, starting from 2-amino-4-[3,4-bis(methyloxy)phenyl]-3-thiophenecarbonitrile (1041 mg, 4.0 mmol) (Description 23), the title compound (246 mg) was isolated. LCMS (B) m/z: 301 [M+1]⁺, Rt 1.85 min.

Description 25

N-Methyl-N-(methyloxy)butanamide

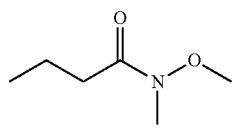

To a stirred solution of butanoyl chloride (5.33 g, 50 mmol) and N,O-dimethylhydroxylamine (5.36 g, 55.0 mmol) in DCM (100 mL) at 0° C., was added dropwise pyridine (8.90 mL, 110 mmol). The resulting mixture was stirred for 1.5 h at RT, followed by work-up using aqueous HCl (2.0M) (100 mL) and DCM (200 mL), to afford the title compound (6.02 g) which was carried over to next step without further purification. LCMS (B) m/z: 132 [M+1]⁺, Rt 1.74 min.

Description 26

1-[3-(Dimethylamino)phenyl]-1-butanone

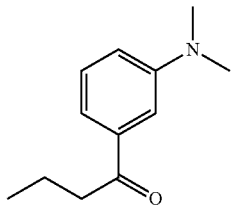

To a stirred solution of (3-bromophenyl)dimethylamine (7.5 g, 37.5 mmol) in THF (50 mL) at −78° C., was added n-butyllithium (2.88 g, 45.0 mmol). The resulting solution was stirred at −35° C. for 1 h and was then cooled to −78° C. and treated dropwise with a solution of N-methyl-N-(methyloxy)butanamide (4.92 g, 37.5 mmol) (Description 25) in dry THF (15 mL). The resulting mixture was stirred for 45 min at −78° C. and then worked up using water (100 mL) and ethyl acetate (200 mL). The crude material was purified by chromatography on silica gel, eluting with a gradient of 0-20% ethyl acetate in hexane, to afford the title compound (3.48 g). LCMS (B) m/z: 192 [M+1]⁺, Rt 2.29 min.

Description 27

{1-[3-(Dimethylamino)phenyl]butylidene}propanedinitrile

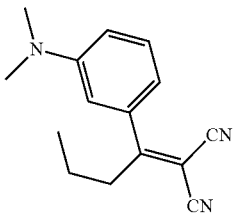 [SMILES: CCCC(=C(C#N)C#N)c1cccc(N(C)C)c1]

Following general method outlined in Description 19, starting from 1-[3-(dimethylamino)phenyl]-1-butanone (3.6 g, 18.82 mmol) (Description 26), the title compound (2.9 g) was isolated. LCMS (B) m/z: 240 [M+1]⁺, Rt 2.83 min.

Description 28

2-Amino-4-[3-(dimethylamino)phenyl]-5-ethyl-3-thiophenecarbonitrile

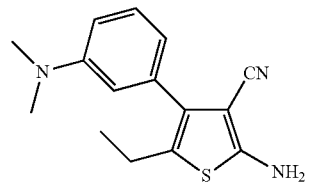 [SMILES: CCc1sc(N)c(C#N)c1-c1cccc(N(C)C)c1]

Following general method outlined in Description 20, starting from {1-[3-(dimethylamino)phenyl]butylidene}propanedinitrile (2.4 g, 10.03 mmol) (Description 27), the title compound (1.89 g) was isolated. LCMS (B) m/z: 272 [M+1]⁺, Rt 2.15 min.

Description 29

3-[3-(Dimethylamino)phenyl]-2-ethyl-6-methylthieno[2,3-b]pyridin-4-amine

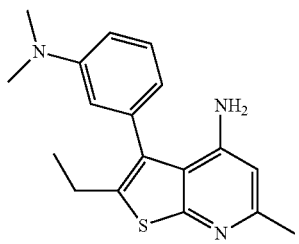

Following general method outlined in Description 4, starting from 2-amino-4-[3-(dimethylamino)phenyl]-5-ethyl-3-thiophenecarbonitrile (1.8 g, 6.63 mmol) (Description 28), the title compound (842 mg) was isolated. LCMS (B) m/z: 312 [M+1]⁺, Rt 1.89 min.

Description 30

Ethyl 4-amino-3,6-dimethylthieno[2,3-b]pyridine-5-carboxylate

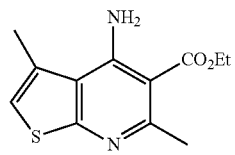 [SMILES: CCOC(=O)c1c(C)nc2scc(C)c2c1N]

A mixture of 2-amino-4-methyl-3-thiophenecarbonitrile (300 mg, 2.171 mmol), ethyl acetoacetate (0.275 mL, 2.171 mmol) and SnCl₄ (0.510 mL, 434 mmol) in toluene (15 mL) was stirred at RT for 30 min and then reflux for 3.5 h. After cooling to RT, the mixture was quenched with 6M NaOH (20 mL) and extracted with ethyl acetate (3×20 mL). The combined organics were washed with brine (30 mL), dried and concentrated. Purification by chromatography on silica gel, eluting with a gradient of 0-50% ethyl acetate in cyclohexane, afforded the title compound (210 mg). LCMS (A) m/z: 251 [M+1]⁺, Rt 0.77 min (acidic).

Description 31

Ethyl 4-amino-2-bromo-3,6-dimethylthieno[2,3-b]pyridine-5-carboxylate

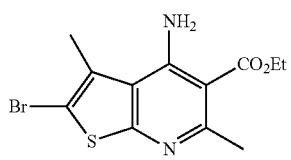 [SMILES: CCOC(=O)c1c(C)nc2sc(Br)c(C)c2c1N]

To a stirred solution of ethyl 4-amino-3,6-dimethylthieno[2,3-b]pyridine-5-carboxylate (210 mg, 0.839 mmol) (Description 30) in DCM (4 mL), was added N-bromosuccinimide (164 mg, 0.923 mmol) and the resulting mixture stirred for 20 min at RT. The mixture was concentrated and purified by chromatography on silica gel, eluting with a gradient of 0-50% ethyl acetate in cyclohexane, to afford the title compound (261 mg). LCMS (A) m/z: 329/331 [M+1]⁺, Rt 1.20 min (acidic).

Description 32

Ethyl 4-amino-3,6-dimethyl-2-(3-pyridinyl)thieno[2,3-b]pyridine-5-carboxylate

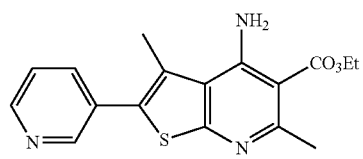

A mixture of ethyl 4-amino-2-bromo-3,6-dimethylthieno[2,3-b]pyridine-5-carboxylate (260 mg, 0.790 mmol) (Description 31), tetrakis(triphenylphosphine)palladium(0) (45.6 mg, 0.039 mmol), sodium carbonate (167 mg, 1.580 mmol) and 3-pyridineboronic acid (116 mg, 0.948 mmol) in acetonitrile (3 mL) and water (0.75 µl) was heated at 70° C. under nitrogen, for 30 min. 1,2-Dimethoxyethane (2 mL) was added and the mixture was stirred at 80° C. for 18 h. The reaction mixture was cooled to RT and concentrated. Purification by chromatography on silica gel, eluting with a gradient of 0-50% ethyl acetate in DCM, afforded the title compound (141 mg). LCMS (A) m/z: 328 [M+1]⁺, Rt 0.88 min (acidic), Rt 1.14 min (basic).

Description 33

4-Amino-3,6-dimethyl-2-(3-pyridinyl)thieno[2,3-b]pyridine-5-carboxylic acid

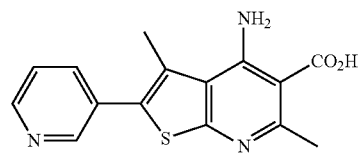 [SMILES: Cc1nc2sc(-c3cccnc3)c(C)c2c(N)c1C(=O)O]

A mixture of ethyl 4-amino-3,6-dimethyl-2-(3-pyridinyl)thieno[2,3-b]pyridine-5-carboxylate (120 mg, 0.367 mmol) (Description 32) in DMSO (3 mL) and 2M NaOH (0.916 mL, 1.833 mmol) was heated at 120° C. for 1 h. After cooling to RT, the mixture was diluted with water (20 mL), acidified with acetic acid to pH 6. The mixture was extracted with 10% MeOH in DCM (5×30 mL). The combined organics were dried and concentrated. The residue was passed through a C18 solid phase extractor cartridge, eluted with water (4×30 mL) followed by MeOH (4×30 mL). The combined organics were concentrated and dried at 55° C. in a vacuum oven, to afford the title compound (98 mg). LCMS (A) m/z: 300 [M+1]⁺, Rt 0.58 min (acidic).

Description 34

3,6-Dimethyl-2-(3-pyridinyl)thieno[2,3-b]pyridin-4-amine

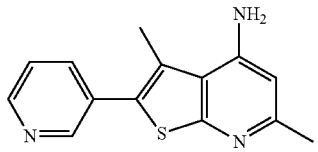 [SMILES: Cc1cc(N)c2c(C)c(-c3cccnc3)sc2n1]

A mixture of 4-amino-3,6-dimethyl-2-(3-pyridinyl)thieno[2,3-b]pyridine-5-carboxylic acid (98 mg, 0.327 mmol) (Description 33) and diphenyl ether (2 mL) was heated at 200° C. for 2.5 h. After cooling to RT, the mixture was purified by chromatography on silica gel, eluting with a gradient of 0-100% ethyl acetate in cyclohexane then followed by 10% MeOH in DCM, to afford the title compound (45 mg). LCMS (A) m/z: 256 [M+1]$^+$, Rt 0.61 min (acidic).

Description 35

Methyl 4-amino-2-methyl-3-[3-(methyloxy)phenyl]-6-oxo-6,7-dihydrothieno[2,3-b]pyridine-5-carboxylate

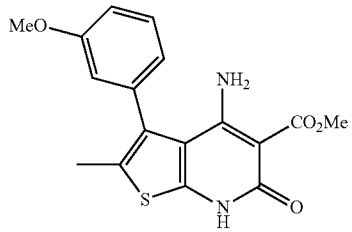 [SMILES: COC(=O)c1c(N)c2c(-c3cccc(OC)c3)c(C)sc2[nH]c1=O]

To a solution of 2-amino-5-methyl-4-[3-(methyloxy)phenyl]-3-thiophene carbonitrile (Description 3) (2.80 g, 11.46 mmol) in toluene (75 mL) was added dimethyl malonate (1.31 mL, 11.46 mmol) and SnCl$_4$ (2.68 mL, 22.92 mmol). The reaction mixture was then refluxed under nitrogen for ca. 2 h. The reaction mixture was then cooled to RT and concentrated in vacuo. The residue was partitioned between water and ethyl acetate (ca. 150 mL each) and the organic layer separated and washed with water (ca. 100 mL). The combined aqueous layer was re-extracted with ethyl acetate (ca. 100 mL). All organic layers were combined and passed through a phase separator and the mixture concentrated in vacuo. The residue was purified by normal phase chromatography, eluting with a gradient of 0-60% ethyl acetate in DCM followed by 0-20% MeOH in DCM, to afford the title compound (1.62 g). LCMS (A) m/z: 343 [M−1]$^-$, Rt 1.18 min (acidic).

Description 36

4-Amino-2-methyl-3-[3-(methyloxy)phenyl]thieno[2,3-b]pyridin-6(7H)-one

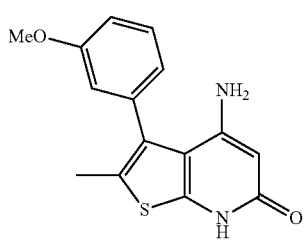 [SMILES: COc1cccc(-c2c(C)sc3[nH]c(=O)cc(N)c23)c1]

To a stirred suspension of methyl 4-amino-2-methyl-3-[3-(methyloxy)phenyl]-6-oxo-6,7-dihydrothieno[2,3-b]pyridine-5-carboxylate (Description 35) (1.617 g, 4.70 mmol) in ethanol (20 mL) was added aqueous NaOH (5M) (4.70 mL, 23.48 mmol). The suspension was then refluxed under nitrogen for ca. 2 h. The reaction mixture was then cooled to RT and concentrated in vacuo. The residue was partitioned between DCM and water (ca. 50 mL each) and acidified to ca. pH 7 using aqueous HCl (5M). The aqueous layer was separated and re-extracted with DCM (ca. 50 mL×2) and the combined organic layer passed through a phase separator and concentrated in vacuo. The residue was dissolved in diphenyl ether (20 mL, 126 mmol) and heated to 200° C. under nitrogen atmosphere for ca. 2 h. The mixture was then cooled to RT, passed through SCX cartridge (eluting with MeOH followed by 2M NH$_3$ MeOH) and the basic fractions combined and concentrated in vacuo. The residue was purified by normal phase chromatography, eluting with a gradient of 0-20% MeOH in DCM, to afford the title compound (588 mg). LCMS (A) m/z: 285 [M−1]$^-$, Rt 1.10 min (acidic).

Description 37

2-Methyl-6-(methyloxy)-3-[3-(methyloxy)phenyl]thieno[2,3-b]pyridin-4-amine

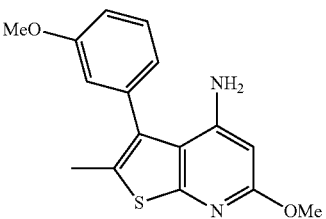 [SMILES: COc1cccc(-c2c(C)sc3nc(OC)cc(N)c23)c1]

To a suspension of 4-amino-2-methyl-3-[3-(methyloxy)phenyl]thieno[2,3-b]pyridin-6(7H)-one (Description 36) (120 mg, 0.419 mmol) in DMF (3 mL) was added potassium carbonate (116 mg, 0.838 mmol) and methyl iodide (0.029 mL, 0.461 mmol). The suspension was then heated to 90° C. under nitrogen atmosphere for ca. 2 h and then cooled to RT, quenched with water (ca. 25 mL) and extracted with ethyl acetate (ca. 25 mL×2). The combined organic layers were passed through a phase separator and solvent concentrated in vacuo. The residue was purified by normal phase chromatography, eluting with a gradient of 0-100% ethyl acetate in DCM followed by 0-20% MeOH in DCM, to afford the title compound (16.5 mg). LCMS (A) m/z: 301 [M+1]$^+$, Rt 1.21 min (acidic).

Description 38

Ethyl 2-cyano-3-[3-(methyloxy)phenyl]-2-butenoate

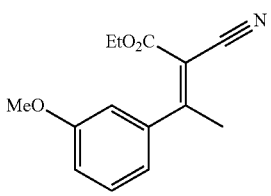 [SMILES: CCOC(=O)/C(C#N)=C(/C)c1cccc(OC)c1]

Hexamethyldisilazane (17.45 mL, 83 mmol) was added dropwise to acetic acid (38.1 mL, 666 mmol) (caution exothermic, maintain below 70° C.) stirred under an atmosphere of nitrogen. The resulting mixture was added to a solution of 1-[3-(methyloxy)phenyl]ethanone (9.14 mL, 66.6 mmol) and ethyl cyanoacetate (11.75 mL, 110 mmol) in acetic acid (16 mL), which was then stirred at 70° C. for 18 h. The mixture was then allowed to cool to RT and DCM (350 mL) and water (125 mL) were added. The organic layer was then separated and washed with additional water (125 mL) and dried with anhydrous MgSO$_4$, filtered and evaporated to dryness. The residue was purified on silica, eluting with a gradient of 0-30% ethyl acetate in isohexane and further purified on silica, eluting with a gradient of 0-25% ethyl acetate in isohexane, to afford the title compound (14.1 g). LCMS (A) m/z: 246 [M+1]$^+$, Rt 1.28 min (basic).

Description 39

Ethyl 2-amino-4-[3-(methyloxy)phenyl]-3-thiophenecarboxylate

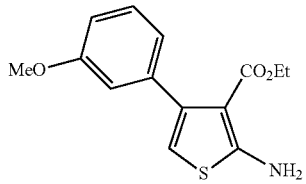 [SMILES: CCOC(=O)c1c(-c2cccc(OC)c2)csc1N]

A mixture of ethyl 2-cyano-3-[3-(methyloxy)phenyl]-2-butenoate (Description 38) (14.1 g, 57.5 mmol), sulfur (2.212 g, 69.0 mmol) and aqueous NaHCO$_3$ (2M) (31.6 mL, 63.2 mmol) in THF (57.5 mL) was stirred at 40° C. After 64 h the mixture was partitioned between water (200 mL) and ethyl acetate (300 mL). The aqueous phase was separated and extracted with additional ethyl acetate (200 mL). The organic extracts were combined, dried with anhydrous MgSO$_4$, filtered and evaporated to dryness. The residue was purified on silica, eluting with a gradient of 0-50% ethyl acetate in isohexane, to afford the title compound (12.6 g). LCMS (A) m/z: 278 [M+1]$^+$, Rt 1.30 min (basic).

Description 40

4-[3-(Methyloxy)phenyl]-2-thiophenamine

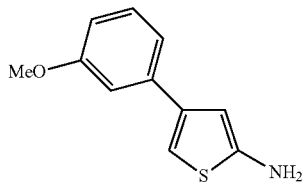 [SMILES: COc1cccc(-c2csc(N)c2)c1]

A mixture of ethyl 2-amino-4-[3-(methyloxy)phenyl]-3-thiophene carboxylate (Description 39) (5 g, 18.03 mmol) and 20% aqueous solution of potassium hydroxide (100 mL, 18.03 mmol) in ethanol (100 mL) was heated at 110° C. for 24 h. After cooling to RT the ethanol was removed under reduced pressure. The residue was poured into water (100 mL) and extracted with ethyl acetate (50 mL×3). The organic layers were combined, washed with brine (100 mL), dried over MgSO$_4$, filtered and evaporated in vacuo. The residue was purified by chromatography on silica, eluting with a gradient of 0-25% ethyl acetate in cyclohexane, to give the title compound (1.83 g). LCMS (A) m/z: 206 [M+1]$^+$, Rt 1.14 min (acidic).

Description 41

2,2-Dimethyl-5-[({4-[3-(methyloxy)phenyl]-2-thienyl}amino)methylidene]-1,3-dioxane-4,6-dione

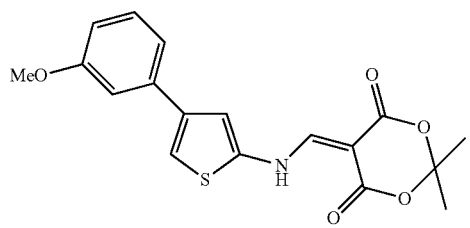 [SMILES: COc1cccc(-c2csc(NC=C3C(=O)OC(C)(C)OC3=O)c2)c1]

Meldrum's acid (1.58 g, 10.96 mmol) was dissolved in trimethyl orthoformate (24.23 mL, 219 mmol) and the mixture was heated at 110° C. for 1 h. After cooling to RT, 4-[3-(methyloxy)phenyl]-2-thiophenamine (Description 40) (1.5 g, 7.31 mmol) was added to the mixture and reheated at 90° C. for 15 h. After cooling to RT, the mixture was evaporated in vacuo. The residue was dissolved in DCM and treated with potassium carbonate (3.03 g, 21.92 mmol). After stirring for 30 min, the mixture was filtered and the filtrate was evaporated in vacuo, to give the title compound (1.24 g). LCMS (A) m/z: 360 [M+1]$^+$, Rt 1.19 min (acidic).

Description 42

3-[3-(Methyloxy)phenyl]thieno[2,3-b]pyridin-4(7H)-one

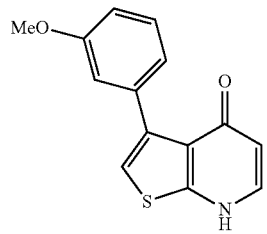 [SMILES: COc1cccc(-c2csc3[nH]ccc(=O)c23)c1]

A mixture of 2,2-dimethyl-5-[({4-[3-(methyloxy)phenyl]-2-thienyl}amino)methylidene]-1,3-dioxane-4,6-dione (Description 41) (1.2 g, 3.34 mmol) and diphenyl ether (15 mL, 94 mmol) was heated at 220° C. for 1 h. After cooling to RT, the mixture was purified by chromatography on silica, eluting with a gradient of 0-100% ethyl acetate in DCM, to give the title compound (487 mg). LCMS (A) m/z: 258 [M+1]$^+$, Rt 0.93 min (acidic).

Description 43

4-Chloro-3-[3-(methyloxy)phenyl]thieno[2,3-b]pyridine

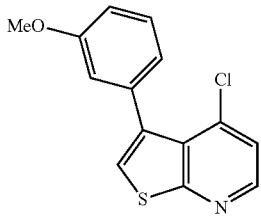 [SMILES: COc1cccc(-c2csc3nccc(Cl)c23)c1]

A mixture of 3-[3-(methyloxy)phenyl]thieno[2,3-b]pyridin-4(7H)-one (Description 42) (465 mg, 1.807 mmol) and phosphorus oxychloride (5 mL, 53.6 mmol) was heated at 110° C. for 1 h. After cooling to RT, the mixture was poured onto ice, stirred for 30 min and then extracted with DCM (10 mL×3). The organic layers were combined, washed with saturated $NaHCO_3$ solution (100 mL), brine (100 mL), filtered through phase separator and evaporated in vacuo. The residue was purified by chromatography on silica, eluting with a gradient of 0-40% ethyl acetate in cyclohexane, to give the title compound (424 mg). LCMS (A) m/z: 278 [M+1]$^+$, Rt 1.33 min (acidic).

Description 44

[1-(3-Bromophenyl)ethylidene]propanedinitrile

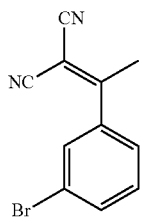

To a stirred solution of acetic acid (30 mL) at RT was added hexamethyldisilazane (13.09 mL, 62.8 mmol) dropwise over 10 min, maintaining temperature below 40° C. The resulting solution was then added dropwise to a solution of 1-(3-bromophenyl)ethanone (6.68 mL, 50.2 mmol) and malononitrile (6.33 mL, 100 mmol) in acetic acid (30 mL) and the mixture heated to 70° C. under nitrogen overnight. The reaction mixture cooled to RT and partitioned between water and toluene (ca. 150 mL each). The aqueous layer was separated and re-extracted with toluene (ca. 100 mL). The combined organic layer was dried over $MgSO_4$ and solvent removed in vacuo, to afford the title compound (12.7 g) which was carried over to next step without further purification. LCMS (A) m/z: 247/249 [M+1]$^+$, Rt 1.18 min (acidic).

Description 45

2-Amino-4-(3-bromophenyl)-3-thiophenecarbonitrile

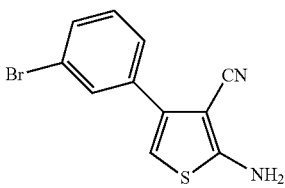 [SMILES: N#Cc1c(-c2cccc(Br)c2)csc1N]

To a stirred suspension of [1-(3-bromophenyl)ethylidene]propanedinitrile (Description 44) (12.98 g, 52.5 mmol) and sulfur (2.021 g, 63.0 mmol) in THF (60 mL) at 35° C. was added $NaHCO_3$ (5.30 g, 63.0 mmol) pre-dissolved in water (30 mL), and the resulting mixture was stirred for 1 h. Water (25 mL) was then added to the mixture, and the aqueous layer extracted with DCM (3×50 mL). The combined organic layers were dried with $Na_2SO_4$ and concentrated. The residue was purified by chromatography on silica, eluting with a gradient of 0-20% ethyl acetate in DCM, to afford the title compound (10.937 g). LCMS (A) m/z: 279/281 [M+1]$^+$, Rt 1.15 min (acidic).

Description 46

Ethyl 4-amino-3-(3-bromophenyl)-6-methylthieno[2,3-b]pyridine-5-carboxylate

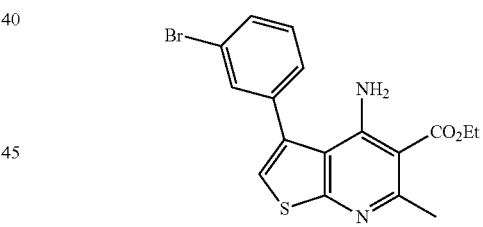

The reaction was carried out in two batches:

A mixture of 2-amino-4-(3-bromophenyl)-3-thiophenecarbonitrile (Description 45) (5.47 g, 19.59 mmol), ethyl acetoacetate (2.73 mL, 21.55 mmol) and $SnCl_4$ (4.60 mL, 39.2 mmol) in toluene (140 mL) was stirred under nitrogen at RT for 30 min, and then refluxed for 2 h. After cooling to RT, the solution was basified with 6M NaOH (ca. 50 mL) and diluted with 10% MeOH in DCM. The organic layer of the filtrate was separated and the aqueous layer re-extracted with 10% MeOH in DCM (70 mL×2). The combined organic layers were dried and concentrated. The residue was purified by chromatography on silica, eluting with a gradient of 0-20% ethyl acetate in DCM. At this point, the relevant fractions from both batches were combined, to give the title compound (6.31 g). LCMS (A) m/z: 391/393 [M+1]$^+$, Rt 1.24 min (acidic).

Description 47

Ethyl 4-amino-2-bromo-3-(3-bromophenyl)-6-methylthieno[2,3-b]pyridine-5-carboxylate

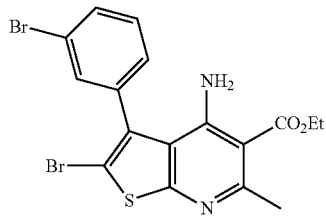 [SMILES: CCOC(=O)c1c(C)nc2sc(Br)c(-c3cccc(Br)c3)c2c1N]

To a solution of ethyl 4-amino-3-(3-bromophenyl)-6-methylthieno[2,3-b]pyridine-5-carboxylate (Description 46) (6.309 g, 16.12 mmol) in DCM (100 mL) was added N-bromosuccinimide (3.44 g, 19.35 mmol) at RT. The mixture was stirred for 3.5 h. The solvent was removed in vacuo. The crude residue was then purified by chromatography on silica, eluting with a gradient of 0-30% ethyl acetate in cyclohexane, to give the title compound (5.13 g). LCMS (A) m/z: 471 [M+1]$^+$, Rt 1.52 min (acidic).

Description 48

4-Amino-2-bromo-3-(3-bromophenyl)-6-methylthieno[2,3-b]pyridine-5-carboxylic acid

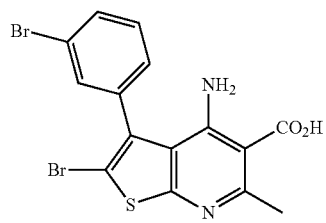

To a solution of ethyl 4-amino-2-bromo-3-(3-bromophenyl)-6-methylthieno[2,3-b]pyridine-5-carboxylate (Description 47) (2.566 g, 5.46 mmol) in DMSO (25 mL) was added aqueous NaOH (2M) (13.64 mL, 27.3 mmol). The mixture was then heated at 150° C. for 1 h. After cooling to RT, the solution was diluted with water (40 mL) and acidified (ca. pH 4-5) with formic acid. The aqueous layer was then extracted with ethyl acetate (50 mL×3), and the combined organic layers were dried and concentrated. Water (excess) was then added to the residue, and a white precipitate crashed-out. The solution was filtered and the precipitate was collected and left to dry overnight in the vacuum oven, to give the title compound (1.861 g). LCMS (A) m/z: 443 [M+1]$^+$, Rt 1.10 min (acidic).

Description 49

2-Bromo-3-(3-bromophenyl)-6-methylthieno[2,3-b]pyridin-4-amine

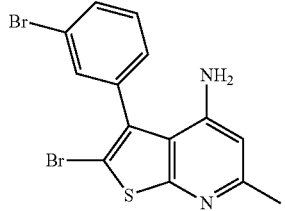 [SMILES: Cc1cc(N)c2c(-c3cccc(Br)c3)c(Br)sc2n1]

Diphenyl ether (20 mL, 126 mmol) was added to 4-amino-2-bromo-3-(3-bromophenyl)-6-methylthieno[2,3-b]pyridine-5-carboxylic acid (Description 48) (1.861 g, 4.21 mmol). The mixture was heated to 200° C. and stirred at 200° C. for 4 h. The mixture cooled to RT and was stirred overnight at RT. The mixture was then diluted with DCM and purified by chromatography on silica, eluting with a gradient of 0-40% ethyl acetate in cyclohexane, to give the title compound (1.0 g). LCMS (A) m/z: 399 [M+1]$^+$, Rt 0.94 min (acidic).

Description 50

N-[2-Bromo-3-(3-bromophenyl)-6-methylthieno[2,3-b]pyridin-4-yl]benzenesulfonamide

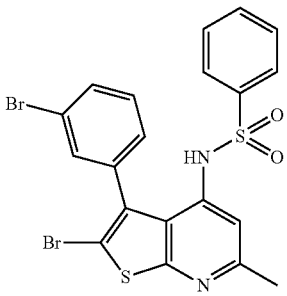 [SMILES: Cc1cc(NS(=O)(=O)c2ccccc2)c2c(-c3cccc(Br)c3)c(Br)sc2n1]

To a stirred solution of 2-bromo-3-(3-bromophenyl)-6-methylthieno[2,3-b]pyridin-4-amine (Description 49) (1 g, 2.51 mmol) in THF (10 mL) and DMF (5 mL) was added sodium tert-butoxide (0.603 g, 6.28 mmol) and benzenesulfonyl chloride (0.648 mL, 5.02 mmol). The reaction mixture stirred at RT under nitrogen for ca. 30 min. The reaction mixture was quenched with saturated ammonium chloride solution (ca. 30 mL) and extracted with DCM (25 mL×4). The combined organics were dried and concentrated. The residue was purified via normal phase chromatography eluted with a gradient of 0-50% ethyl acetate in DCM, to afford the title compound (1.12 g). LCMS (A) m/z: 539 [M+1]$^+$, Rt 1.45 min (acidic).

Description 51

N-{3-(3-Bromophenyl)-6-methyl-2-[1-({[2-(trimethylsilyl)ethyl]oxy}methyl)-1H-pyrazol-4-yl]thieno[2,3-b]pyridin-4-yl}-N-({[2-(trimethylsilyl)ethyl]oxy}methyl)benzenesulfonamide

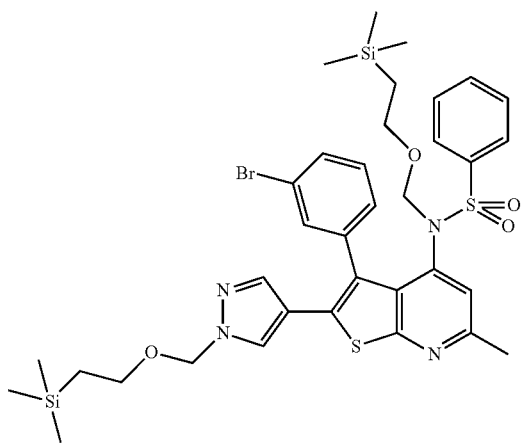 [SMILES: Cc1cc(N(COCC[Si](C)(C)C)S(=O)(=O)c2ccccc2)c2c(-c3cccc(Br)c3)c(-c3cnn(COCC[Si](C)(C)C)c3)sc2n1]

A mixture of N-[2-bromo-3-(3-bromophenyl)-6-methylthieno[2,3-b]pyridin-4-yl]benzene sulfonamide (Description 50) (600 mg, 1.115 mmol), 1-tert-butoxylcarbonyl-1H-pyrazole-4-boronic acid, pinacol ester (656 mg, 2.229 mmol), tetrakis(triphenylphosphine)palladium(0) (64.4 mg, 0.056 mmol) and potassium carbonate (462 mg, 3.34 mmol) in 1,4-dioxane (5 mL), DMF (2.5 mL) and water (1.25 mL) was heated in a microwave at 120° C. for 30 min. The reaction mixture was filtered through celite and the filtrate was concentrated. The residue was passed through an SCX cartridge, eluting with MeOH (ca. 125 mL) then with 2M $NH_3$ in MeOH (ca. 150 mL). The basic methanolic solution was concentrated and taken-up in DCM (8 mL). DIPEA (0.973 mL, 5.57 mmol) and SEMCl (0.593 mL, 3.34 mmol) were then added and the mixture stirred at RT for ca. 5 h. The reaction mixture was then quenched with $NaHCO_3$ (ca. 30 mL), extracted with DCM (25 mL×3) and the combined organics dried and concentrated. The residue was purified via normal phase chromatography eluted with 0-100% ethyl acetate in DCM, to give the title compound (485 mg). LCMS (A) m/z: 786/788 [M+1]$^+$, Rt 1.78 min (acidic).

Description 52

Ethyl 3-(3-bromophenyl)-4-{[(3-chlorophenyl)sulfonyl]amino}-6-methylthieno[2,3-b]pyridine-5-carboxylate

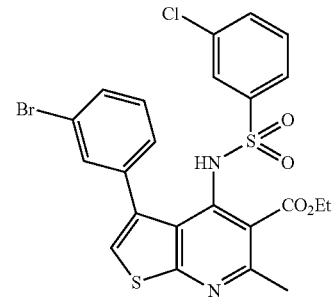 [SMILES: CCOC(=O)c1c(C)nc2scc(-c3cccc(Br)c3)c2c1NS(=O)(=O)c1cccc(Cl)c1]

To a stirred solution of ethyl 4-amino-3-(3-bromophenyl)-6-methylthieno[2,3-b]pyridine-5-carboxylate (Description 46) (2.87 g, 7.33 mmol) in THF (30 mL) and DMF (15 mL) was added sodium tert-butoxide (1.762 g, 18.34 mmol) and 3-chlorobenzenesulfonyl chloride (2.066 mL, 14.67 mmol). The reaction mixture was then stirred at RT under nitrogen for ca. 30 min and then quenched with saturated ammonium chloride solution (ca. 60 mL). The mixture was extracted with DCM (ca. 30 mL×5) and the combined organics dried and concentrated in vacuo. Purification by chromatography on silica, eluting with a gradient of 0-50% ethyl acetate in DCM afforded the title compound (1.48 g). LCMS (A) m/z: 566/568 [M+1]$^+$, Rt 1.47 min (acidic).

Description 53

N-[3-(3-Bromophenyl)-6-methylthieno[2,3-b]pyridin-4-yl]-3-chlorobenzenesulfonamide

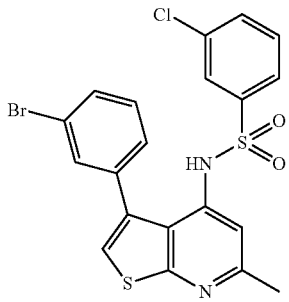

A mixture of ethyl 3-(3-bromophenyl)-4-{[(3-chlorophenyl)sulfonyl]amino}-6-methylthieno[2,3-b]pyridine-5-carboxylate (Description 52) (1.4 g, 2.474 mmol) in DMSO (25 mL) and aqueous NaOH (5M) (1.979 mL, 9.90 mmol) was heated at 150° C. for ca. 1 h. After cooling to RT, the mixture was diluted with water (20 mL) and acidified to ca. pH 4 with formic acid. The mixture was then extracted with ethyl acetate (30 mL×3) and the combined organics dried and concentrated. Water (30 mL) was added to the residue and a yellow precipitate crashed-out which was filtered and rinsed with water (15 mL×3). The yellow solid was dried and subsequently taken-up in diphenyl ether (15.74 mL, 99 mmol) and heated at 200° C. for ca. 1.5 h and then allowed to stand at RT overnight. The mixture was purified by chromatography on silica, eluting with a gradient of 0-100% ethyl acetate in cyclohexane followed by 10% MeOH in DCM, to give the title compound (820 mg). LCMS (A) m/z: 494/496 [M+1]$^+$, Rt 1.31 min (acidic).

Description 54

N-[3-(3-Bromophenyl)-6-methylthieno[2,3-b]pyridin-4-yl]-3-chloro-N-({[2-(trimethylsilyl)ethyl]oxy}methyl)benzenesulfonamide

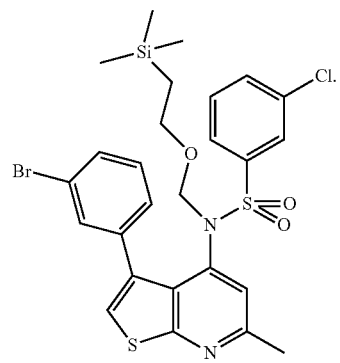 [SMILES: Cc1cc(N(COCC[Si](C)(C)C)S(=O)(=O)c2cccc(Cl)c2)c2c(-c3cccc(Br)c3)csc2n1]

To a stirred solution of N-[3-(3-bromophenyl)-6-methylthieno[2,3-b]pyridin-4-yl]-3-chlorobenzenesulfonamide (Description 53) (820 mg, 1.661 mmol) in DCM (10 mL) was added DIPEA (0.580 mL, 3.32 mmol) and SEMCl (0.442 mL, 2.491 mmol). The mixture was stirred at RT for ca. 1.5 h and then quenched with NaHCO₃ (ca. 30 mL) and extracted with DCM (25 mL×3). The combined organics were dried and concentrated and the residue purified via normal phase chromatography, eluting with 0-50% ethyl acetate in DCM, to give the title compound (960 mg). LCMS (A) m/z: 624/626 [M+1]⁺, Rt 1.59 min (acidic).

Description 55

[1-(3-Methylphenyl)ethylidene]propanedinitrile

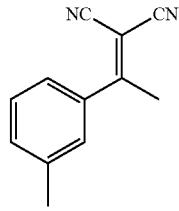

To a stirred solution of acetic acid (10 mL) was added dropwise hexamethyldisilazane (3.89 mL, 18.65 mmol) over ca. 30 min with the temperature kept below 40° C. throughout the addition. This resulting solution was subsequently added to a stirred solution of 1-(3-methylphenyl)ethanone (2.03 mL, 14.91 mmol) and malononitrile (1.88 mL, 29.8 mmol) in acetic acid (10 mL) and the mixture heated to 70° C. under nitrogen overnight. The reaction mixture was then cooled to RT, diluted with water (ca. 50 mL) and extracted with toluene (ca. 50 mL×2). The combined organic layer was passed through a phase separator and the solvent concentrated in vacuo, to give the title compound (2.89 g) which was used in next step without further purification. LCMS (A) m/z: 181 [M−1]⁻, Rt 1.23 min (acidic).

Description 56

2-Amino-4-(3-methylphenyl)-3-thiophenecarbonitrile

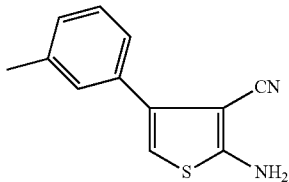

To a stirred suspension of [1-(3-methylphenyl)ethylidene]propanedinitrile (Description 55) (2.897 g, 15.90 mmol) and sulfur (0.612 g, 19.08 mmol) in THF (25 mL) at 35° C. was added NaHCO₃ (1.469 g, 17.49 mmol) pre-dissolved in water (25 mL). The reaction mixture was stirred at 35° C. under nitrogen atmosphere for ca. 1 h and then diluted with water (ca. 50 mL) and extracted with ethyl acetate (ca. 50 mL×2). The combined organic layer was passed through a phase separator and then solvent removed in vacuo. Purification by chromatography on silica, eluting with a gradient of 0-40% ethyl acetate in cyclohexane afforded the title compound (2.98 g). LCMS (A) m/z: 215 [M+1]⁺, Rt 1.19 min (acidic).

Description 57

Ethyl 4-amino-6-methyl-3-(3-methylphenyl)thieno[2,3-b]pyridine-5-carboxylate

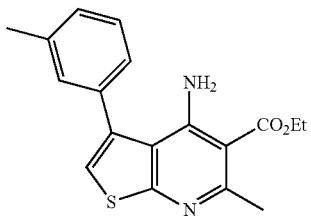 [SMILES: CCOC(=O)c1c(C)nc2scc(-c3cccc(C)c3)c2c1N]

To a stirred solution of 2-amino-4-(3-methylphenyl)-3-thiophenecarbonitrile (Description 56) (2.98 g, 13.91 mmol) in toluene (75 mL) at RT was added ethyl acetoacetate (1.76 mL, 13.91 mmol) and SnCl₄ (3.26 mL, 27.8 mmol). The reaction mixture was refluxed under a nitrogen atmosphere for ca. 4 h and was then cooled to RT and concentrated in vacuo. The residue was re-partitioned between ethyl acetate and water (ca. 80 mL each) and the aqueous layer separated and re-extracted with ethyl acetate (ca. 50 mL×2). The combined organic layer was then passed though a phase separator and the solvent removed in vacuo. The residue was purified by chromatography on silica, eluting with a gradient of 0-50% ethyl acetate in cyclohexane, to give the title compound (880 mg). LCMS (A) m/z: 327 [M+1]⁺, Rt 1.23 min (acidic).

Description 58

Ethyl 4-amino-2-bromo-6-methyl-3-(3-methylphenyl)thieno[2,3-b]pyridine-5-carboxylate

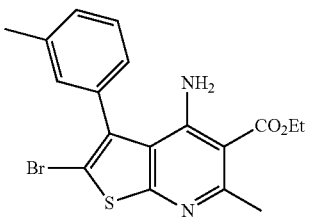 [SMILES: CCOC(=O)c1c(C)nc2sc(Br)c(-c3cccc(C)c3)c2c1N]

To a stirred solution of ethyl 4-amino-6-methyl-3-(3-methylphenyl)thieno[2,3-b]pyridine-5-carboxylate (Description 57) (880 mg, 2.70 mmol) in DCM (10 mL) at RT was added dropwise N-bromosuccinimide (528 mg, 2.97 mmol) pre-dissolved in DCM (15 mL). The reaction mixture stirred at RT under nitrogen atmosphere for ca. 1 h. The reaction mixture was then quenched with saturated NaHCO₃ aqueous solution and the aqueous layer separated and re-extracted with DCM (ca. 30 mL). The combined organic layer was then passed through a phase separator and the solvent removed in vacuo. Purification by chromatography on silica, eluting with a gradient of 0-40% ethyl acetate in cyclohexane afforded the title compound (900 mg). LCMS (A) m/z: 405/407 [M+1]⁺, Rt 1.55 min (acidic).

Description 59

2-Bromo-6-methyl-3-(3-methylphenyl)thieno[2,3-b]pyridin-4-amine

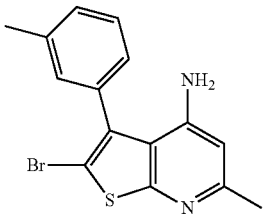

To a stirred solution of ethyl 4-amino-2-bromo-6-methyl-3-(3-methyl phenyl)thieno[2,3-b]pyridine-5-carboxylate (Description 58) (900 mg, 2.221 mmol) in ethanol (20 mL) at RT was added aqueous NaOH (5M) (1.0 mL, 5.0 mmol). The reaction mixture was heated to 90° C. for ca. 2 h. After cooling to RT the solvent was removed in vacuo. The residue was re-dissolved in water (ca. 80 mL) and neutralized to ca. pH 7 using aqueous HCl (5M). The solution was then extracted with 20% MeOH in DCM (ca. 50 mL×2). The combined organic layer was passed through a phase separator and the solvent removed in vacuo to give a residue which was subsequently re-dissolved in diphenyl ether (10 mL, 62.9 mmol) and heated to 200° C. for ca. 3 h. The reaction mixture was cooled to RT, passed through an SCX cartridge (eluting with MeOH/2M NH$_3$ MeOH). The basic fractions were combined and the solvent removed in vacuo, to give the title compound (487 mg). LCMS (A) m/z: 333/335 [M+1]$^+$, Rt 0.86 min (acidic).

Description 60

N-[2-Bromo-6-methyl-3-(3-methylphenyl)thieno[2,3-b]pyridin-4-yl]-3-chlorobenzenesulfonamide

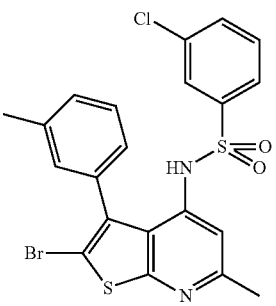 [SMILES: Cc1cccc(-c2c(Br)sc3nc(C)cc(NS(=O)(=O)c4cccc(Cl)c4)c23)c1]

To a stirred solution of 2-bromo-6-methyl-3-(3-methylphenyl)thieno[2,3-b]pyridin-4-amine (Description 59) (487 mg, 1.461 mmol) in THF (10 mL) at −78° C. under nitrogen atmosphere was added LiHMDS (1M solution in THF) (1.608 mL, 1.608 mmol) and 3-chlorobenzenesulfonyl chloride (0.226 mL, 1.608 mmol). The reaction mixture was warmed to RT under a nitrogen atmosphere for ca. 1 h and was then partitioned between ethyl acetate and water (ca. 30 mL each). The aqueous layer was separated and re-extracted with ethyl acetate (ca. 30 mL) and the combined organic layer passed through a phase separator and the solvent removed in vacuo. Purification by chromatography on silica, eluting with a gradient of 0-50% ethyl acetate in cyclohexane afforded the title compound (320 mg). LCMS (A) m/z: 508/510 [M+1]$^+$, Rt 1.60 min (acidic).

Description 61

4-Amino-2-bromo-3,6-dimethylthieno[2,3-b]pyridine-5-carboxylic acid

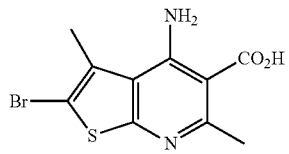 [SMILES: Cc1nc2sc(Br)c(C)c2c(N)c1C(=O)O]

To a solution of ethyl 4-amino-2-bromo-3,6-dimethylthieno[2,3-b]pyridine-5-carboxylate (Description 31) (857 mg, 2.60 mmol) in ethanol (25 mL) was added aqueous NaOH (2M) (2.60 mL, 5.21 mmol) and reaction mixture stirred at 100° C. for 4 h. The mixture was then cooled to RT before the solvent was removed in vacuo. The residue was then taken-up in water (20 mL) before acidifying with aqueous HCl (2M) (2 mL) to form a precipitate. The mixture was then subjected to a centrifuge and the aqueous solution was then decanted off and the solid residue dried under vacuum, to afford the title compound (720 mg). LCMS (A) m/z: 301/303 [M+1]$^+$, Rt 0.67 min (acidic).

Description 62

2-Bromo-3,6-dimethylthieno[2,3-b]pyridin-4-amine

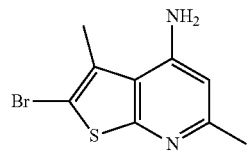

A mixture of 4-amino-2-bromo-3,6-dimethylthieno[2,3-b]pyridine-5-carboxylic acid (Description 61) (720 mg, 2.391 mmol) and diphenyl ether (3.80 mL, 23.91 mmol) was heated to 200° C. for 48 h. The mixture was then cooled to RT, taken-up in MeOH (10 mL) and purified on silica, eluting with a gradient of 0-20% 2M NH$_3$ in MeOH in DCM. Further purification by SCX, eluting with 0-100% 2M NH$_3$ in MeOH in MeOH afforded the title compound (350 mg). LCMS (A) m/z: 257/259 [M+1]$^+$, Rt 1.10 min (basic).

Description 63

Ethyl 2-bromo-4-{[(3-chlorophenyl)sulfonyl]amino}-3,6-dimethylthieno[2,3-b]pyridine-5-carboxylate

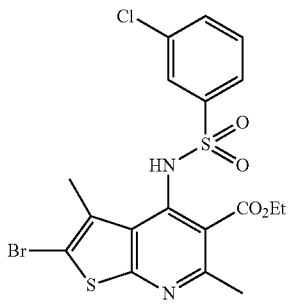 [SMILES: CCOC(=O)c1c(C)nc2sc(Br)c(C)c2c1NS(=O)(=O)c1cccc(Cl)c1]

To a stirred solution of ethyl 4-amino-2-bromo-3,6-dimethylthieno[2,3-b]pyridine-5-carboxylate (Description 31)

(500 mg, 1.519 mmol) in DMF (10 mL) was added sodium tert-butoxide (365 mg, 3.80 mmol) and 3-chlorobenzenesulfonyl chloride (0.428 mL, 3.04 mmol). The whole mixture was stirred at RT under nitrogen for ca. 1.5 h. The reaction mixture was then diluted with ethyl acetate (ca. 30 mL) and water (ca. 50 mL). The organic phase was separated and the aqueous phase re-extracted with ethyl acetate (ca. 30 mL×2). The combined organic phase was dried over $Na_2SO_4$ and the solvent concentrated in vacuo. The residue was purified by normal phase chromatography, eluting with a gradient of 0-50% ethyl acetate in cyclohexane, to give the title compound (350 mg). LCMS (A) m/z: 504/506 [M+1]$^+$, Rt 1.59 min (acidic).

Description 64

Ethyl 4-{[(3-chlorophenyl)sulfonyl]amino}-3,6-dimethyl-2-(1H-pyrazol-4-yl)thieno[2,3-b]pyridine-5-carboxylate

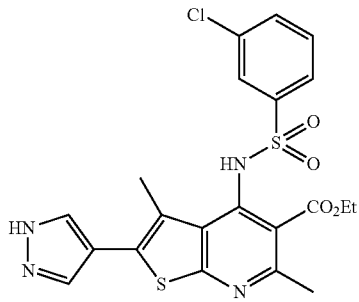 [SMILES: CCOC(=O)c1c(C)nc2sc(-c3cn[nH]c3)c(C)c2c1NS(=O)(=O)c1cccc(Cl)c1]

A mixture of ethyl 2-bromo-4-{[(3-chlorophenyl)sulfonyl]amino}-3,6-dimethylthieno[2,3-b]pyridine-5-carboxylate (Description 63) (350 mg, 0.695 mmol), 1-tert-butoxylcarbonyl-1H-pyrazole-4-boronic acid, pinacol ester (221 mg, 0.751 mmol), tetrakis(triphenylphosphine)palladium(0) (40.1 mg, 0.035 mmol) and potassium carbonate (288 mg, 2.084 mmol) in 1,4-dioxane (1.5 mL), DMF (1.5 mL) and water (0.5 mL) was heated at 100° C. overnight (ca. 16 h). The reaction mixture was cooled to RT, filtered through celite and the filtrate was concentrated. The residue was purified by normal phase chromatography, eluting with a gradient of 0-100% ethyl acetate in cyclohexane, to give the title compound (150 mg). LCMS (A) m/z: 491 [M+1]$^+$, Rt 1.20 min (acidic).

Description 65

Ethyl 4-amino-6-methylthieno[2,3-b]pyridine-5-carboxylate

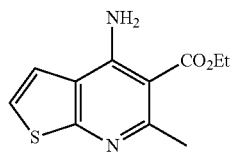 [SMILES: CCOC(=O)c1c(C)nc2sccc2c1N]

A mixture of 2-amino-3-thiophenecarbonitrile (2 g, 16.11 mmol), ethyl acetoacetate (2.24 mL, 17.72 mmol) and $SnCl_4$ (3.78 mL, 32.2 mmol) in toluene (120 mL) was stirred at RT for 30 min and then at reflux for ca. 4 h. After cooling to RT, the mixture was quenched with 6M NaOH (ca. 80 mL), diluted with ethyl acetate (80 mL) and then filtered through celite. The organic layer of the filtrate was separated and the aqueous layer was re-extracted with ethyl acetate (50 mL×5). The combined organics were dried and concentrated. Purification by chromatography on silica, eluting with a gradient of 0-50% ethyl acetate in cyclohexane, to give the title compound (960 mg). LCMS (A) m/z: 237 [M+1]$^+$, Rt 0.67 min (acidic).

Alternatively, a mixture of 2-amino-3-thiophenecarbonitrile (2.5 g, 20.13 mmol), ethyl 3-oxobutanoate (2.80 mL, 22.15 mmol) and $SnCl_4$ (4.73 mL, 40.3 mmol) in toluene (135 mL) was stirred at RT for 30 min, and then refluxed for 2 h. The mixture was then basified with 6M NaOH (ca. 25 mL), diluted with 10% MeOH in DCM (40 mL), and the mixture filtered through celite. The organic layer of the filtrate was then separated and the aqueous layer re-extracted with 10% MeOH in DCM (50 mL×3). The combined organic layers were dried and concentrated. The residue was then purified by chromatography on silica, eluting with a gradient of 0-10% ethyl acetate in DCM, to give the title compound. Another batch of 2-amino-3-thiophenecarbonitrile (2.5 g, 20.13 mmol) was subjected to the same procedure and the products from each reaction were combined to give the title compound (2.36 g).

Description 66

Ethyl 4-amino-2-bromo-6-methylthieno[2,3-b]pyridine-5-carboxylate

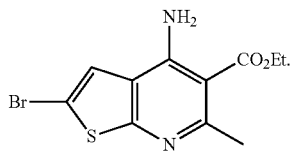

To a stirred solution of ethyl 4-amino-6-methylthieno[2,3-b]pyridine-5-carboxylate (Description 65) (1 g, 4.23 mmol) in acetic acid (3 mL) was added bromine (0.65 mL, 12.70 mmol) and the resulting mixture stirred at RT overnight (ca. 18 h). The reaction was quenched by pouring the reaction mixture into water and the aqueous solution was basified with NaOH (5M) and diluted with ethyl acetate (30 mL). The organic layer was separated and the aqueous layer was re-extracted with ethyl acetate (20 mL×3). The combined organics were washed with saturated sodium thiosulphate solution, dried and concentrated. Purification by chromatography on silica, eluting with a gradient of 0-30% ethyl acetate in DCM afforded the title compound (1.16 g). LCMS (A) m/z: 315/317 [M+1]$^+$, Rt 0.95 min (acidic).

Description 67

Ethyl 2-bromo-6-methyl-4-[(phenylsulfonyl)amino]thieno[2,3-b]pyridine-5-carboxylate

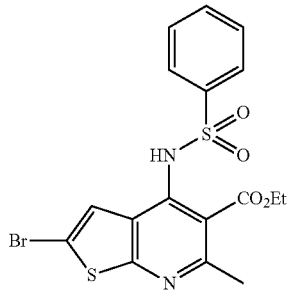 [SMILES: CCOC(=O)c1c(C)nc2sc(Br)cc2c1NS(=O)(=O)c1ccccc1]

To a stirring mixture of ethyl 4-amino-2-bromo-6-methylthieno[2,3-b]pyridine-5-carboxylate (Description 66) (5.84 g, 18.53 mmol) in THF (110 mL) and DMF (55 mL) was added sodium tert-butoxide (4.45 g, 46.3 mmol) and benzenesulfonyl chloride (4.75 mL, 37.1 mmol). The resulting mixture was stirred at RT for 30 min. The reaction mixture was quenched with saturated ammonium chloride solution (ca. 150 mL) and extracted with DCM (80 mL×3). The combined organic layers were dried and concentrated. The residue was purified via normal phase chromatography, eluting with 0-30% ethyl acetate in DCM, to give the title compound (6.27 g). LCMS (A) m/z: 455/457 [M+1]$^+$, Rt 1.35 min (acidic).

Description 68

Ethyl 6-methyl-4-[(phenylsulfonyl)amino]-2-(1H-pyrazol-4-yl)thieno[2,3-b]pyridine-5-carboxylate

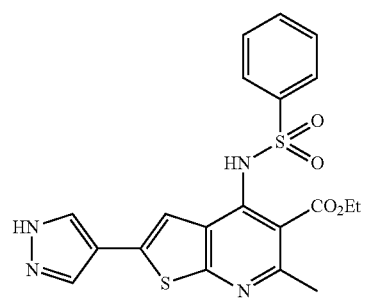 [SMILES: CCOC(=O)c1c(C)nc2sc(-c3cn[nH]c3)cc2c1NS(=O)(=O)c1ccccc1]

A mixture of ethyl 2-bromo-6-methyl-4-[(phenylsulfonyl)amino]thieno[2,3-b]pyridine-5-carboxylate (Description 67) (6.27 g, 13.77 mmol), 1-tert-butoxylcarbonyl-1H-pyrazole-4-boronic acid, pinacol ester (8.10 g, 27.5 mmol), tetrakis(triphenylphosphine)palladium(0) (0.796 g, 0.688 mmol) and potassium carbonate (5.71 g, 41.3 mmol) in 1,4-dioxane (40 mL), DMF (20 mL) and water (10 mL) was heated at 100° C. for ca. 3.5 h. After cooling to RT, the reaction mixture was filtered through celite and the filtrate was concentrated. The residue was purified via normal phase chromatography eluting with 0-100% ethyl acetate in DCM, to give the title compound (5.81 g). LCMS (A) m/z: 443 [M+1]$^+$, Rt 1.05 min (acidic).

Description 69

Ethyl 3-bromo-6-methyl-4-[(phenylsulfonyl)amino]-2-(1H-pyrazol-4-yl)thieno[2,3-b]pyridine-5-carboxylate

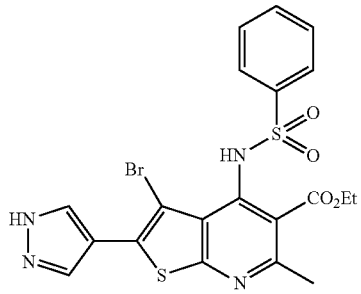 [SMILES: CCOC(=O)c1c(C)nc2sc(-c3cn[nH]c3)c(Br)c2c1NS(=O)(=O)c1ccccc1]

To a stirred solution of ethyl 6-methyl-4-[(phenylsulfonyl)amino]-2-(1H-pyrazol-4-yl)thieno[2,3-b]pyridine-5-carboxylate (Description 68) (5.8 g, 13.11 mmol) in CHCl$_3$ (160 mL) at 60° C. was added bromine (0.81 mL, 15.73 mmol), pre-diluted in CHCl$_3$ (36 mL), dropwise. The resulting mixture was stirred at 60° C. for ca. 1 h and then cooled to RT. The reaction mixture was then concentrated and the residue triturated with water (50 mL 3) and dried, to give the title compound (6.1 g). LCMS (A) m/z: 521/523 [M+1]$^+$, Rt 1.11 min (acidic).

Description 70

N-[3-Bromo-6-methyl-2-(1H-pyrazol-4-yl)thieno[2,3-b]pyridin-4-yl]benzenesulfonamide

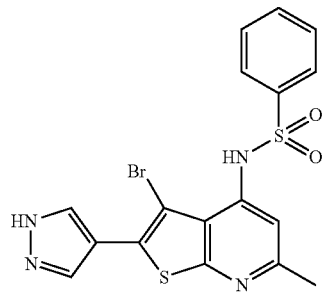 [SMILES: Cc1cc(NS(=O)(=O)c2ccccc2)c2c(Br)c(-c3cn[nH]c3)sc2n1]

A mixture of ethyl 3-bromo-6-methyl-4-[(phenylsulfonyl)amino]-2-(1H-pyrazol-4-yl)thieno[2,3-b]pyridine-5-carboxylate (Description 69) (6.1 g, 11.70 mmol) in DMSO (120 mL) and aqueous NaOH (5M) (9.36 mL, 46.8 mmol) was heated at 150° C. for ca. 2.5 h. After cooling to RT, the mixture was diluted with water (100 mL) and acidified with formic acid. The mixture was extracted with 20% MeOH in DCM (75 mL×5) and the combined organics dried and concentrated. Water (100 mL) was added to the residue and a precipitate crashed-out which was filtered and rinsed with water (50 mL×3). The solid was dried and then taken-up in diphenyl ether (74.4 mL, 468 mmol) and quinoline (13.86 mL, 117 mmol). The resulting mixture was then heated at 200° C. for ca. 5 h. After cooling to RT, the mixture was purified via normal phase chromatography, eluting with 0-100% ethyl acetate in DCM, to give the title compound (2.88 g). LCMS (A) m/z: 449/451 [M+1]+, Rt 1.05 min (acidic).

Description 71

1,1-Dimethylethyl 4-{3-bromo-6-methyl-4-[(phenyl-sulfonyl)amino]thieno[2,3-b]pyridin-2-yl}-1H-pyrazole-1-carboxylate

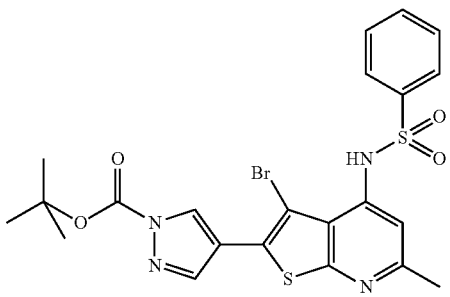 [SMILES: Cc1cc(NS(=O)(=O)c2ccccc2)c2c(Br)c(-c3cnn(C(=O)OC(C)(C)C)c3)sc2n1]

To a stirred solution of N-[3-bromo-6-methyl-2-(1H-pyrazol-4-yl)thieno[2,3-b]pyridin-4-yl]benzenesulfonamide (Description 70) (880 mg, 1.96 mmol) in acetonitrile (30 mL) was added Boc$_2$O (0.50 mL, 2.15 mmol), DMAP (96 mg, 0.78 mmol) and Et$_3$N (0.41 mL, 2.94 mmol) and the mixture stirred at RT for ca. 45 min. The mixture was then concentrated and taken-up in water (50 mL) and DCM (50 mL). The organic layer was separated and the aqueous was re-extracted with DCM (30 mL×2). The combined organics were dried and concentrated. The residue was purified via normal phase chromatography, eluting with 0-50% ethyl acetate in DCM, to give the title compound (1.03 g). LCMS (A) m/z: 549/551 [M+1]+, Rt 1.35 min (acidic).

Description 72

Ethyl 2-bromo-4-{[(3-chlorophenyl)sulfonyl] amino}-6-methylthieno[2,3-b]pyridine-5-carboxylate

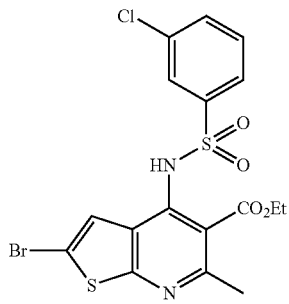 [SMILES: CCOC(=O)c1c(C)nc2sc(Br)cc2c1NS(=O)(=O)c1cccc(Cl)c1]

To a stirred solution of ethyl 4-amino-2-bromo-6-methylthieno[2,3-b]pyridine-5-carboxylate (Description 66) (390 mg, 1.24 mmol) in THF (12 mL) was added sodium tert-butoxide (297 mg, 3.09 mmol) and 3-chlorobenzenesulfonyl chloride (0.35 mL, 2.47 mmol). The reaction mixture was stirred at RT under nitrogen for ca. 3 h. The reaction mixture was diluted with ethyl acetate (ca. 30 mL) and water (ca. 50 mL). The organic layer was separated and the aqueous layer re-extracted with ethyl acetate (ca. 30 mL×2). The combined organic phase was dried over Na$_2$SO$_4$ and then concentrated in vacuo. Purification by chromatography on silica, eluting with a gradient of 0-20% ethyl acetate in DCM, afforded the title compound (252 mg). LCMS (A) m/z: 490/492 [M+1]+, Rt 1.48 min (acidic).

Alternatively, to a stirred solution of ethyl 4-amino-2-bromo-6-methylthieno[2,3-b]pyridine-5-carboxylate (Description 66) (3.76 g, 11.93 mmol) in THF (60 mL) and DMF (30 mL) was added sodium tert-butoxide (2.87 g, 29.8 mmol) and 3-chlorobenzenesulfonyl chloride (3.36 mL, 23.86 mmol). The reaction mixture was stirred at RT under nitrogen for ca. 30 min and was then diluted with water (ca. 30 mL) and concentrated in vacuo. The residue was purified by chromatography on silica, eluting with a gradient of 0-50% ethyl acetate/DCM, to afford the title compound (4.06 g). Alternatively, to a stirred solution of ethyl 4-amino-2-bromo-6-methylthieno[2,3-b]pyridine-5-carboxylate (Description 66) (7 g, 22.21 mmol) in THF (100 mL) and DMF (50 mL) was added sodium tert-butoxide (5.34 g, 55.5 mmol) and 3-chlorobenzenesulfonyl chloride (6.25 mL, 44.4 mmol). The reaction mixture was then stirred at RT under nitrogen for ca. 30 min. The reaction mixture was quenched with saturated NH$_4$Cl solution (ca. 200 mL) and extracted with DCM (ca. 80 mL×5). The combined organics were dried and concentrated in vacuo. The residue was purified by chromatography on silica, eluting with a gradient of 0-50% ethyl acetate in DCM, to afford material (8.24 g). 200 mg of the material was re-purified with a gradient of 0-30% ethyl acetate in DCM, to afford the title compound (115 mg).

Description 73

Ethyl 4-{[(3-chlorophenyl)sulfonyl]amino}-6-methyl-2-(1H-pyrazol-4-yl)thieno[2,3-b]pyridine-5-carboxylate

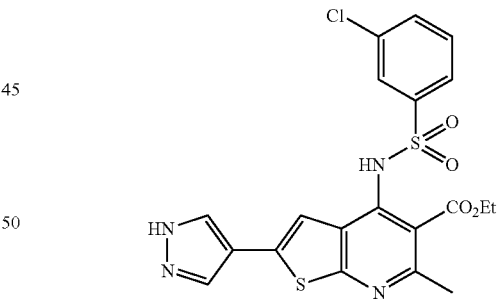

A mixture of ethyl 2-bromo-4-{[(3-chlorophenyl)sulfonyl]amino}-6-methylthieno[2,3-b]pyridine-5-carboxylate (Description 72) (402 mg, 0.82 mmol), 1-tert-butoxylcarbonyl-1H-pyrazole-4-boronic acid, pinacol ester (483 mg, 1.64 mmol) and tetrakis(triphenylphosphine)palladium(0) (47.4 mg, 0.041 mmol) and potassium carbonate (340 mg, 2.46 mmol) in 1,4-dioxane (3 mL), DMF (1.5 mL) and water (0.75 mL) was heated at 110° C. for ca. 2 h. After cooling to RT, the reaction mixture was filtered through celite and the filtrate was concentrated. Purification by chromatography on silica, eluting with a gradient of 0-100% ethyl acetate in DCM, afforded the title compound (355 mg). LCMS (A) m/z: 477 [M+1]+, Rt 1.18 min (acidic).

Alternatively, a mixture of ethyl 2-bromo-4-{[(3-chlorophenyl)sulfonyl]amino}-6-methylthieno[2,3-b]pyridine-5-carboxylate (Description 72) (6.91 g, 14.11 mmol), 1-tert-butoxylcarbonyl-1H-pyrazole-4-boronic acid, pinacol ester (6.22 g, 21.16 mmol), tetrakis(triphenylphosphine)palladium(0) (0.408 g, 0.353 mmol) and potassium carbonate (5.85 g, 42.3 mmol) in 1,4-dioxane (50 mL), DMF (25 mL) and water (12.5 mL) was heated at 100° C. overnight (ca. 20 h). After cooling to RT, the reaction mixture was filtered through celite and the filtrate was concentrated. The residue was purified by chromatography on silica, eluting with a gradient of 0-100% ethyl acetate/DCM. The resulting material was then passed through an SCX cartridge, eluting with MeOH (150 mL) followed by 2M $NH_3$ in MeOH (250 mL) and the basic methanolic fractions concentrated, to give the title compound (6.276 g).

Alternatively, a mixture of ethyl 2-bromo-4-{[(3-chlorophenyl)sulfonyl]amino}-6-methylthieno[2,3-b]pyridine-5-carboxylate (Description 72) (8 g, 16.33 mmol), 1-tert-butoxylcarbonyl-1H-pyrazole-4-boronic acid, pinacol ester (9.61 g, 32.7 mmol), tetrakis(triphenylphosphine)palladium(0) (0.944 g, 0.817 mmol) and potassium carbonate (6.77 g, 49.0 mmol) in 1,4-dioxane (50 mL), DMF (25 mL) and water (12.5 mL) was heated at 100° C. for ca. 3 h. After cooling to RT, the reaction mixture was filtered through celite and the filtrate was concentrated. The residue was purified by chromatography on silica, eluting with a gradient of 0-100% ethyl acetate in DCM. The resulting material was then passed through an SCX cartridge, eluting with MeOH (ca. 200 mL) followed by 2M $NH_3$ in MeOH (250 mL) and the basic methanolic fractions concentrated, to give the title compound (7.24 g). Some mixed fractions were further purified by MDAP (acidic conditions), to give the title compound (33 mg).

Description 74

Ethyl 3-bromo-4-{[(3-chlorophenyl)sulfonyl]amino}-6-methyl-2-(1H-pyrazol-4-yl)thieno[2,3-b]pyridine-5-carboxylate

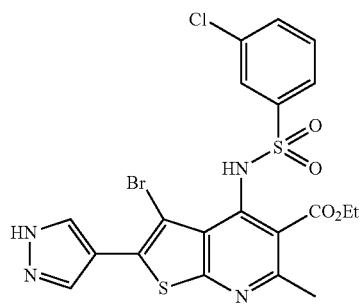 [SMILES: CCOC(=O)c1c(C)nc2sc(-c3cn[nH]c3)c(Br)c2c1NS(=O)(=O)c1cccc(Cl)c1]

To a stirred solution of ethyl 4-{[(3-chlorophenyl)sulfonyl]amino}-6-methyl-2-(1H-pyrazol-4-yl)thieno[2,3-b]pyridine-5-carboxylate (Description 73) (870 mg, 1.824 mmol) in $CHCl_3$ (30 mL) at 60° C. was added bromine (0.10 mL, 2.01 mmol), prediluted in $CHCl_3$ (5.25 mL), dropwise. The resulting mixture was stirred at 60° C. for ca. 4 h and was then cooled to RT. The resulting precipitate was filtered and the solid rinsed with DCM and dried, to give the title compound (920 mg). LCMS (A) m/z: 556/558 [M+1]$^+$, Rt 1.25 min (acidic).

Description 75

1,1-Dimethylethyl 4-(3-bromo-4-{[(3-chlorophenyl)sulfonyl]amino}-6-methylthieno[2,3-b]pyridin-2-yl)-1H-pyrazole-1-carboxylate

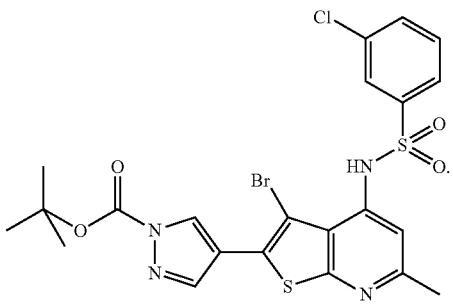 [SMILES: Cc1cc(NS(=O)(=O)c2cccc(Cl)c2)c2c(Br)c(-c3cnn(C(=O)OC(C)(C)C)c3)sc2n1]

To a stirred solution of N-[3-bromo-6-methyl-2-(1H-pyrazol-4-yl)thieno[2,3-b]pyridin-4-yl]-3-chlorobenzenesulfonamide (Example 100) (1.1 g, 2.27 mmol) in acetonitrile (40 mL) was added $Boc_2O$ (0.58 mL, 2.50 mmol), DMAP (111 mg, 0.91 mmol) and $Et_3N$ (0.47 mL, 3.41 mmol) and the mixture stirred at RT for ca. 1.5 h. The mixture was concentrated and then taken-up in water (50 mL) and DCM (40 mL). The organic layer was separated and the aqueous re-extracted with DCM (40 mL×2). The combined organics were dried and concentrated. Purification by chromatography on silica, eluting with a gradient of 0-50% ethyl acetate in DCM, afforded the title compound (1.3 g). LCMS (A) m/z: 584/586 [M+1]$^+$, Rt 1.42 min (acidic).

Description 76

4-Amino-2,6-dimethylthieno[2,3-b]pyridine-3-carbonitrile

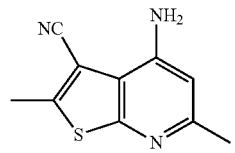

A mixture of 3-bromo-2,6-dimethylthieno[2,3-b]pyridin-4-amine (Description 8) (200 mg, 0.778 mmol), zinc cyanide (183 mg, 1.556 mmol) and tetrakis(triphenylphosphine)palladium(0) (90 mg, 0.078 mmol) in DMF (5 mL) was heated in a microwave at 140° C. for 1 h. Another batch of 3-bromo-2,6-dimethylthieno[2,3-b]pyridin-4-amine (200 mg, 0.778 mmol) was subjected to the same conditions. The mixtures were then combined and ethyl acetate (50 mL) added. The resulting mixture was washed with saturated $NaHCO_3$ (20 mL) followed by brine (20 mL×2) and the organic layer dried over $MgSO_4$, filtered and the solvent removed in vacuo. The residue was purified by normal phase chromatography, eluting with a gradient of 0-40% ethyl acetate in cyclohexane, to give the title compound (237.7 mg). LCMS (A) m/z: 204 [M+1]$^+$, Rt 0.61 min (acidic).

Description 77

3-{4-{[(3-Chlorophenyl)sulfonyl]amino}-6-methyl-3-[3-(methyloxy)phenyl]thieno[2,3-b]pyridin-2-yl}-2-propyn-1-yl methanesulfonate

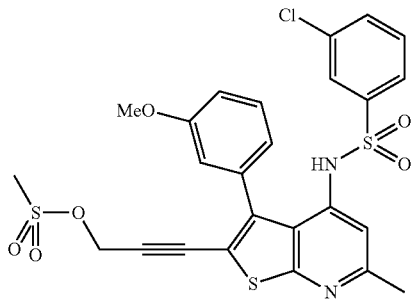 [SMILES: COc1cccc(-c2c(C#CCOS(C)(=O)=O)sc3nc(C)cc(NS(=O)(=O)c4cccc(Cl)c4)c23)c1]

Methane sulfonyl chloride (7.87 µl, 0.101 mmol) was added to a mixture of 3-chloro-N-{2-(3-hydroxy-1-propyn-1-yl)-6-methyl-3-[3-(methyloxy)phenyl]thieno[2,3-b]pyridin-4-yl}benzenesulfonamide (Example 85) (42 mg, 0.084 mmol) and Hunig's base (17.64 µl, 0.101 mmol) in THF (395 µl) and the mixture stirred at 0° C. The mixture was slowly allowed to warm to RT, with stirring, for 2 h. The mixture was then evaporated to dryness and the residue purified on silica, eluting with a gradient of 0-100% ethyl acetate in cyclohexane, to afford the title compound (14 mg). LCMS (A) m/z: 517 [M+1]+ (displacement of OSO₂Me by methanol), Rt 1.45 min (acidic).

Description 78

3-Bromo-5-(1-pyrrolidinyl)pyridine

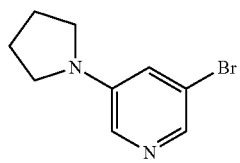

To a solution of 3,5-dibromopyridine (5.5 g, 23.22 mmol) in toluene (100 mL) was added BINAP (0.840 g, 1.350 mmol), Pd₂(dba)₃ (0.412 g, 0.45 mmol), sodium tert-butoxide (6.49 g, 67.5 mmol) and pyrrolidine (1.86 mL, 22.50 mmol). The reaction mixture was degassed (N₂, 10 min) and then heated at 100° C. for 2 h. The reaction mixture was cooled to RT and filtered through celite. The filtrate was evaporated and the residue purified by silica gel chromatography, eluting with a gradient of 0-30% ethyl acetate in cyclohexane, to afford the title compound (3.88 g). LCMS (A) m/z: 227/229 [M+1]+, Rt 0.87 min (acidic),

Description 79

3-(1-Pyrrolidinyl)-5-(4,4,5,5-tetramethyl-1,3,2-dioxaborolan-2-yl)pyridine

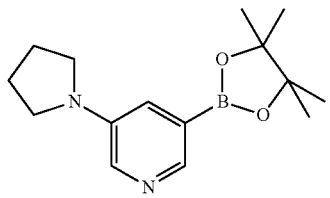 [SMILES: CC1(C)OB(c2cncc(N3CCCC3)c2)OC1(C)C]

A mixture of 3-bromo-5-(1-pyrrolidinyl)pyridine (Description 78) (3.88 g, 17.08 mmol), pinacol ester (4.34 g, 17.08 mmol), PdCl₂(dppf).DCM adduct (1.3 g, 1.592 mmol) and potassium acetate (5 g, 50.9 mmol) in DMF (50 mL) was degassed (N₂, 10 min) and then heated at 120° C. overnight. The mixture was concentrated, diluted with DCM (60 mL) and washed with water (20 mL×2). The organic layer was dried (phase separator) and concentrated, to afford the title compound (8.2 g, assume minimum purity 50%), which was used in the next step (Suzuki coupling) without further purification. LCMS (A) m/z: 193 [M+1]+, Rt 0.53 min (acidic) [corresponding to the boronic acid]. NMR (CDCl3, 400 MHz) shows methyl signals consistent with the presence of a pinacol moiety.

Description 80

4-(5-Bromo-3-pyridinyl)morpholine

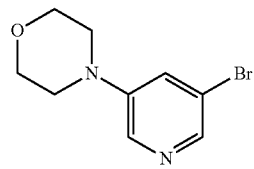 [SMILES: Brc1cncc(N2CCOCC2)c1]

A mixture of 3,5-dibromopyridine (2.121 g, 8.95 mmol), BINAP (0.279 g, 0.448 mmol), Pd₂(dba)₃ (0.137 g, 0.149 mmol) and sodium tert-butoxide (1.434 g, 14.92 mmol) in toluene (50 mL) was added morpholine (0.65 mL, 7.46 mmol). The mixture was then heated at 120° C. for ca. 5 h. After cooling to RT, the reaction mixture was filtered through celite and the filtrate was concentrated. The residue was purified by normal phase chromatography, eluting with a gradient of 0-50% ethyl acetate in DCM, to give the title compound (1.62 g). LCMS (A) m/z: 243/245 [M+1]+, Rt 0.83 min (acidic),

Description 81

4-[5-(4,4,5,5-Tetramethyl-1,3,2-dioxaborolan-2-yl)-3-pyridinyl]morpholine

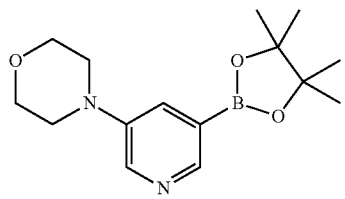 [SMILES: CC1(C)OB(c2cncc(N3CCOCC3)c2)OC1(C)C]

A mixture of 4-(5-bromo-3-pyridinyl)morpholine (Description 80) (360 mg, 1.481 mmol), bis(pinacolato)diboron (564 mg, 2.221 mmol), PdCl$_2$(dppf).DCM adduct (121 mg, 0.148 mmol) and potassium acetate (436 mg, 4.44 mmol) in 1,4-dioxane (6 mL) was heated at 100° C. for ca. 5 h. The mixture was concentrated and then diluted with DCM (50 mL) and washed with water (30 mL×3). The organic layer was dried and concentrated, to give what was thought to be the title compound (430 mg) which was used in the next step (Suzuki coupling) without further purification. LCMS (A) m/z: 209 [M+1]$^+$, Rt 0.42 min (acidic) [corresponding to the boronic acid].

Description 82

Ethyl 4-amino-2-({[(1,1-dimethylethyl)oxy]carbonyl}amino)-6-methyl-3-[3-(methyloxy)phenyl]thieno[2,3-b]pyridine-5-carboxylate

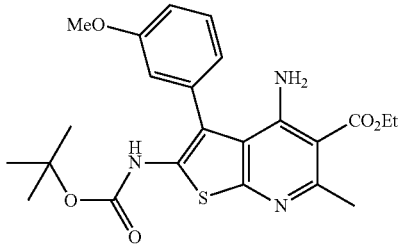 [SMILES: CCOC(=O)c1c(C)nc2sc(NC(=O)OC(C)(C)C)c(-c3cccc(OC)c3)c2c1N]

A mixture of ethyl 4-amino-2-bromo-6-methyl-3-[3-(methyloxy)phenyl]thieno[2,3-b]pyridine-5-carboxylate (Description 15) (1.52 g, 3.61 mmol), tert-butyl carbamate (0.845 g, 7.22 mmol), Pd$_2$(dba)$_3$ (0.066 g, 0.072 mmol), xantphos (0.084 g, 0.144 mmol) and Cs$_2$CO$_3$ (3.53 g, 10.82 mmol) in 1,4-dioxane (25 mL) was heated at 110° C. for ca. 6 h. After cooling to RT, the mixture was filtered through celite and the filtrate was concentrated. The residue was purified by chromatography, eluting with a gradient of 30-60% ethyl acetate in cyclohexane, to give the title compound (1.54 g). LCMS (A) m/z: 458 [M+1]$^+$, Rt 1.44 min (acidic).

Description 83

Ethyl 4-{[(3-chlorophenyl)sulfonyl]amino}-2-({[(1,1-dimethylethyl)oxy]carbonyl}amino)-6-methyl-3-[3-(methyloxy)phenyl]thieno[2,3-b]pyridine-5-carboxylate

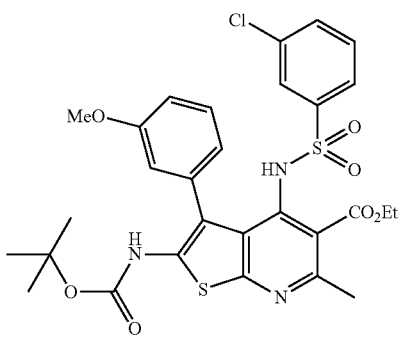 [SMILES: CCOC(=O)c1c(C)nc2sc(NC(=O)OC(C)(C)C)c(-c3cccc(OC)c3)c2c1NS(=O)(=O)c1cccc(Cl)c1]

To a stirred solution of ethyl 4-amino-2-({[(1,1-dimethylethyl)oxy]carbonyl}amino)-6-methyl-3-[3-(methyloxy)phenyl]thieno[2,3-b]pyridine-5-carboxylate (Description 82) (1.54 g, 3.37 mmol) in THF (30 mL) was added sodium tert-butoxide (1.294 g, 13.46 mmol) at RT and the mixture stirred for 15 min before 3-chlorobenzenesulfonyl chloride (0.948 mL, 6.73 mmol) was added. The resulting mixture was then stirred for ca. 3.5 h. Saturated NH$_4$Cl solution (50 mL) was then added to the mixture which was extracted with ethyl acetate (30 mL×3). The combined organics were washed with brine (30 mL), dried and concentrated. The residue was purified by normal phase chromatography, eluting with a gradient of 0-30% ethyl acetate in cyclohexane, to give the title compound (600 mg). LCMS (A) m/z: 632 [M+1]$^+$, Rt 1.74 min (acidic).

Description 84

2-Amino-4-{[(3-chlorophenyl)sulfonyl]amino}-6-methyl-3-[3-(methyloxy)phenyl]thieno[2,3-b]pyridine-5-carboxylic acid

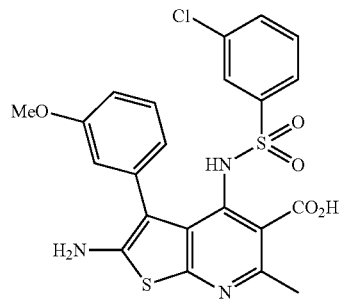 [SMILES: COc1cccc(-c2c(N)sc3nc(C)c(C(=O)O)c(NS(=O)(=O)c4cccc(Cl)c4)c23)c1]

A mixture of ethyl 4-{[(3-chlorophenyl)sulfonyl]amino}-2-({[(1,1-dimethylethyl)oxy]carbonyl}amino)-6-methyl-3-[3-(methyloxy)phenyl]thieno[2,3-b]pyridine-5-carboxylate (Description 83) (600 mg, 0.949 mmol) and aqueous NaOH (2M) (2.373 mL, 4.75 mmol) in DMSO (10 mL) was heated at 150° C. for 40 min. After cooling to RT, the mixture was diluted with water (20 mL) and acidified with formic acid to pH 6. The mixture was then extracted with ethyl acetate (30 mL×5) and the combined organics concentrated. The residue was passed through a phase separator (C18 cartridge) eluting with water (20 mL×3) and MeOH (20 mL×5) and the combined methanolic fractions concentrated and dried, to give the title compound (388 mg). LCMS (A) m/z: 504 [M+1]$^+$, Rt 1.17 min (acidic).

Description 85

N-{2-Amino-6-methyl-3-[3-(methyloxy)phenyl]thieno[2,3-b]pyridin-4-yl}-3-chlorobenzenesulfonamide

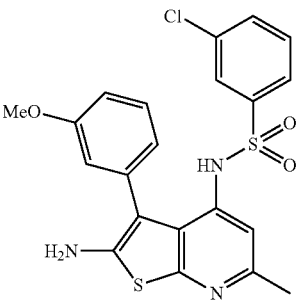

A mixture of 2-amino-4-{[(3-chlorophenyl)sulfonyl]amino}-6-methyl-3-[3-(methyloxy)phenyl]thieno[2,3-b]pyridine-5-carboxylic acid (Description 84) (388 mg, 0.770 mmol), copper (245 mg, 3.85 mmol) and quinoline (3 mL, 25.3 mmol) was heated at 200° C. for ca. 1 h. After cooling to RT, the mixture was purified by normal phase chromatography, eluting with a gradient of 50-70% ethyl acetate in cyclohexane followed by 10% MeOH in DCM, to give the title compound (127 mg). LCMS (A) m/z: 460 [M+1]$^+$, Rt 1.10 min (acidic).

Example 1

3-Chloro-N-{2,6-dimethyl-3-[3-(methyloxy)phenyl]thieno[2,3-b]pyridin-4-yl}-benzenesulfonamide

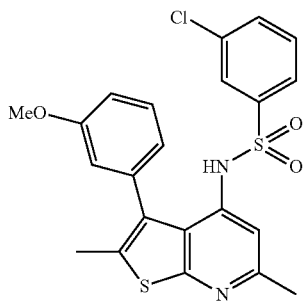

To a stirred solution of 2,6-dimethyl-3-[3-(methyloxy)phenyl]thieno[2,3-b]pyridin-4-amine (Description 4) (100 mg, 0.352 mmol) in THF (2 mL), cooled in an ice bath, was added LiHMDS (1M solution in THF) (0.774 mL, 0.774 mmol). The reaction mixture was stirred at RT for 1 h before the addition of 3-chlorobenzenesulfonyl chloride (0.124 mL, 0.879 mmol). The reaction mixture was then stirred at RT for a further 12 h. The reaction mixture was then diluted with water (15 mL) and the aqueous layer extracted with DCM (3×30 mL). The combined organic extracts were dried over a phase separating column and concentrated. Purification by chromatography on silica gel, eluting with a gradient of 0-20% ethyl acetate in cyclohexane, afforded a solid which was dissolved in the minimum amount of DCM. Upon addition of diethyl ether, a solid precipitated out which was collected by filtration, washed with diethyl ether and dried, to afford the title compound (89 mg). LCMS (A) m/z: 459 [M+1]$^+$, Rt 1.03 min (basic).

Example 2

N-{2,6-Dimethyl-3-[3-(methyloxy)phenyl]thieno[2,3-b]pyridin-4-yl}benzenesulfonamide

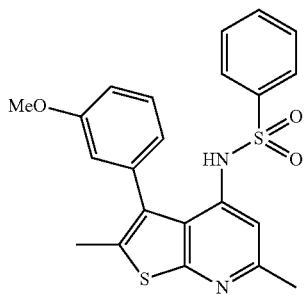 [SMILES: COc1cccc(-c2c(C)sc3nc(C)cc(NS(=O)(=O)c4ccccc4)c23)c1]

To a stirred solution of 2,6-dimethyl-3-[3-(methyloxy)phenyl]thieno[2,3-b]pyridin-4-amine (100 mg, 0.352 mmol) (Description 4) in THF (2 mL), cooled in an ice bath, was added LiHMDS (1M solution in THF) (0.774 mL, 0.774 mmol). The reaction mixture was stirred at RT for 45 min before the addition of benzenesulfonyl chloride (0.155 g, 0.879 mmol). The reaction mixture was then stirred at RT for a further 12 h. The reaction mixture was then diluted with water (15 mL) and the aqueous layer extracted with DCM (3×30 mL) and the combined organic extracts dried over a phase separating column and concentrated. MeOH (ca. 0.5 mL) was added to the residue which resulted in the precipitation of a solid. The solid was filtered, washed with MeOH (2 mL) and dried, to afford the title compound (88 mg). LCMS (A) m/z: 425 [M+1]$^+$, Rt 1.40 min (basic).

Example 3

3,4-Dichloro-N-{2,6-dimethyl-3-[3-(methyloxy)phenyl]thieno[2,3-b]pyridin-4-yl}-benzenesulfonamide

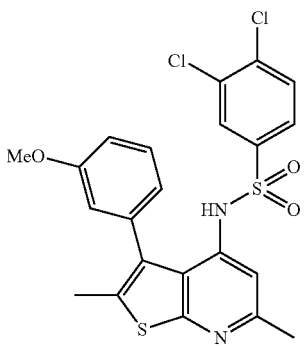 [SMILES: COc1cccc(-c2c(C)sc3nc(C)cc(NS(=O)(=O)c4ccc(Cl)c(Cl)c4)c23)c1]

Following the general method outlined in Example 2, starting from 3,4-dichlorobenzenesulfonyl chloride (0.216 g, 0.879 mmol), the title compound (79 mg) was isolated. LCMS (A) m/z: 493 [M+1]$^+$, Rt 1.09 min (basic).

Example 4

4-(1,1-Dimethylethyl)-N-{2,6-dimethyl-3-[3-(methyloxy)phenyl]thieno[2,3-b]pyridin-4-yl}benzenesulfonamide

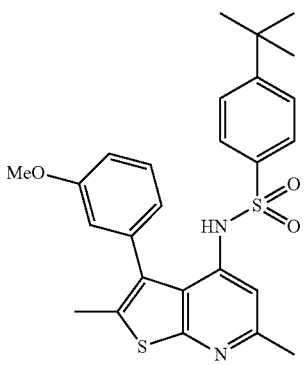 [SMILES: COc1cccc(-c2c(C)sc3nc(C)cc(NS(=O)(=O)c4ccc(C(C)(C)C)cc4)c23)c1]

Following the general method outlined in Example 2, starting from 4-tert-butylbenzenesulfonyl chloride, (0.205 g, 0.879 mmol), the title compound (67 mg) was isolated. LCMS (A) m/z: 481 [M+1]$^+$, Rt 1.47 min (basic).

Example 5

4-Bromo-N-{2,6-dimethyl-3-[3-(methyloxy)phenyl]thieno[2,3-b]pyridin-4-yl}-3-(trifluoromethyl)benzenesulfonamide

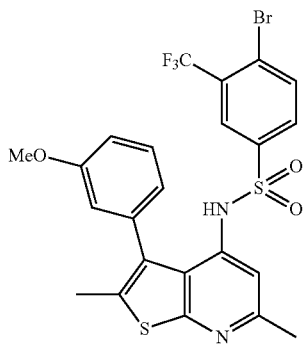 [SMILES: COc1cccc(-c2c(C)sc3nc(C)cc(NS(=O)(=O)c4ccc(Br)c(C(F)(F)F)c4)c23)c1]

Following the general method outlined in Example 2, starting from 4-bromo-3-(trifluoromethyl)benzenesulfonyl chloride (0.284 g, 0.879 mmol), the title compound (19 mg) was isolated. LCMS (A) m/z: 571/573 [M+1]+, Rt 1.10 min (basic).

Example 6

3,5-Dichloro-N-{2,6-dimethyl-3-[3-(methyloxy)phenyl]thieno[2,3-b]pyridin-4-yl}-benzenesulfonamide

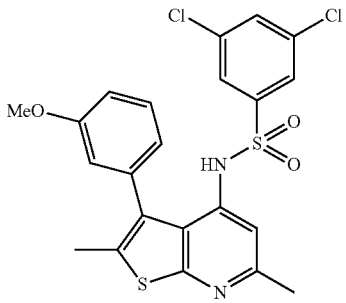 [SMILES: COc1cccc(-c2c(C)sc3nc(C)cc(NS(=O)(=O)c4cc(Cl)cc(Cl)c4)c23)c1]

Following the general method outlined in Example 2, starting from 3,5-dichlorobenzenesulfonyl chloride (0.216 g, 0.879 mmol), the title compound (73 mg) was isolated. LCMS (A) m/z: 493 [M+1]+, Rt 1.08 min (basic).

Example 7

N-{2,6-Dimethyl-3-[3-(methyloxy)phenyl]thieno[2,3-b]pyridin-4-yl}-3-nitrobenzenesulfonamide

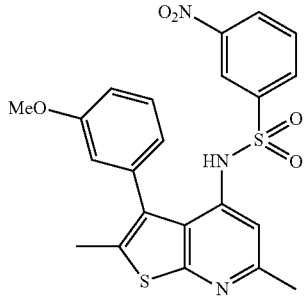 [SMILES: COc1cccc(-c2c(C)sc3nc(C)cc(NS(=O)(=O)c4cccc([N+](=O)[O-])c4)c23)c1]

Following the general method outlined in Example 2, starting from 3-nitrobenzenesulfonyl chloride (0.195 g, 0.879 mmol), the title compound (83 mg) was isolated. LCMS (A) m/z: 470 [M+1]+, Rt 0.95 min (basic).

Example 8

N-{2,6-Dimethyl-3-[3-(methyloxy)phenyl]thieno[2,3-b]pyridin-4-yl}-cyclohexanesulfonamide

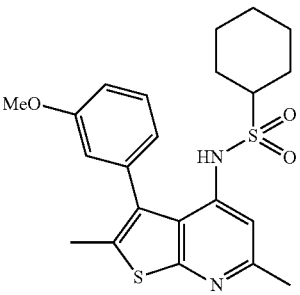 [SMILES: COc1cccc(-c2c(C)sc3nc(C)cc(NS(=O)(=O)C4CCCCC4)c23)c1]

To a stirred solution of 2,6-dimethyl-3-[3-(methyloxy)phenyl]thieno[2,3-b]pyridin-4-amine (100 mg, 0.352 mmol) (Description 4) in THF (2 mL), cooled in an ice bath, was added LiHMDS (1M solution in THF) (0.774 mL, 0.774 mmol). The reaction mixture was stirred at RT for 45 min before the addition of cyclohexanesulfonyl chloride (0.161 g, 0.879 mmol). The reaction mixture was then stirred at RT for a further 12 h. The reaction mixture was then re-cooled in an ice bath before the addition of LiHMDS (1M solution in THF) (0.352 mL, 0.352 mmol). The reaction mixture was then stirred at RT for 45 min before the addition of cyclohexanesulfonyl chloride (0.064 g, 0.352 mmol). The reaction mixture was then stirred at RT for a further 12 h. The reaction mixture was then diluted with water (15 mL) and the aqueous layer extracted with DCM (3×30 mL) and the combined organic extracts dried over a phase separating column and concentrated. The residue was then purified by MDAP (basic conditions), to afford the title compound (22 mg). LCMS (A) m/z: 431 [M+1]+, Rt 1.16 min (basic).

Example 9

N-{2,6-Dimethyl-3-[3-(methyloxy)phenyl]thieno[2,3-b]pyridin-4-yl}-1-butanesulfonamide

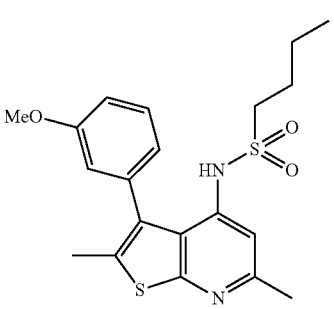 [SMILES: CCCCS(=O)(=O)Nc1cc(C)nc2sc(C)c(-c3cccc(OC)c3)c12]

Following the general method outlined in Example 8, starting from 1-butanesulfonyl chloride (0.193 g, 1.231 mmol), the title compound (15 mg) was isolated. LCMS (A) m/z: 405 [M+1]+, Rt 1.03 min (basic).

Example 10

Phenylmethyl 4-chloro-4-[({2,6-dimethyl-3-[3-(methyloxy)phenyl]thieno[2,3-b]pyridin-4-yl}amino)sulfonyl]-1-piperidinecarboxylate

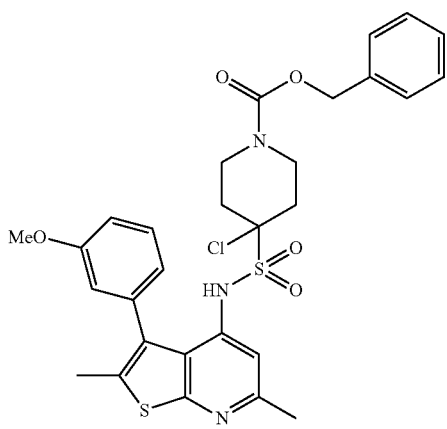 [SMILES: COc1cccc(-c2c(C)sc3nc(C)cc(NS(=O)(=O)C4(Cl)CCN(C(=O)OCc5ccccc5)CC4)c23)c1]

To a stirred solution of 2,6-dimethyl-3-[3-(methyloxy)phenyl]thieno[2,3-b]pyridin-4-amine (Description 4) (300 mg, 1.055 mmol) in THF (6 mL), cooled in an ice bath, was added LiHMDS (1.0M solution in THF) (5.27 mL, 5.27 mmol). The solution was stirred for 45 min, still in the ice bath, before the addition of phenylmethyl 4-(chlorosulfonyl)-1-piperidinecarboxylate (595 mg, 1.872 mmol). The reaction mixture was then stirred at RT for 16 h. The reaction mixture was then diluted with water (20 mL) and the aqueous layer extracted with DCM (3×30 mL). The combined organic extract was dried over a phase separating column and concentrated. Purification by chromatography on silica gel, eluting with a gradient of 0-20% ethyl acetate in cyclohexane, afforded the title compound (108 mg). LCMS (A) m/z: 600 [M+1]$^+$, Rt 1.01 min (basic).

Example 11

N-{2,6-Dimethyl-3-[3-(methyloxy)phenyl]thieno[2,3-b]pyridin-4-yl}-3-(methyloxy)benzenesulfonamide

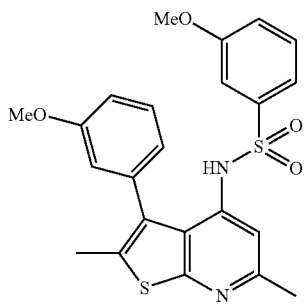 [SMILES: COc1cccc(-c2c(C)sc3nc(C)cc(NS(=O)(=O)c4cccc(OC)c4)c23)c1]

To a stirred solution of 2,6-dimethyl-3-[3-(methyloxy)phenyl]thieno[2,3-b]pyridin-4-amine (Description 4) (120 mg, 0.422 mmol) in THF (2 mL), cooled in an ice bath, was added LiHMDS (1M solution in THF) (0.928 mL, 0.928 mmol). The reaction mixture was stirred at RT for 45 min before the addition of 3-(methyloxy)benzenesulfonyl chloride (218 mg, 1.055 mmol) and the reaction mixture was then stirred at RT for a further 12 h. The reaction mixture was then diluted with water (15 mL) and the aqueous layer extracted with DCM (3×30 mL) and the combined organic extracts dried over a phase separating column and concentrated. Purification by chromatography on silica gel, eluting with a gradient of 0-20% ethyl acetate in cyclohexane, afforded a solid which was dissolved in the minimum amount of DCM. Upon addition of diethyl ether, a solid precipitated out which was collected by filtration, washed with diethyl ether and dried, to afford the title compound (134 mg). LCMS (A) m/z: 455 [M+1]$^+$, Rt 1.12 min (basic).

Example 12

N-{2,6-Dimethyl-3-[3-(methyloxy)phenyl]thieno[2,3-b]pyridin-4-yl}-4-(methyloxy)benzenesulfonamide

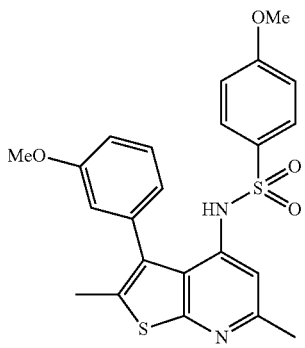 [SMILES: COc1ccc(S(=O)(=O)Nc2cc(C)nc3sc(C)c(-c4cccc(OC)c4)c23)cc1]

Following the general method outlined in Example 11, starting from 4-(methyloxy)benzenesulfonyl chloride (218 mg, 1.055 mmol), the title compound (50 mg) was isolated. LCMS (A) m/z: 455 [M+1]$^+$, Rt 1.21 min (basic).

Example 13

4-Chloro-N-{2,6-dimethyl-3-[3-(methyloxy)phenyl]thieno[2,3-b]pyridin-4-yl}

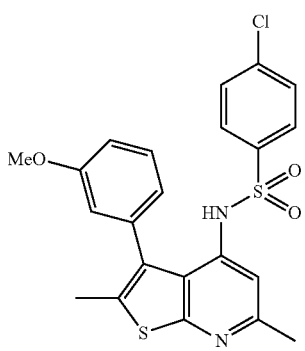 [SMILES: COc1cccc(-c2c(C)sc3nc(C)cc(NS(=O)(=O)c4ccc(Cl)cc4)c23)c1]

Following the general method outlined in Example 11, starting from 4-chlorobenzenesulfonyl chloride (223 mg, 1.055 mmol), the title compound (53 mg) was isolated. LCMS (A) m/z: 459 [M+1]⁺, Rt 1.09 min (basic).

Example 14

N-{2,6-Dimethyl-3-[3-(methyloxy)phenyl]thieno[2,3-b]pyridin-4-yl}-4-methylbenzenesulfonamide

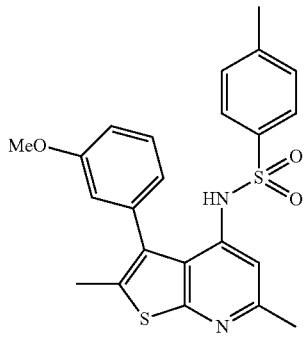 [SMILES: COc1cccc(-c2c(C)sc3nc(C)cc(NS(=O)(=O)c4ccc(C)cc4)c23)c1]

Following the general method outlined in Example 11, starting from 4-methylbenzenesulfonyl chloride (201 mg, 1.055 mmol), the title compound (38 mg) was isolated. LCMS (A) m/z: 439 [M+1]⁺, Rt 1.24 min (basic).

Example 15

3-Chloro-N-(2,6-dimethyl-3-phenylthieno[2,3-b]pyridin-4-yl)benzenesulfonamide

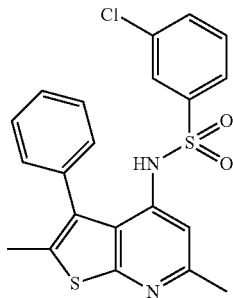 [SMILES: Cc1cc(NS(=O)(=O)c2cccc(Cl)c2)c2c(-c3ccccc3)c(C)sc2n1]

Under nitrogen, N-(3-bromo-2,6-dimethylthieno[2,3-b]pyridin-4-yl)-3-chlorobenzenesulfonamide (90 mg, 0.208 mmol) (Example 61) was dissolved in 1,4-dioxane (3 mL). Phenylboronic acid (38.1 mg, 0.313 mmol), PdCl₂(dppf).DCM (17.02 mg, 0.021 mmol) and Cs₂CO₃ (204 mg, 0.625 mmol) were added and the mixture heated in a microwave at 120° C. for 30 min. Toluene (3 mL) was added and the mixture heated in a microwave as follows: 130° C. for 30 min, 150° C. for 30 min (×2) and finally 180° C. for 15 min (×2). Water (10 mL) was then added and the mixture extracted with ethyl acetate (3×10 mL). The organic layer was dried over MgSO₄, filtered and the solvent removed in vacuo. Purification by chromatography on silica gel, eluting with a gradient of 0-30% ethyl acetate in cyclohexane was followed by further purification by MDAP (basic conditions), to afford the title compound (14.4 mg). LCMS (A) m/z: 429 [M+1]⁺, Rt 1.10 min (basic), Rt 1.47 min (acidic).

Example 16

3-Chloro-N-{3-[3-(dimethylamino)phenyl]-2,6-dimethylthieno[2,3-b]pyridin-4-yl}-benzenesulfonamide

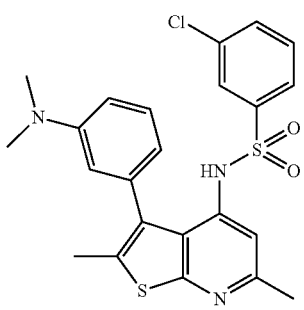 [SMILES: Cc1cc(NS(=O)(=O)c2cccc(Cl)c2)c2c(-c3cccc(N(C)C)c3)c(C)sc2n1]

Under nitrogen, N-(3-bromo-2,6-dimethylthieno[2,3-b]pyridin-4-yl)-3-chlorobenzenesulfonamide (100 mg, 0.232 mmol) (Example 61) was dissolved in toluene (2 mL) and [3-(dimethylamino)phenyl]boronic acid (57.3 mg, 0.347 mmol), PdCl₂(dppf).DCM (18.91 mg, 0.023 mmol) and Cs₂CO₃ (226 mg, 0.695 mmol) were added and the mixture heated in a microwave at 150° C. for 30 min. Water (10 mL) was then added and the mixture extracted with ethyl acetate (3×10 mL). The organic layer was dried over MgSO₄, filtered and the solvent removed in vacuo. Purification by chromatography on silica gel, eluting with a gradient of 0-30% ethyl acetate in cyclohexane, was followed by trituration with MeOH, to afford the title compound (39.5 mg). LCMS (A) m/z: 472 [M+1]⁺, Rt 0.97 min (basic), Rt 1.51 min (acidic).

Example 17

3-Chloro-N-[3-(4-chlorophenyl)-2,6-dimethylthieno[2,3-b]pyridin-4-yl]benzenesulfonamide

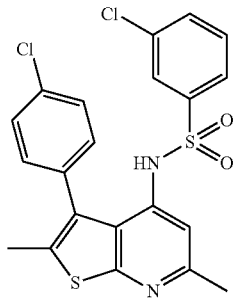 [SMILES: Cc1cc(NS(=O)(=O)c2cccc(Cl)c2)c2c(-c3ccc(Cl)cc3)c(C)sc2n1]

Following the general method as outlined in Example 16, starting from (4-chlorophenyl)boronic acid (54.3 mg, 0.347 mmol), the title compound (40 mg) was isolated. LCMS (A) m/z: 463 [M+1]⁺, Rt 1.10 min (basic), Rt 1.44 min (acidic).

Example 18

3-Chloro-N-{2,6-dimethyl-3-[4-(methyloxy)phenyl]thieno[2,3-b]pyridin-4-yl}-benzenesulfonamide

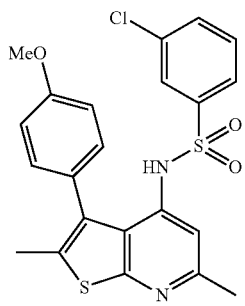 [SMILES: COc1ccc(-c2c(C)sc3nc(C)cc(NS(=O)(=O)c4cccc(Cl)c4)c23)cc1]

Following the general method as outlined in Example 16, starting from [4-(methyloxy)phenyl]boronic acid (52.8 mg, 0.347 mmol), the title compound (34.4 mg) was isolated. LCMS (A) m/z: 459 [M+1]$^+$, Rt 1.15 min (basic), Rt 1.46 min (acidic).

Example 19

3-Chloro-N-[2,6-dimethyl-3-(4-methylphenyl)thieno[2,3-b]pyridin-4-yl]benzenesulfonamide

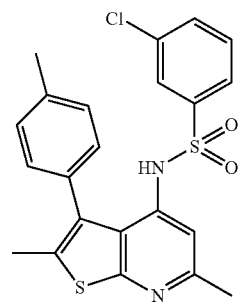 [SMILES: Cc1ccc(-c2c(C)sc3nc(C)cc(NS(=O)(=O)c4cccc(Cl)c4)c23)cc1]

Following the general method as outlined in Example 16, starting from (4-methylphenyl)boronic acid (47.2 mg, 0.347 mmol), the title compound (14.9 mg) was isolated. LCMS (A) m/z: 443 [M+1]$^+$, Rt 1.22 min (basic), Rt 1.53 min (acidic).

Example 20

3-Chloro-N-[3-(3,4-dichlorophenyl)-2,6-dimethylthieno[2,3-b]pyridin-4-yl]benzenesulfonamide

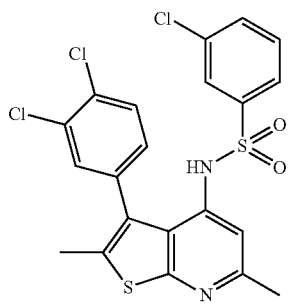 [SMILES: Cc1cc(NS(=O)(=O)c2cccc(Cl)c2)c2c(-c3ccc(Cl)c(Cl)c3)c(C)sc2n1]

Following the general method as outlined in Example 16, starting from (3,4-dichlorophenyl)boronic acid (66.3 mg, 0.347 mmol), the title compound (34.9 mg) was isolated. LCMS (A) m/z: 497/499 [M+1]$^+$, Rt 1.14 min (basic), Rt 1.45 min (acidic).

Example 21

3-Chloro-N-{2,6-dimethyl-3-[4-(trifluoromethyl)phenyl]thieno[2,3-b]pyridin-4-yl}-benzenesulfonamide

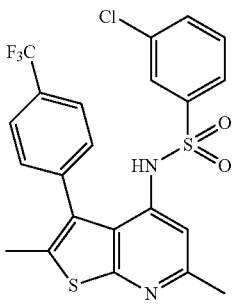 [SMILES: Cc1cc(NS(=O)(=O)c2cccc(Cl)c2)c2c(-c3ccc(C(F)(F)F)cc3)c(C)sc2n1]

Following the general method as outlined in Example 16, starting from [4-(trifluoromethyl)phenyl]boronic acid (66.0 mg, 0.347 mmol), the title compound (30.7 mg) was isolated. LCMS (A) m/z: 497 [M+1]$^+$, Rt 1.12 min (basic), Rt 1.42 min (acidic).

Example 22

3-Chloro-N-{3-[4-chloro-3-(trifluoromethyl)phenyl]-2,6-dimethylthieno[2,3-b]pyridin-4-yl}-benzenesulfonamide

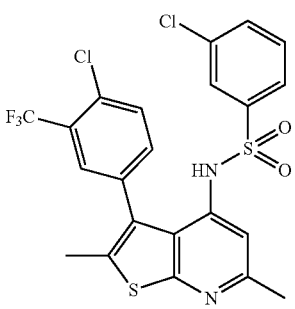 [SMILES: Cc1cc(NS(=O)(=O)c2cccc(Cl)c2)c2c(-c3ccc(Cl)c(C(F)(F)F)c3)c(C)sc2n1]

Following the general method as outlined in Example 16, starting from [4-chloro-3-(trifluoromethyl)phenyl]boronic acid (78 mg, 0.347 mmol), the title compound (33.4 mg) was isolated. LCMS (A) m/z: 531 [M+1]$^+$, Rt 1.02 min (basic), Rt 1.43 min (acidic).

Example 23

3-Chloro-N-{3-[4-(dimethylamino)phenyl]-2,6-dimethylthieno[2,3-b]pyridin-4-yl}-benzenesulfonamide

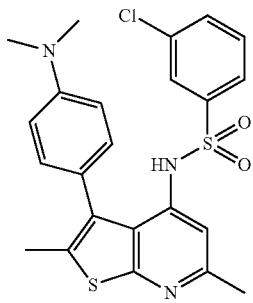 [SMILES: Cc1cc(NS(=O)(=O)c2cccc(Cl)c2)c2c(-c3ccc(N(C)C)cc3)c(C)sc2n1]

Following the general method as outlined in Example 16, starting from [4-(dimethylamino)phenyl]boronic acid (57.3 mg, 0.347 mmol), the title compound (52.6 mg) was isolated. LCMS (A) m/z: 472 [M+1]$^+$, Rt 1.00 min (basic).

Example 24

3-Chloro-N-{2,6-dimethyl-3-[3-methyl-4-(methyloxy)phenyl]thieno[2,3-b]pyridin-4-yl}-benzenesulfonamide

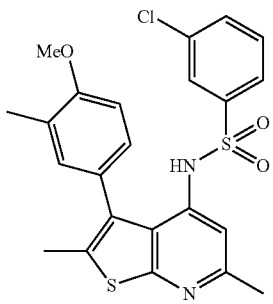 [SMILES: COc1ccc(-c2c(C)sc3nc(C)cc(NS(=O)(=O)c4cccc(Cl)c4)c23)cc1C]

Following the general method as outlined in Example 16, starting from [3-methyl-4-(methyloxy)phenyl]boronic acid (57.7 mg, 0.347 mmol), the title compound (26 mg) was isolated. LCMS (A) m/z: 473 [M+1]$^+$, Rt 1.00 min (basic), Rt 1.55 min (acidic).

Example 25

3-Chloro-N-[2,6-dimethyl-3-(3-pyridinyl)thieno[2,3-b]pyridin-4-yl]benzenesulfonamide

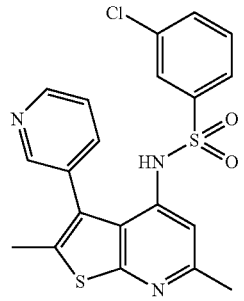 [SMILES: Cc1cc(NS(=O)(=O)c2cccc(Cl)c2)c2c(-c3cccnc3)c(C)sc2n1]

Under nitrogen, N-(3-bromo-2,6-dimethylthieno[2,3-b]pyridin-4-yl)-3-chlorobenzenesulfonamide (100 mg, 0.232 mmol) (Example 61) was dissolved in 1,4-dioxane (1.5 mL) and water (0.7 mL). 3-Pyridinylboronic acid (42.7 mg, 0.347 mmol), tetrakis(triphenylphosphine)palladium(0) (26.8 mg, 0.023 mmol) and potassium carbonate (96 mg, 0.695 mmol) were added and the mixture heated in a microwave at 120° C. for 15 min. Ethyl acetate (10 mL) was added and the mixture washed with water (2×5 mL). The organic layer was then dried over MgSO$_4$, filtered and the solvent removed in vacuo. Purification by chromatography on silica gel, eluting with a gradient of 5% MeOH in DCM, was followed by further purification by MDAP (basic conditions), to afford the title compound (32.7 mg). LCMS (A) m/z: 430 [M+1]$^+$, Rt 0.83 min (basic), Rt 0.85 min (acidic).

Example 26

3-Chloro-N-[2,6-dimethyl-3-(5-pyrimidinyl)thieno[2,3-b]pyridin-4-yl]benzenesulfonamide

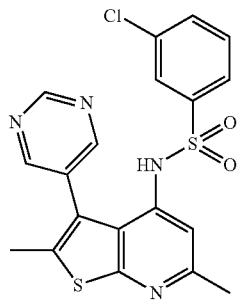 [SMILES: Cc1cc(NS(=O)(=O)c2cccc(Cl)c2)c2c(-c3cncnc3)c(C)sc2n1]

Following the general method as outlined in Example 25, starting from 5-pyrimidinylboronic acid (43.0 mg, 0.347 mmol), the title compound (29.6 mg) was isolated. LCMS (A) m/z: 431 [M+1]$^+$, Rt 0.78 min (basic), Rt 0.97 min (acidic).

Example 27

3-Chloro-N-[2,6-dimethyl-3-(1-methyl-1H-pyrazol-4-yl)thieno[2,3-b]pyridin-4-yl]-benzenesulfonamide

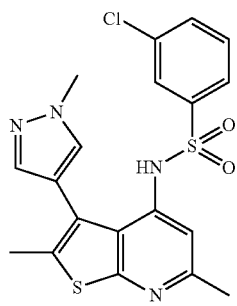 [SMILES: Cc1cc(NS(=O)(=O)c2cccc(Cl)c2)c2c(-c3cnn(C)c3)c(C)sc2n1]

Following the general method as outlined in Example 25, starting from (1-methyl-1H-pyrazol-4-yl)boronic acid (43.7 mg, 0.347 mmol), the title compound (52.5 mg) was isolated. LCMS (A) m/z: 433 [M+1]$^+$, Rt 0.81 min (basic), Rt 1.19 min (acidic).

Example 28

3-Chloro-N-[3-(3-chlorophenyl)-2,6-dimethylthieno[2,3-b]pyridin-4-yl]benzenesulfonamide

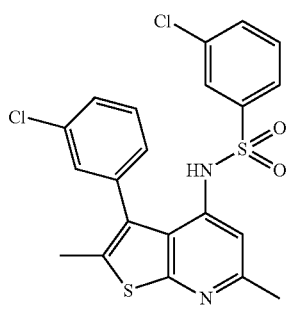 [SMILES: Cc1cc(NS(=O)(=O)c2cccc(Cl)c2)c2c(-c3cccc(Cl)c3)c(C)sc2n1]

To a solution of 3-(3-chlorophenyl)-2,6-dimethylthieno[2,3-b]pyridin-4-amine (100 mg, 0.346 mmol) (Description 9) in THF (3 mL) was added potassium tert-butoxide (155 mg, 1.385 mmol) and the mixture stirred for 5 min before the addition of 3-chlorobenzenesulfonyl chloride (0.049 mL, 0.346 mmol). The mixture was then stirred for 1 h and the solvent then removed in vacuo. Ethyl acetate (10 mL) was then added and the mixture washed with water (3×10 mL). The organic layer was dried over MgSO$_4$, filtered and the solvent removed in vacuo. Purification by chromatography on silica gel, eluting with a gradient of 0-30% ethyl acetate in cyclohexane, was followed by trituration with MeOH, to afford the title compound (67.8 mg). LCMS (A) m/z: 463 [M+1]$^+$, Rt 1.09 min (basic), Rt 1.44 min (acidic).

Example 29

N-[3-(3-Chlorophenyl)-2,6-dimethylthieno[2,3-b]pyridin-4-yl]-3-(methyloxy)benzenesulfonamide

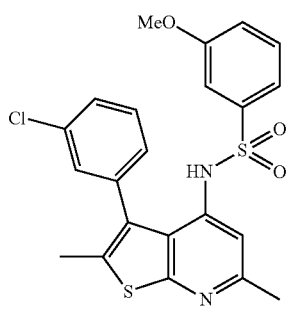 [SMILES: COc1cccc(S(=O)(=O)Nc2cc(C)nc3sc(C)c(-c4cccc(Cl)c4)c23)c1]

Following the general method as outlined in Example 28, starting from 3-(methyloxy)benzenesulfonyl chloride (179 mg, 0.866 mmol), the title compound (62.4 mg) was isolated. LCMS (A) m/z: 459 [M+1]$^+$, Rt 1.11 min (basic), Rt 1.43 min (acidic).

Example 30

N-(2,6-Dimethyl-3-phenylthieno[2,3-b]pyridin-4-yl)benzenesulfonamide

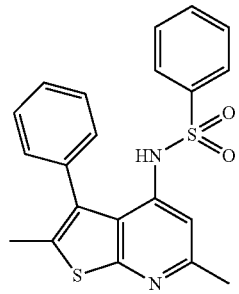 [SMILES: Cc1cc(NS(=O)(=O)c2ccccc2)c2c(-c3ccccc3)c(C)sc2n1]

Following the general method as outlined in Example 28, starting from 2,6-dimethyl-3-phenylthieno[2,3-b]pyridin-4-amine (97 mg, 0.381 mmol) (Description 10) and benzenesulfonyl chloride (135 mg, 0.763 mmol), the title compound (28.7 mg) was isolated. LCMS (A) m/z: 395 [M+1]$^+$, Rt 0.96 min (basic), Rt 1.39 min (acidic).

Example 31

1,1-Dimethylethyl 4-[3-(4-{[(3-chlorophenyl)sulfonyl]amino}-2,6-dimethylthieno[2,3-b]pyridin-3-yl)phenyl]-1-piperazinecarboxylate

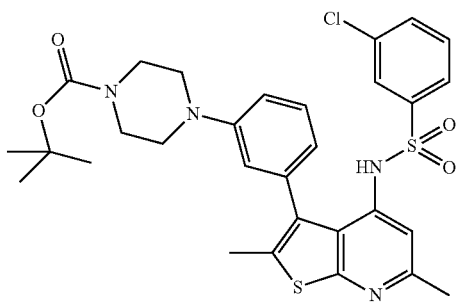 [SMILES: Cc1cc(NS(=O)(=O)c2cccc(Cl)c2)c2c(-c3cccc(N4CCN(C(=O)OC(C)(C)C)CC4)c3)c(C)sc2n1]

Following the general method as outlined in Example 28, starting from 1,1-dimethylethyl 4-[3-(4-amino-2,6-dimethylthieno[2,3-b]pyridin-3-yl)phenyl]-1-piperazinecarboxylate (195 mg, 0.445 mmol) (Description 11), the title compound (76 mg) was isolated. LCMS (A) m/z: 613 [M+1]$^+$, Rt 1.18 min (basic), Rt 1.62 min (acidic).

Example 32

3-Chloro-N-{2,6-dimethyl-3-[3-(1-piperazinyl)phenyl]thieno[2,3-b]pyridin-4-yl}-benzenesulfonamide

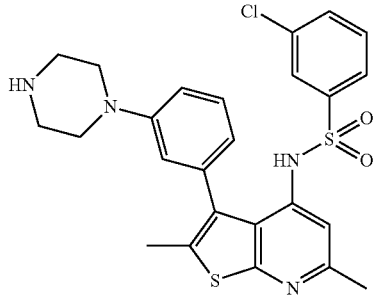 [SMILES: Cc1cc(NS(=O)(=O)c2cccc(Cl)c2)c2c(-c3cccc(N4CCNCC4)c3)c(C)sc2n1]

83

To a solution of 1,1-dimethylethyl 4-[3-(4-{[(3-chlorophenyl)sulfonyl]amino}-2,6-dimethylthieno[2,3-b]pyridin-3-yl)phenyl]-1-piperazinecarboxylate (60 mg, 0.098 mmol) (Example 31) in DCM (2 mL) was added 4M HCl in dioxane (0.122 mL, 0.489 mmol) and the mixture stirred for 3 h. Additional 4M HCl in dioxane (2.446 mL, 9.78 mmol) was then added and the mixture stirred overnight. Aqueous NaOH (5M) was then added to the solution dropwise until it was basic. Ethyl acetate (10 mL) was added and the mixture washed with water (2×5 mL). The organic layer was dried over MgSO₄, filtered and the solvent removed in vacuo. The residue was purified by MDAP (acidic conditions) and further purification using HPLC (CHIRALPAK AD (250×20 mm-10 micron); isohexane/ethanol gradient, 18 mL/min) afforded the title compound (12.7 mg). LCMS (A) m/z: 513 [M+1]⁺, Rt 0.93 min (basic), Rt 1.01 min (acidic).

Example 33

N-{2-Bromo-6-methyl-3-[3-(methyloxy)phenyl]thieno[2,3-b]pyridin-4-yl}-3-chlorobenzenesulfonamide

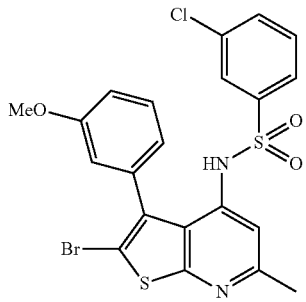 [SMILES: COc1cccc(-c2c(Br)sc3nc(C)cc(NS(=O)(=O)c4cccc(Cl)c4)c23)c1]

To a stirred solution of 2-bromo-6-methyl-3-[3-(methyloxy)phenyl]thieno[2,3-b]pyridin-4-amine (213 mg, 0.610 mmol) (Description 17) in THF (5 mL) was added sodium tert-butoxide (234 mg, 2.440 mmol) at RT and the mixture stirred for 15 min before the addition of 3-chlorobenzenesulfonyl chloride (0.172 mL, 1.220 mmol). The mixture was then stirred for 3.5 h. Saturated ammonium chloride solution (20 mL) was added to the mixture which was then extracted with ethyl acetate (2×15 mL). The combined organics were washed with brine (20 mL), dried and concentrated. Purification by chromatography on silica gel, eluting with a gradient of 0-30% ethyl acetate in cyclohexane, afforded the title compound (157 mg). LCMS (A) m/z: 523/525 [M+1]⁺, Rt 1.54 min (acidic), Rt 1.83 min (basic).

Alternatively, to a stirred solution of 2-bromo-6-methyl-3-[3-(methyloxy)phenyl]thieno-[2,3-b]pyridin-4-amine (460 mg, 1.317 mmol) (Description 17) in DMF (10 mL) was added sodium tert-butoxide (316 mg, 3.29 mmol) and 3-chlorobenzenesulfonyl chloride (0.371 mL, 2.63 mmol). The reaction mixture was stirred at RT under nitrogen for 1 h. The reaction mixture was then diluted with ethyl acetate (25 mL) and NaHCO₃ (50 mL). The organic layer was then separated and the aqueous layer re-extracted with ethyl acetate (2×20 mL). The combined organic layer was dried over Na₂SO₄ and the solvent concentrated in vacuo. Purification by chromatography on silica gel, eluting with a gradient of 0-50% ethyl acetate in cyclohexane, afforded the title compound (447 mg).

84

Example 34

3-Chloro-N-{2-cyano-6-methyl-3-[3-(methyloxy)phenyl]thieno[2,3-b]pyridin-4-yl}-benzenesulfonamide

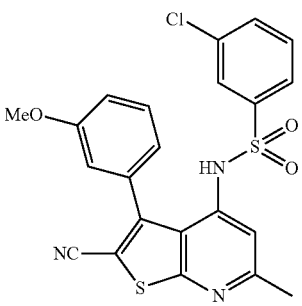 [SMILES: COc1cccc(-c2c(C#N)sc3nc(C)cc(NS(=O)(=O)c4cccc(Cl)c4)c23)c1]

A mixture of N-{2-bromo-6-methyl-3-[3-(methyloxy)phenyl]thieno[2,3-b]pyridin-4-yl}-3-chlorobenzenesulfonamide (85 mg, 0.162 mmol) (Example 33), potassium ferrocyanide (13.71 mg, 0.032 mmol), copper(I) iodide (3.09 mg, 0.016 mmol) in 1-methylimidazole (1 mL, 12.55 mmol) was subjected to microwave reaction at 160° C. for 1 h. Purification by chromatography on silica gel, eluting with a gradient of 40-60% ethyl acetate in cyclohexane, afforded the title compound (24 mg). LCMS (A) m/z: 470 [M+1]⁺, Rt 1.58 min (acidic), Rt 1.09 min (basic).

Alternatively, a mixture of N-{2-bromo-6-methyl-3-[3-(methyloxy)phenyl]thieno[2,3-b]pyridin-4-yl}-3-chlorobenzenesulfonamide (310 mg, 0.592 mmol) (Example 33), potassium ferrocyanide (50.0 mg, 0.118 mmol), copper(I) iodide (11.27 mg, 0.059 mmol) in 1-methylimidazole (3 mL, 37.6 mmol) was heated at 160° C. for 2 h. Extra potassium ferrocyanide (100 mg, 0.118 mmol) was added and heating continued at 160° C. for 21 h. The mixture was then cooled to RT. Purification by chromatography on silica gel, eluting with a gradient of 0-60% ethyl acetate in cyclohexane, afforded the title compound (208 mg).

Example 35

4-{[(3-Chlorophenyl)sulfonyl]amino}-6-methyl-3-[3-(methyloxy)phenyl]thieno[2,3-b]pyridine-2-carboxylic acid

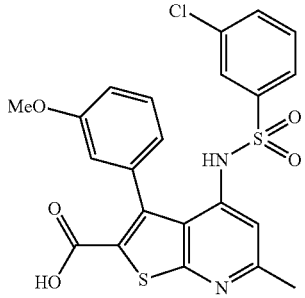 [SMILES: COc1cccc(-c2c(C(=O)O)sc3nc(C)cc(NS(=O)(=O)c4cccc(Cl)c4)c23)c1]

A suspension of 3-chloro-N-{2-cyano-6-methyl-3-[3-(methyloxy)phenyl]thieno[2,3-b]pyridin-4-yl}benzenesulfonamide (100 mg, 0.213 mmol) (Example 34) in HCl (37% weight) (3.0 mL, 36.5 mmol) was stirred at RT for 18 h. 4M HCl in 1,4-dioxane (3 mL) was added and the mixture heated at 60° C. for 5 h followed by 120° C. for 1.5 h. After cooling to RT, the mixture was concentrated and purified by chromatography on silica gel, eluting with a gradient of 10-20% MeOH in DCM, to give the title compound (53 mg). LCMS (A) m/z: 489 [M+1]⁺, Rt 1.24 min (acidic), Rt 0.67 min (basic).

Example 36

Methyl 4-{[(3-chlorophenyl)sulfonyl]amino}-6-methyl-3-[3-(methyloxy)phenyl]thieno[2,3-b]pyridine-2-carboxylate

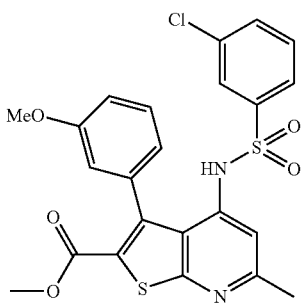 [SMILES: COC(=O)c1sc2nc(C)cc(NS(=O)(=O)c3cccc(Cl)c3)c2c1-c1cccc(OC)c1]

A mixture of 4-{[(3-chlorophenyl)sulfonyl]amino}-6-methyl-3-[3-(methyloxy)phenyl]-thieno[2,3-b]pyridine-2-carboxylic acid (90 mg, 0.184 mmol) (Example 35) and concentrated sulfuric acid (0.069 mL, 1.288 mmol) in MeOH (5 mL) was heated at 70° C. under nitrogen for 20 h and then left stand at RT for 2 days. The reaction mixture was then concentrated and purified by chromatography on silica gel, eluting with a gradient of 30-50% ethyl acetate in cyclohexane, to give the title compound (46 mg). LCMS (A) m/z: 503 [M+1]⁺, Rt 1.41 min (acidic), Rt 0.96 min (basic).

Example 37

3-Chloro-N-[6-methyl-3-[3-(methyloxy)phenyl]-2-(1-pyrrolidinyl)thieno[2,3-b]pyridin-4-yl]-benzenesulfonamide

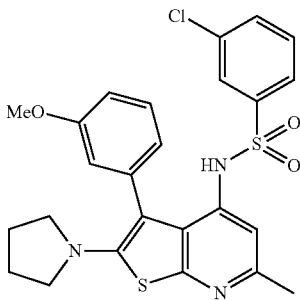 [SMILES: COc1cccc(-c2c(N3CCCC3)sc3nc(C)cc(NS(=O)(=O)c4cccc(Cl)c4)c23)c1]

A mixture of N-{2-bromo-6-methyl-3-[3-(methyloxy)phenyl]thieno[2,3-b]pyridin-4-yl}-3-chlorobenzenesulfonamide (50 mg, 0.095 mmol) (Example 33), pyrrolidine (0.039 mL, 0.477 mmol), Pd₂(dba)₃ (8.74 mg, 9.54 μmol), 2-di-tert-butylphosphino-2',4',6'-triisopropylbiphenyl (8.11 mg, 0.019 mmol) and Cs₂CO₃ (93 mg, 0.286 mmol) in THF (1 mL) was heated at 70° C. for 19 h. The mixture was then filtered through celite and the filtrate concentrated. Purification by chromatography on silica gel, eluting with a gradient of 20-50% ethyl acetate in DCM was followed by further purification by MDAP (acidic conditions), to give the title compound (3.9 mg). LCMS (A) m/z: 514 [M+1]⁺, Rt 1.56 min (acidic), Rt 1.09 min (basic).

Example 38

4-{[(3-Chlorophenyl)sulfonyl]amino}-N,6-dimethyl-3-[3-(methyloxy)phenyl]thieno[2,3-b]-pyridine-2-carboxamide

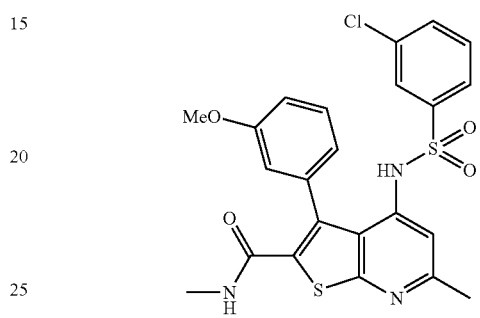

In an dried round bottom flask was added 4-{[(3-chlorophenyl)sulfonyl]amino}-6-methyl-3-[3-(methyloxy)phenyl]thieno[2,3-b]pyridine-2-carboxylic acid (50 mg, 0.102 mmol) (Example 35), DCM (1 mL), oxalyl chloride (0.013 mL, 0.153 mmol) and DMF (10 μL). The resulting mixture was stirred at RT for 10 min. Methylamine (2M in THF) (0.256 mL, 0.511 mmol) was then added dropwise and the mixture stirred at RT for 30 min. Aqueous NaHCO₃ solution (25 mL) and DCM (25 mL) were then added and the organic layer separated. The aqueous was re-extracted with DCM (2×20 mL) and the combined organics washed with brine (30 mL), dried and concentrated. Purification by chromatography on silica gel, eluting with a gradient of 0-10% MeOH in DCM was followed by further purification by chromatography on silica gel, eluting with a gradient of 20-50% ethyl acetate in DCM, to give the title compound (28 mg). LCMS (A) m/z: 502 [M+1]⁺, Rt 1.21 min (acidic), Rt 0.91 min (basic).

Example 39

4-{[(3-Chlorophenyl)sulfonyl]amino}-N,N,6-trimethyl-3-[3-(methyloxy)phenyl]thieno[2,3-b]-pyridine-2-carboxamide

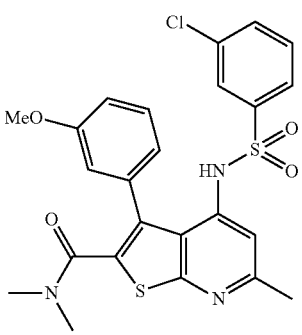 [SMILES: COc1cccc(-c2c(C(=O)N(C)C)sc3nc(C)cc(NS(=O)(=O)c4cccc(Cl)c4)c23)c1]

Following general method outlined in Example 38, starting from dimethylamine (2M in THF) (0.256 mL, 0.511 mmol), the title compound (27 mg) was isolated. LCMS (A) m/z: 516 [M+1]$^+$, Rt 0.83 min (basic).

Example 40

3-Chloro-N-{6-methyl-3-[3-(methyloxy)phenyl]-2-phenylthieno[2,3-b]pyridin-4-yl}-benzenesulfonamide

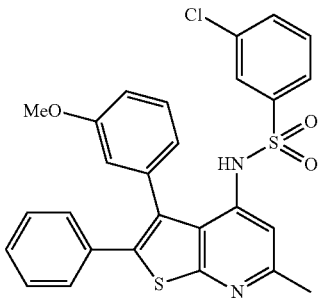 [SMILES: COc1cccc(-c2c(-c3ccccc3)sc3nc(C)cc(NS(=O)(=O)c4cccc(Cl)c4)c23)c1]

A mixture of N-{2-bromo-6-methyl-3-[3-(methyloxy)phenyl]thieno[2,3-b]pyridin-4-yl}-3-chlorobenzenesulfonamide (50 mg, 0.095 mmol) (Example 33), phenylboronic acid (13.97 mg, 0.115 mmol), sodium carbonate (20.23 mg, 0.191 mmol) and PdCl$_2$(dppf).DCM (3.90 mg, 4.77 µmol) in DMF (1 mL) and water (250 µl) was heated at 90° C. under nitrogen, for 3.5 h. The reaction mixture was then cooled to RT and concentrated. Purification by chromatography on silica gel, eluting with a gradient of 0-20% ethyl acetate in DCM, afforded the title compound (28 mg). LCMS (A) m/z: 521 [M+1]$^+$, Rt 1.57 min (acidic), Rt 0.98 min (basic).

Example 41

3-Chloro-N-[6-methyl-3-[3-(methyloxy)phenyl]-2-(3-pyridinyl)thieno[2,3-b]pyridin-4-yl]-benzenesulfonamide

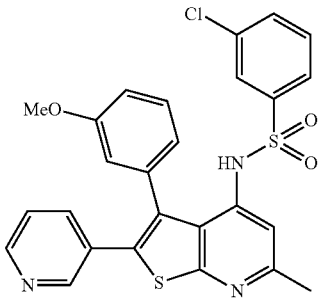 [SMILES: COc1cccc(-c2c(-c3cccnc3)sc3nc(C)cc(NS(=O)(=O)c4cccc(Cl)c4)c23)c1]

A mixture of N-{2-bromo-6-methyl-3-[3-(methyloxy)phenyl]thieno[2,3-b]pyridin-4-yl}-3-chlorobenzenesulfonamide (50 mg, 0.095 mmol) (Example 33), tetrakis(triphenylphosphine)palladium(0) (5.51 mg, 4.77 µmol), sodium carbonate (20.23 mg, 0.191 mmol) and 3-pyridineboronic acid (14.08 mg, 0.115 mmol) in acetonitrile (1 mL) and water (250 µl) was heated at 80° C. under nitrogen for 17 h. The reaction mixture was then cooled to RT and concentrated. Purification by chromatography on silica gel, eluting with a gradient of 0-50% ethyl acetate in DCM, afforded the title compound (20.5 mg). LCMS (A) m/z: 522 [M+1]$^+$, Rt 1.33 min (acidic), Rt 0.89 min (basic).

Example 42

3-Chloro-N-{2-(2-furanyl)-6-methyl-3-[3-(methyloxy)phenyl]thieno[2,3-b]pyridin-4-yl}-benzenesulfonamide

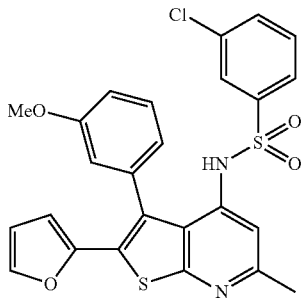 [SMILES: COc1cccc(-c2c(-c3ccco3)sc3nc(C)cc(NS(=O)(=O)c4cccc(Cl)c4)c23)c1]

Following general method outlined in Example 41, starting from furan-2-boronic acid (16.02 mg, 0.143 mmol), the title compound (37.9 mg) was isolated. LCMS (A) m/z: 511 [M+1]$^+$, Rt 1.53 min (acidic), Rt 0.98 min (basic).

Example 43

3-Chloro-N-{2-(3,5-dimethyl-4-isoxazolyl)-6-methyl-3-[3-(methyloxy)phenyl]thieno[2,3-b]pyridin-4-yl}benzenesulfonamide

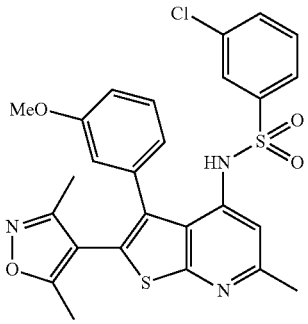 [SMILES: COc1cccc(-c2c(-c3c(C)noc3C)sc3nc(C)cc(NS(=O)(=O)c4cccc(Cl)c4)c23)c1]

N-{2-Bromo-6-methyl-3-[3-(methyloxy)phenyl]thieno[2,3-b]pyridin-4-yl}-3-chlorobenzenesulfonamide (100 mg, 0.191 mmol) (Example 33), (3,5-dimethyl-4-isoxazolyl)boronic acid (40.4 mg, 0.286 mmol), palladium(II) acetate (4.29 mg, 0.019 mmol), xantphos (22.09 mg, 0.038 mmol) and Cs$_2$CO$_3$ (187 mg, 0.573 mmol) were weighed into a round bottom flask. Degassed toluene (2 mL) was added to the mixture which was then heated at 110° C. for 19 h. After cooling to RT, the mixture was filtered through celite and rinsed with ethyl acetate (30 mL) and the combined filtrate concentrated. Purification by chromatography on silica gel, eluting with a gradient of 0-50% ethyl acetate in isohexane, afforded the title compound (19 mg). LCMS (A) m/z: 540 [M+1]$^+$, Rt 1.40 min (acidic), Rt 0.94 min (basic).

Example 44

3-Chloro-N-[6-methyl-3-[3-(methyloxy)phenyl]-2-(2-thienyl)thieno[2,3-b]pyridin-4-yl]-benzenesulfonamide

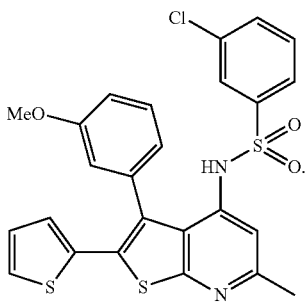 [SMILES: COc1cccc(-c2c(-c3cccs3)sc3nc(C)cc(NS(=O)(=O)c4cccc(Cl)c4)c23)c1]

Following general method outlined in Example 41, starting from thiophene-2-boronic acid (18.32 mg, 0.143 mmol), the title compound (18 mg) was isolated. LCMS (A) m/z: 527 [M+1]$^+$, Rt 1.56 min (acidic), Rt 1.03 min (basic).

Example 45

3-Chloro-N-{6-methyl-2-(1-methylethyl)-3-[3-(methyloxy)phenyl]thieno[2,3-b]pyridin-4-yl}-benzenesulfonamide trifluoroacetate

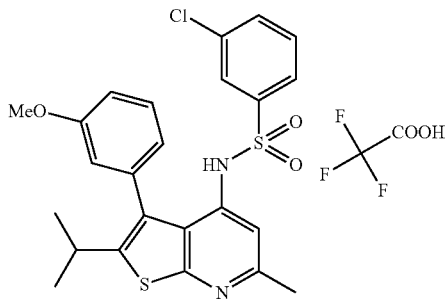

Following general method outlined in Example 1, starting from 6-methyl-2-(1-methylethyl)-3-[3-(methyloxy)phenyl]thieno[2,3-b]pyridin-4-amine (60 mg, 0.192 mmol) (Description 21), the title compound (37 mg) was isolated as a TFA salt. LCMS (B) m/z: 487 [M+1]$^+$, Rt 3.51 min.

Example 46

1-Methyl-N-{6-methyl-2-(1-methylethyl)-3-[3-(methyloxy)phenyl]thieno[2,3-b]pyridin-4-yl}-1H-imidazole-4-sulfonamide trifluoroacetate

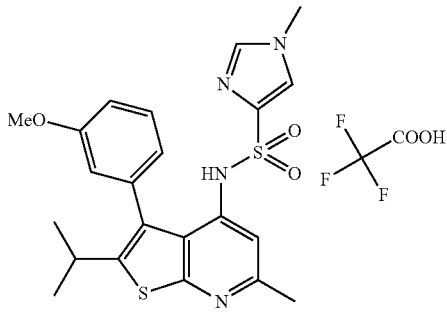

Following general method outlined in Example 1, starting from 6-methyl-2-(1-methylethyl)-3-[3-(methyloxy)phenyl]thieno[2,3-b]pyridin-4-amine (60 mg, 0.192 mmol) (Description 21) and 1-methyl-1H-imidazole-4-sulfonyl chloride (69.4 mg, 0.384 mmol), the title compound (37 mg) was isolated as a TFA salt. LCMS (B) m/z: 457 [M+1]$^+$, Rt 2.85 min.

Example 47

N-{3-[3,4-Bis(methyloxy)phenyl]-6-methylthieno[2,3-b]pyridin-4-yl}-3-chlorobenzenesulfonamide trifluoroacetate

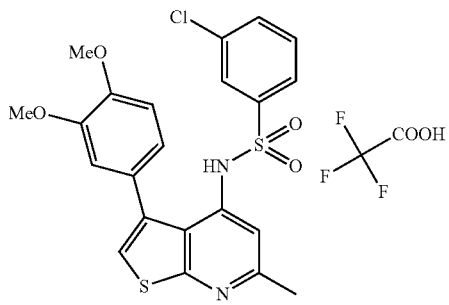

Following general method outlined in Example 1, starting from 3-[3,4-bis(methyloxy)phenyl]-6-methylthieno[2,3-b]pyridin-4-amine (40 mg, 0.097 mmol) (Description 24), the title compound (12 mg) was isolated as a TFA salt. LCMS (B) m/z: 475 [M+1]$^+$, Rt 2.99 min.

Example 48

3-Chloro-N-{3-[3-(dimethylamino)phenyl]-2-ethyl-6-methylthieno[2,3-b]pyridin-4-yl}benzenesulfonamide trifluoroacetate

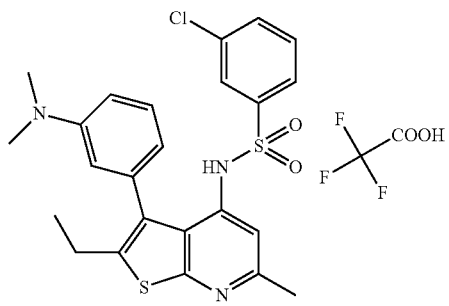

Following general method outlined in Example 1, starting from 3-[3-(dimethylamino)phenyl]-2-ethyl-6-methylthieno[2,3-b]pyridin-4-amine (60 mg, 0.192 mmol) (Description 29), the title compound (4 mg) was isolated as a TFA salt. LCMS (B) m/z: 486 [M+1]$^+$, Rt 2.94 min.

Example 49

N-{2,6-Dimethyl-3-[3-(methyloxy)phenyl]thieno[2,3-b]pyridin-4-yl}-1-methyl-1H-imidazole-4-sulfonamide

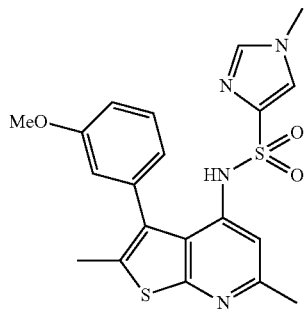 [SMILES: COc1cccc(-c2c(C)sc3nc(C)cc(NS(=O)(=O)c4cn(C)cn4)c23)c1]

Following general method outlined in Example 1, starting from 1-methyl-1H-imidazole-4-sulfonyl chloride (84 mg, 0.464 mmol), the title compound (34 mg) was isolated. LCMS (B) m/z: 429 [M+1]$^+$, Rt 2.62 min.

Example 50

4-Chloro-N-{3-[3-(dimethylamino)phenyl]-2-ethyl-6-methylthieno[2,3-b]pyridin-4-yl}benzenesulfonamide trifluoroacetate

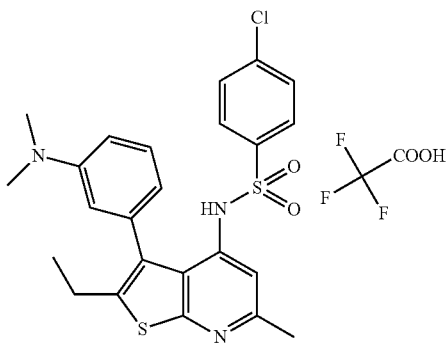

Following general method outlined in Example 1, starting from 3-[3-(dimethylamino)phenyl]-2-ethyl-6-methylthieno[2,3-b]pyridin-4-amine (60 mg, 0.193 mmol) (Description 29) and 4-chlorobenzenesulfonyl chloride (81 mg, 0.385 mmol), the title compound (7.1 mg) was isolated as a TFA salt. LCMS (B) m/z: 486 [M+1]$^+$, Rt 3.03 min.

Example 51

N-{3-[3,4-Bis(methyloxy)phenyl]-6-methylthieno[2,3-b]pyridin-4-yl}-1-methyl-1H-imidazole-4-sulfonamide trifluoroacetate

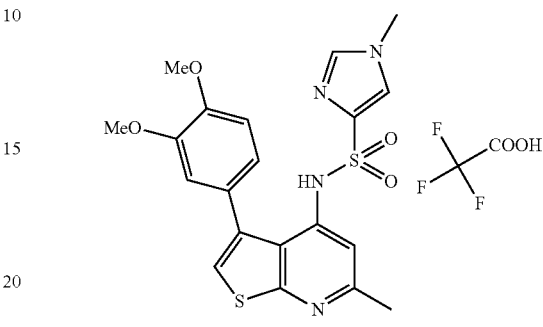

Following general method outlined in Example 1, starting from 3-[3,4-bis(methyloxy)phenyl]-6-methylthieno[2,3-b]pyridin-4-amine (62 mg, 0.150 mmol) (Description 24) and 1-methyl-1H-imidazole-4-sulfonyl chloride (54.0 mg, 0.299 mmol), the title compound (26 mg) was isolated as a TFA salt. LCMS (B) m/z: 445 [M+1]$^+$, Rt 2.41 min.

Example 52

5-Bromo-N-{2,6-dimethyl-3-[3-(methyloxy)phenyl]thieno[2,3-b]pyridin-4-yl}-3-pyridinesulfonamide trifluoroacetate

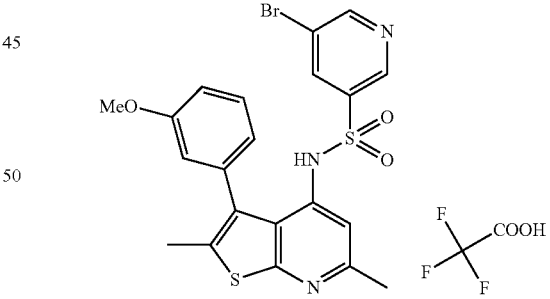

To a suspension of 2,6-dimethyl-3-[3-(methyloxy)phenyl]thieno[2,3-b]pyridin-4-amine (50 mg, 0.176 mmol) (Description 4) and potassium tert-butoxide in DMF (2 mL) was added 5-bromopyridine-3-sulfonyl chloride (54.1 mg, 0.211 mmol). The resulting mixture was stirred at RT for 3 h, then quenched by aqueous HCl (2M), diluted with water and extracted with ethyl acetate. The combined organic layers were concentrated and residue purified with reverse phase preparative HPLC (B), to afford the title compound (3 mg) as a TFA salt. LCMS (B) m/z: 504/506 [M+1]$^+$, Rt 2.53 min.

Example 53

N-{2,6-Dimethyl-3-[3-(methyloxy)phenyl]thieno[2,3-b]pyridin-4-yl}-6-phenyl-3-pyridinesulfonamide trifluoroacetate

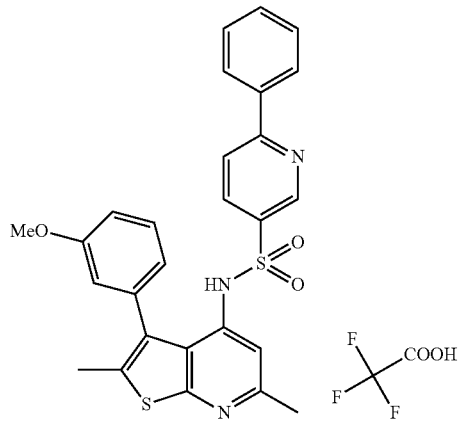

Following general method outlined in Example 52, starting from 6-phenyl-3-pyridinesulfonyl chloride (35.7 mg, 0.141 mmol), the title compound (16.7 mg) was isolated as a TFA salt. LCMS (B) m/z: 502 [M+1]$^+$, Rt 2.80 min.

Example 54

1,2-Dimethyl-N-{6-methyl-2-(1-methylethyl)-3-[3-(methyloxy)phenyl]thieno[2,3-b]pyridin-4-yl}-1H-imidazole-4-sulfonamide trifluoroacetate

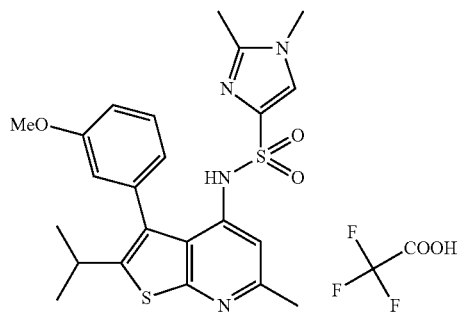

Following general method outlined in Example 52, starting from 6-methyl-2-(1-methylethyl)-3-[3-(methyloxy)phenyl]thieno[2,3-b]pyridin-4-amine (35 mg, 0.112 mmol) (Description 21) and 1,2-dimethylimidazole-4-sulfonyl chloride (21.8 mg, 0.112 mmol), the title compound (9.0 mg) was isolated as a TFA salt. LCMS (B) m/z: 471 [M+1]$^+$, Rt 2.14 min.

Example 55

N-{6-Methyl-2-(1-methylethyl)-3-[3-(methyloxy)phenyl]thieno[2,3-b]pyridin-4-yl}-6-phenyl-3-pyridinesulfonamide trifluoroacetate

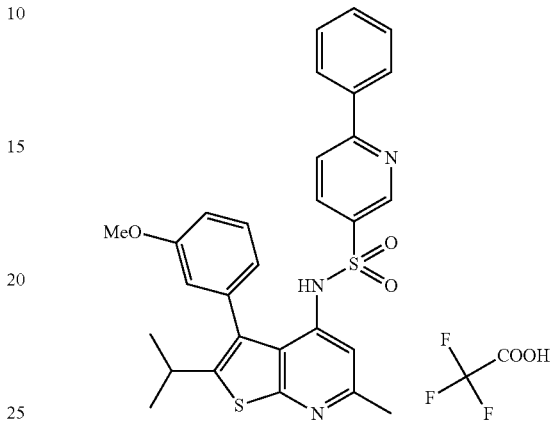

Following general method outlined in Example 52, starting from 6-methyl-2-(1-methylethyl)-3-[3-(methyloxy)phenyl]thieno[2,3-b]pyridin-4-amine (40 mg, 0.128 mmol) (Description 21) and 6-phenyl-3-pyridinesulfonyl chloride (39 mg, 0.154 mmol), the title compound (12.2 mg) was isolated as a TFA salt. LCMS (B) m/z: 530 [M+1]$^+$, Rt 3.02 min.

Example 56

N-{2,6-Dimethyl-3-[3-(methyloxy)phenyl]thieno[2,3-b]pyridin-4-yl}-1,2-dimethyl-1H-imidazole-4-sulfonamide trifluoroacetate

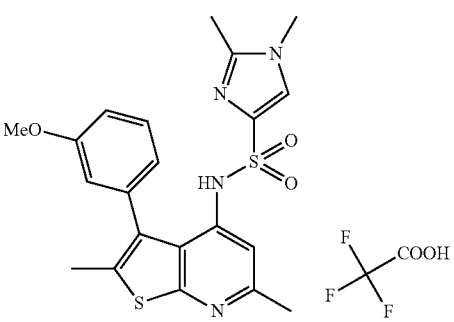

Following general method outlined in Example 52, starting from 1,2-dimethylimidazole-4-sulfonyl chloride (41.1 mg, 0.211 mmol), the title compound (2.8 mg) was isolated as a TFA salt. LCMS (B) m/z: 443 [M+1]$^+$, Rt 1.93 min.

Example 57

3-Chloro-N-{2-(3-furanyl)-6-methyl-3-[3-(methyloxy)phenyl]thieno[2,3-b]pyridin-4-yl}-benzenesulfonamide

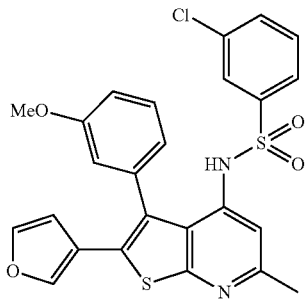 [SMILES: COc1cccc(-c2c(-c3ccoc3)sc3nc(C)cc(NS(=O)(=O)c4cccc(Cl)c4)c23)c1]

A mixture of N-{2-bromo-6-methyl-3-[3-(methyloxy)phenyl]thieno[2,3-b]pyridin-4-yl}-3-chlorobenzenesulfonamide (70 mg, 0.134 mmol) (Example 33), 3-furanylboronic acid (22.43 mg, 0.20 mmol), sodium carbonate (28.3 mg, 0.267 mmol) and tetrakis(triphenylphosphine)palladium(0) (15.44 mg, 0.013 mmol) in acetonitrile (1 mL) and water (250 μl) was heated at 80° C. under nitrogen for 1.5 h. The reaction mixture was cooled to RT and concentrated. Purification by chromatography on silica gel, eluting with a gradient of 0-50% ethyl acetate in isohexane, afforded the title compound (55 mg). LCMS (A) m/z: 511 [M+1]$^+$, Rt 1.51 min (acidic), Rt 0.98 min (basic).

Example 58

3-Chloro-N-[6-methyl-3-[3-(methyloxy)phenyl]-2-(1H-pyrazol-4-yl)thieno[2,3-b]pyridin-4-yl]benzenesulfonamide

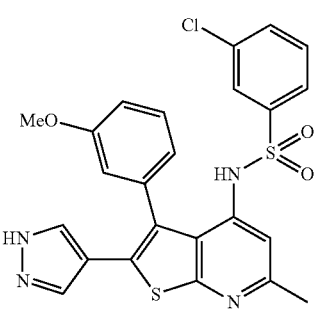 [SMILES: COc1cccc(-c2c(-c3cn[nH]c3)sc3nc(C)cc(NS(=O)(=O)c4cccc(Cl)c4)c23)c1]

Following the general method outlined in Example 57, starting from pyrazole-4-boronic acid (12.82 mg, 0.115 mmol), the title compound (17 mg) was isolated. LCMS (A) m/z: 511 [M+1]$^+$, Rt 1.27 min (acidic), Rt 0.84 min (basic).

Example 59

3-Chloro-N-[3,6-dimethyl-2-(3-pyridinyl)thieno[2,3-b]pyridin-4-yl]benzenesulfonamide

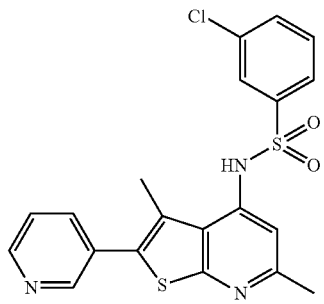 [SMILES: Cc1cc(NS(=O)(=O)c2cccc(Cl)c2)c2c(C)c(-c3cccnc3)sc2n1]

To a stirred solution of 3,6-dimethyl-2-(3-pyridinyl)thieno[2,3-b]pyridin-4-amine (45 mg, 0.176 mmol) (Description 34) in DMF (1.5 mL) was added sodium tert-butoxide (42.3 mg, 0.441 mmol) and 3-chlorobenzenesulfonyl chloride (0.050 mL, 0.352 mmol). The reaction mixture was stirred at RT under nitrogen for 3 h and then diluted with ethyl acetate (20 mL) and water (30 mL). The organic layer was separated and the aqueous layer re-extracted with ethyl acetate (2×15 mL). The combined organic layers were dried over Na$_2$SO$_4$ and concentrated. Purification by chromatography on silica gel, eluting with a gradient of 0-100% ethyl acetate in DCM was followed by further purification by MDAP (acidic conditions), to afford the title compound (17.8 mg). LCMS (A) m/z: 430 [M+1]$^+$, Rt 1.06 min (acidic), Rt 0.86 min (basic).

Example 60

3-Chloro-N-[2,6-dimethyl-3-(phenylmethyl)thieno[2,3-b]pyridin-4-yl]benzenesulfonamide

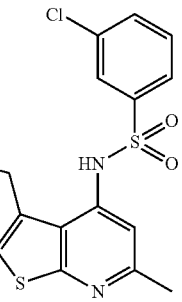

Under nitrogen, N-(3-bromo-2,6-dimethylthieno[2,3-b]pyridin-4-yl)-3-chlorobenzenesulfonamide (100 mg, 0.232 mmol) (Example 61) was dissolved in 1,4-dioxane (1.5 mL) and water (0.7 mL). 4,4,5,5-Tetramethyl-2-(phenylmethyl)-1,3,2-dioxaborolane (0.077 mL, 0.347 mmol), tetrakis(triphenylphosphine)palladium(0) (26.8 mg, 0.023 mmol) and potassium carbonate (96 mg, 0.695 mmol) were added and the mixture heated at 100° C. overnight. Ethyl acetate (10 mL) was added and the mixture washed with water (2×5 mL). The organic layer was dried over MgSO$_4$, filtered and the solvent removed in vacuo. Purification by chromatography on silica gel, eluting with a gradient of 70% ethyl acetate in cyclohexane, afforded the title compound (33.3 mg). LCMS (A) m/z: 443 [M+1]+, Rt 1.28 min (acidic), Rt 0.97 min (basic).

Example 61

N-(3-Bromo-2,6-dimethylthieno[2,3-b]pyridin-4-yl)-3-chlorobenzenesulfonamide

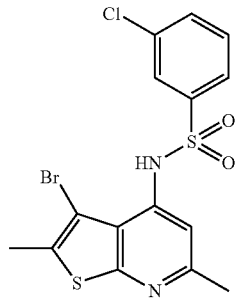

To a solution of 3-bromo-2,6-dimethylthieno[2,3-b]pyridin-4-amine (1.6 g, 6.22 mmol) (Description 8) in THF (30 mL) was added potassium tert-butoxide (2.79 g, 24.89 mmol) and the mixture stirred for 5 min before adding 3-chlorobenzenesulfonyl chloride (2.190 mL, 15.56 mmol). The mixture was stirred for 1 h and the solvent was then removed in vacuo. Ethyl acetate (50 mL) was added and the mixture washed with water (3×30 mL). The organic layer was dried over MgSO$_4$, filtered and the solvent removed in vacuo. Purification by chromatography on silica gel, eluting with a gradient of 0-30% ethyl acetate in cyclohexane, afforded the title compound (1.3 g). LCMS (A) m/z: 431/433 [M+1]+, Rt 1.38 min (acidic).

Example 62

3-Chloro-N-{3-[3-(methyloxy)phenyl]thieno[2,3-b]pyridin-4-yl}benzenesulfonamide

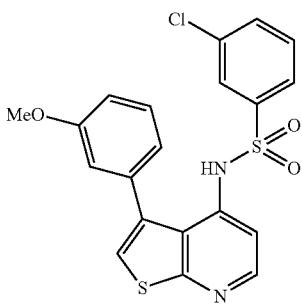

A mixture of 4-chloro-3-[3-(methyloxy)phenyl]thieno[2,3-b]pyridine (Description 43) (100 mg, 0.363 mmol), 3-chlorobenzensulfonamide (90 mg, 0.471 mmol), palladium(II) acetate (8.14 mg, 0.036 mmol), xantphos (42.0 mg, 0.073 mmol), and Cs$_2$CO$_3$ (236 mg, 0.725 mmol) in 1,4-dioxane (3.6 mL) was degassed with nitrogen for 5 min. The mixture was heated at 150° C. for 45 min in a microwave and then poured into water (50 mL) and extracted with DCM (30 mL×4). The organic layers were combined, washed with brine (50 mL), dried over MgSO$_4$, filtered and evaporated in vacuo. The residue was purified by chromatography on silica, eluting with a gradient of 0-10% ethanol in toluene, followed by further purification by MDAP (basic conditions), to give the title compound (72 mg). LCMS (A) m/z: 431 [M+1]+, Rt 1.34 min (acidic).

Example 63

3-Chloro-N-[2,6-dimethyl-3-(1H-pyrazol-4-yl)thieno[2,3-b]pyridin-4-yl]benzenesulfonamide

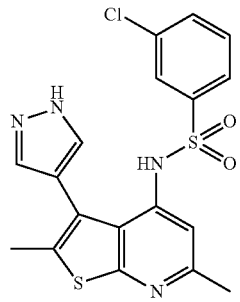

Under nitrogen, N-(3-bromo-2,6-dimethylthieno[2,3-b]pyridin-4-yl)-3-chlorobenzenesulfonamide (Example 61) (100 mg, 0.232 mmol) was dissolved in 1,4-dioxane (2.5 mL) and water (1 mL). 1,1-Dimethylethyl 4-(4,4,5,5-tetramethyl-1,3,2-dioxaborolan-2-yl)-1H-pyrazole-1-carboxylate (102 mg, 0.347 mmol), bis(triphenylphosphine)palladium(II) chloride (16.26 mg, 0.023 mmol) and potassium carbonate (96 mg, 0.695 mmol) were added and the mixture heated in a microwave at 100° C. for 15 min (×3). The solution was concentrated, ethyl acetate (10 mL) added and the mixture washed with water (2×5 mL). The organic layer was dried over MgSO$_4$, filtered and the solvent removed in vacuo. The residue was purified by normal phase chromatography, eluting with a gradient of 0-60% ethyl acetate in cyclohexane, to give the title compound (10.7 mg). LCMS (A) m/z: 419 [M+1]+, Rt 1.20 min (acidic).

Example 64

3-Chloro-N-[2,6-dimethyl-3-(5-methyl-2-furanyl)thieno[2,3-b]pyridin-4-yl]benzenesulfonamide

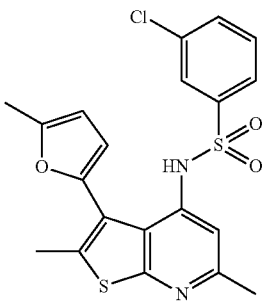

Under nitrogen, N-(3-bromo-2,6-dimethylthieno[2,3-b]pyridin-4-yl)-3-chlorobenzenesulfonamide (Example 61) (90 mg, 0.208 mmol) was dissolved in 1,4-dioxane (1.5 mL) and water (0.7 mL). 4,4,5,5-Tetramethyl-2-(5-methyl-2-furanyl)-1,3,2-dioxaborolane (0.064 mL, 0.313 mmol), tetrakis(triphenylphosphine)palladium(0) (24.09 mg, 0.021 mmol) and potassium carbonate (86 mg, 0.625 mmol) were added and the mixture heated in a microwave at 120° C. for 10 min. Ethyl acetate (10 mL) was then added and the mixture washed with water (2×5 mL). The organic layer was dried over MgSO₄, filtered and the solvent removed in vacuo. The residue was purified by normal phase chromatography, eluting with a gradient of 0-30% ethyl acetate in cyclohexane and further triturated with MeOH, to give the title compound (40.5 mg). LCMS (A) m/z: 433 [M+1]⁺, Rt 1.50 min (acidic).

Example 65

3-Chloro-N-[2,6-dimethyl-3-(5-methyl-2-thienyl)thieno[2,3-b]pyridin-4-yl]benzenesulfonamide

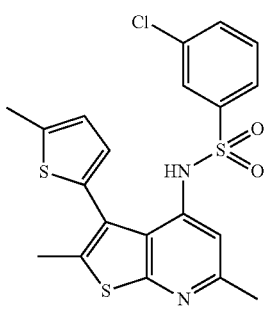

Under nitrogen, N-(3-bromo-2,6-dimethylthieno[2,3-b]pyridin-4-yl)-3-chlorobenzenesulfonamide (Example 61) (100 mg, 0.232 mmol) was dissolved in 1,4-dioxane (1.5 mL) and water (0.7 mL). (5-Methyl-2-thienyl)boronic acid (49.3 mg, 0.347 mmol), tetrakis(triphenylphosphine)palladium(0) (26.8 mg, 0.023 mmol) and potassium carbonate (96 mg, 0.695 mmol) were added and the mixture heated in a microwave at 120° C. for 10 min (×2). Ethyl acetate (10 mL) was added and the mixture washed with water (2×5 mL). The organic layer was dried over MgSO₄, filtered and the solvent removed in vacuo. The residue was purified by normal phase chromatography, eluting with a gradient of 0-30% ethyl acetate in cyclohexane and then further purified by MDAP (acidic conditions), to give the title compound (16 mg). LCMS (A) m/z: 449 [M+1]⁺, Rt 1.54 min (acidic).

Example 66

3-Chloro-N-[2,6-dimethyl-3-(4-methyl-2-thienyl)thieno[2,3-b]pyridin-4-yl]benzenesulfonamide

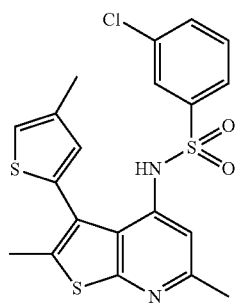

Under nitrogen, N-(3-bromo-2,6-dimethylthieno[2,3-b]pyridin-4-yl)-3-chlorobenzenesulfonamide (Example 61) (100 mg, 0.232 mmol) was dissolved in 1,4-dioxane (2 mL) and water (0.7 mL). 4,4,5,5-Tetramethyl-2-(4-methyl-2-thienyl)-1,3,2-dioxaborolane (78 mg, 0.347 mmol), tetrakis(triphenylphosphine)palladium(0) (26.8 mg, 0.023 mmol) and potassium carbonate (96 mg, 0.695 mmol) were added and the mixture heated in a microwave at 120° C. for 15 min. Ethyl acetate (10 mL) was added and the mixture washed with water (2×5 mL). The organic layer was dried over MgSO₄, filtered and the solvent removed in vacuo. The residue was purified by normal phase chromatography, eluting with a gradient of 0-30% ethyl acetate in cyclohexane and further triturated with MeOH, to give the title compound (37.7 mg). LCMS (A) m/z: 449 [M+1]⁺, Rt 1.53 min (acidic).

Example 67

3-Chloro-N-{2,6-dimethyl-3-[5-(methyloxy)-3-pyridinyl]thieno[2,3-b]pyridin-4-yl}benzenesulfonamide

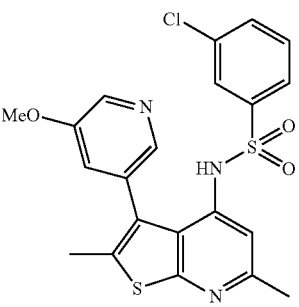

Under nitrogen, N-(3-bromo-2,6-dimethylthieno[2,3-b]pyridin-4-yl)-3-chlorobenzenesulfonamide (Example 61) (65 mg, 0.151 mmol) was dissolved in 1,4-dioxane (1.5 mL) and water (0.7 mL). 3-(Methyloxy)-5-(4,4,5,5-tetramethyl-1,3,2-dioxaborolan-2-yl)pyridine (53.1 mg, 0.226 mmol), tetrakis(triphenylphosphine)palladium(0) (17.40 mg, 0.015 mmol) and potassium carbonate (62.4 mg, 0.452 mmol) were added and the mixture heated in a microwave at 120° C. for 10 min. Ethyl acetate (10 mL) was then added and the mixture washed with water (2×5 mL). The organic layer was dried over MgSO₄, filtered and the solvent removed in vacuo. The residue was purified by normal phase chromatography, eluting with a gradient of 0-5% MeOH in DCM, and then further purified by MDAP (acidic conditions), to give the title compound (17.2 mg). LCMS (A) m/z: 460 [M+1]⁺, Rt 0.90 min (acidic).

Example 68

3-Chloro-N-{2,6-dimethyl-3-[6-(methyloxy)-2-pyridinyl]thieno[2,3-b]pyridin-4-yl}benzenesulfonamide

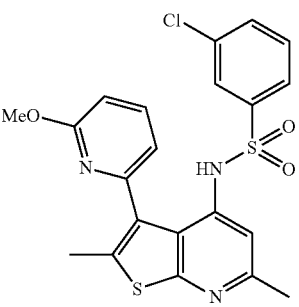

Under nitrogen, N-(3-bromo-2,6-dimethylthieno[2,3-b]pyridin-4-yl)-3-chlorobenzenesulfonamide (Example 61)

(65 mg, 0.151 mmol) was dissolved in 1,4-dioxane (1.5 mL) and water (0.7 mL). 2-(Methyloxy)-6-(4,4,5,5-tetramethyl-1,3,2-dioxaborolan-2-yl)pyridine (53.1 mg, 0.226 mmol), tetrakis(triphenylphosphine)palladium(0) (17.40 mg, 0.015 mmol) and potassium carbonate (62.4 mg, 0.452 mmol) were then added and the mixture heated in a microwave at 120° C. for 15 min (×2). Ethyl acetate (10 mL) was added and the mixture washed with water (2×5 mL). The organic layer was dried over MgSO₄, filtered and the solvent removed in vacuo. The residue was purified by normal phase chromatography, eluting with a gradient of 0-30% ethyl acetate in cyclohexane, and then further purified by MDAP (acidic conditions), to give the title compound (8.9 mg). LCMS (A) m/z: 460 [M+1]⁺, Rt 1.45 min (acidic).

Example 69

3-Chloro-N-[2,6-dimethyl-3-(3-methylphenyl)thieno[2,3-b]pyridin-4-yl]benzenesulfonamide

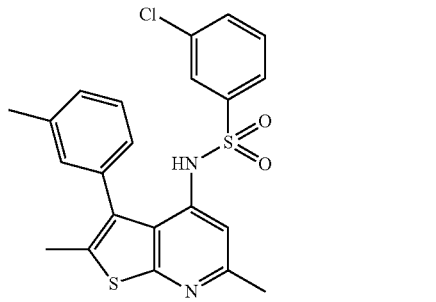 [SMILES: Cc1cccc(-c2c(C)sc3nc(C)cc(NS(=O)(=O)c4cccc(Cl)c4)c23)c1]

Under nitrogen, N-(3-bromo-2,6-dimethylthieno[2,3-b]pyridin-4-yl)-3-chlorobenzenesulfonamide (Example 61) (85 mg, 0.197 mmol) was dissolved in 1,4-dioxane (1.5 mL) and water (0.5 mL). (3-Methylphenyl)boronic acid (40.1 mg, 0.295 mmol), tetrakis(triphenylphosphine)palladium(0) (22.75 mg, 0.020 mmol) and potassium carbonate (54.4 mg, 0.394 mmol) were then added and the mixture heated in a microwave at 120° C. for 15 min. Ethyl acetate (10 mL) was added and the mixture washed with water (2×5 mL). The organic layer was then dried over MgSO₄, filtered and the solvent removed in vacuo. The residue was purified by normal phase chromatography, eluting with a gradient of 0-30% ethyl acetate in cyclohexane, to give the title compound (58.6 mg). LCMS (A) m/z: 443 [M+1]⁺, Rt 1.53 min (acidic).

Example 70

1,1-Dimethylethyl {[3-(4-{[(3-chlorophenyl)sulfonyl]amino}-2,6-dimethylthieno[2,3-b]pyridin-3-yl)phenyl]methyl}carbamate

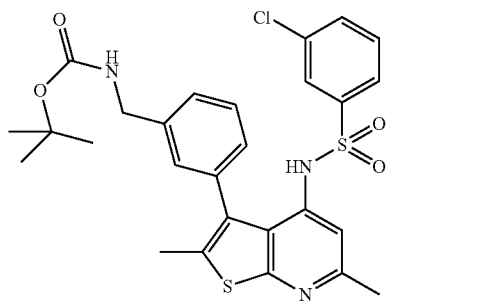 [SMILES: Cc1cc(NS(=O)(=O)c2cccc(Cl)c2)c2c(-c3cccc(CNC(=O)OC(C)(C)C)c3)c(C)sc2n1]

Under nitrogen, N-(3-bromo-2,6-dimethylthieno[2,3-b]pyridin-4-yl)-3-chlorobenzenesulfonamide (Example 61) (85 mg, 0.197 mmol) was dissolved in 1,4-dioxane (1.5 mL) and water (0.5 mL). 1,1-Dimethylethyl {[3-(4,4,5,5-tetramethyl-1,3,2-dioxaborolan-2-yl)phenyl]methyl}carbamate (98 mg, 0.295 mmol), tetrakis(triphenylphosphine)palladium (0) (22.75 mg, 0.020 mmol) and potassium carbonate (54.4 mg, 0.394 mmol) were added and the mixture heated in a microwave at 100° C. for 10 min (×2). Ethyl acetate (10 mL) was then added and the mixture washed with water (2×5 mL). The organic layer was then dried over MgSO₄, filtered and the solvent removed in vacuo. The residue was purified by normal phase chromatography, eluting with a gradient of 0-30% ethyl acetate in cyclohexane and then further purified by normal phase chromatography, eluting with ethyl acetate and cyclohexane (0-30%), to give the title compound (52 mg). LCMS (A) m/z: 558 [M+1]⁺, Rt 1.47 min (acidic).

Example 71

N-{3-[3-(Aminomethyl)phenyl]-2,6-dimethylthieno[2,3-b]pyridin-4-yl}-3-chlorobenzenesulfonamide

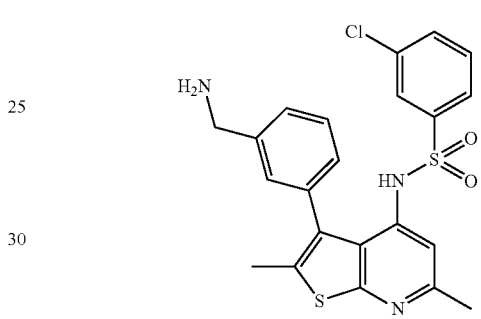

To a solution of 1,1-dimethylethyl {[3-(4-{[(3-chlorophenyl)sulfonyl]amino}-2,6-dimethylthieno[2,3-b]pyridin-3-yl)phenyl]methyl}carbamate (Example 70) (40 mg, 0.072 mmol) in DCM (2 mL) was added TFA (0.276 mL, 3.58 mmol) and the mixture stirred for 1 h. The mixture was then loaded onto an SCX cartridge and flushed with MeOH (3×5 mL) followed by 2M NH₃ in MeOH (3×5 mL). The desired fractions were combined and concentrated and further purified by normal phase chromatography, eluting with a gradient of 0-20% 2M NH₃ in MeOH in DCM, to give the title compound (2.8 mg). LCMS (A) m/z: 458 [M+1]⁺, Rt 0.96 min (basic).

Example 72

3-Chloro-N-(3-{3-[(dimethylamino)methyl]phenyl}-2,6-dimethylthieno[2,3-b]pyridin-4-yl)benzenesulfonamide

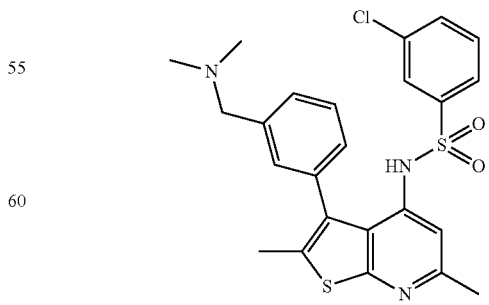

Under nitrogen, N-(3-bromo-2,6-dimethylthieno[2,3-b]pyridin-4-yl)-3-chlorobenzene sulfonamide (Example 61) (80 mg, 0.185 mmol) was dissolved in 1,4-dioxane (1.5 mL)

and water (0.5 mL). N,N-Dimethyl-1-[3-(4,4,5,5-tetramethyl-1,3,2-dioxaborolan-2-yl)phenyl]methanamine hydrochloride (83 mg, 0.278 mmol), tetrakis(triphenylphosphine)palladium(0) (21.41 mg, 0.019 mmol) and potassium carbonate (51.2 mg, 0.371 mmol) were added and heated in a microwave at 120° C. for 15 min. Ethyl acetate (10 mL) was added and washed with water (2×5 mL). The organic layer was dried over MgSO$_4$, filtered and solvent removed in vacuo. The residue was purified by normal phase chromatography, eluting with a gradient of 0-20% 2M NH$_3$ in MeOH in DCM, to give the title compound (15.3 mg). LCMS (A) m/z: 486 [M+1]$^+$, Rt 0.92 min (acidic).

Example 73

3-Chloro-N-(3-cyano-2,6-dimethylthieno[2,3-b]pyridin-4-yl)benzenesulfonamide

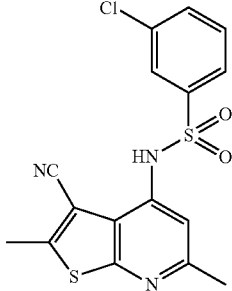 [SMILES: Cc1cc(NS(=O)(=O)c2cccc(Cl)c2)c2c(C#N)c(C)sc2n1]

To a solution of 4-amino-2,6-dimethylthieno[2,3-t]pyridine-3-carbonitrile (Description 76) (236 mg, 1.161 mmol) in THF (6 mL) was added potassium tert-butoxide (521 mg, 4.64 mmol) and the mixture stirred for 5 min before adding 3-chlorobenzenesulfonyl chloride (0.409 mL, 2.90 mmol). The mixture was then stirred for 1 h and the solvent was then removed in vacuo. Ethyl acetate (30 mL) was added and the mixture washed with water (3×10 mL). The organic layer was dried over MgSO$_4$, filtered and the solvent removed in vacuo. The residue was purified by normal phase chromatography, eluting with a gradient of 0-70% ethyl acetate in cyclohexane and then further triturated with MeOH, to give the title compound (187.6 mg). LCMS (A) m/z: 378 [M+1]$^+$, Rt 1.07 min (acidic).

Example 74

4-{[(3-Chlorophenyl)sulfonyl]amino}-2,6-dimethylthieno[2,3-b]pyridine-3-carboxamide

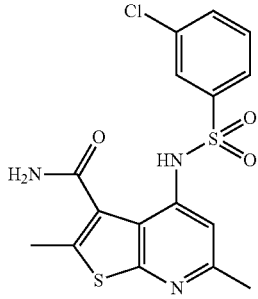 [SMILES: Cc1cc(NS(=O)(=O)c2cccc(Cl)c2)c2c(C(N)=O)c(C)sc2n1]

A mixture of 3-chloro-N-(3-cyano-2,6-dimethylthieno[2,3-b]pyridin-4-yl)benzenesulfonamide (Example 73) (119 mg, 0.315 mmol), DMSO (3 mL) and aqueous NaOH (3M) (1.05 mL, 3.15 mmol) was stirred at 150° C. for 5 h. The mixture was then cooled and acidified with 5M HCl to pH 3-4. Water (20 mL) was added and the mixture extracted with ethyl acetate (3×10 mL). The organic layer was then dried over MgSO$_4$, filtered and concentrated. The residue was purified by normal phase chromatography, eluting with a gradient of 0-10% MeOH in DCM, and then further triturated with MeOH, to give the title compound (69 mg). LCMS (A) m/z: 396 [M+1]$^+$, Rt 1.13 min (acidic).

Example 75

3-Chloro-N-[3-(1H-indol-6-yl)-2,6-dimethylthieno[2,3-b]pyridin-4-yl]benzenesulfonamide

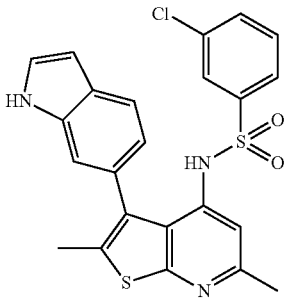 [SMILES: Cc1cc(NS(=O)(=O)c2cccc(Cl)c2)c2c(-c3ccc4cc[nH]c4c3)c(C)sc2n1]

Under nitrogen, N-(3-bromo-2,6-dimethylthieno[2,3-b]pyridin-4-yl)-3-chlorobenzenesulfonamide (Example 61) (16.6 mg, 0.038 mmol) was dissolved in 1,4-dioxane (0.6 mL) and water (0.2 mL). 1H-Indol-6-ylboronic acid (9.28 mg, 0.058 mmol), tetrakis(triphenylphosphine)palladium(0) (4.44 mg, 3.84 µmol) and potassium carbonate (10.63 mg, 0.077 mmol) were then added and the mixture heated in a microwave at 120° C. for 15 min. The crude mixture was purified by MDAP (acidic conditions) and then further purified by normal phase chromatography, eluting with a gradient of 0-30% ethyl acetate in cyclohexane, to give the title compound (3 mg). LCMS (A) m/z: 468 [M+1]$^+$, Rt 1.45 min (acidic).

Example 76

3-Chloro-N-[3,6-dimethyl-2-(1H-pyrazol-4-yl)thieno[2,3-b]pyridin-4-yl]benzenesulfonamide

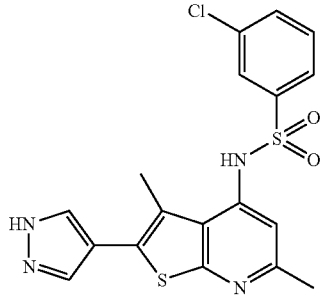 [SMILES: Cc1cc(NS(=O)(=O)c2cccc(Cl)c2)c2c(C)c(-c3cn[nH]c3)sc2n1]

A mixture of ethyl 4-{[(3-chlorophenyl)sulfonyl]amino}-3,6-dimethyl-2-(1H-pyrazol-4-yl)thieno[2,3-b]pyridine-5-carboxylate (Description 64) (150 mg, 0.306 mmol) in DMSO (5 mL) and aqueous NaOH (2M) (0.611 mL, 3.06 mmol) was heated at 150° C. for ca. 1.5 h. After cooling to RT, the mixture was diluted with water (20 mL), acidified with formic acid (ca. pH 4-5) and extracted with 10% MeOH in DCM (30 mL×5). The combined organics were dried and concentrated. The residue was passed through a C18 solid phase extractor cartridge, eluting with water (30 mL×4) and then with MeOH (30 mL×4) and the combined organics concentrated. The residue was taken-up in diphenyl ether (2 mL, 12.57 mmol) and DMSO (0.5 mL) and the mixture was heated at 200° C. for ca. 45 min. After cooling to RT, the mixture was purified by normal phase chromatography, eluting with a gradient of 0-100% ethyl acetate in cyclohexane and then with 0-20% MeOH in DCM and then further purified by MDAP (acidic conditions), to give the title compound (12 mg). LCMS (A) m/z: 419 [M+1]$^+$, Rt 1.04 min (acidic).

Example 77

N-(2-Bromo-3,6-dimethylthieno[2,3-b]pyridin-4-yl)-3-chlorobenzenesulfonamide

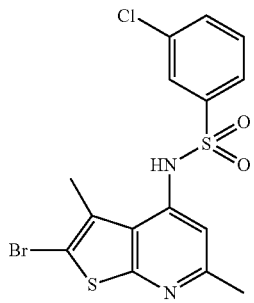 [SMILES: Cc1cc(NS(=O)(=O)c2cccc(Cl)c2)c2c(C)c(Br)sc2n1]

To a solution of 2-bromo-3,6-dimethylthieno[2,3-b]pyridin-4-amine (Description 62) (1.351 g, 5.25 mmol) in THF (10 mL) was added 3-chlorobenzenesulfonyl chloride (1.11 mL, 7.88 mmol), sodium tert-butoxide (1.262 g, 13.13 mmol) and the mixture stirred at RT for 16 h. The mixture was then evaporated to dryness and the resulting material taken-up in water (10 mL) and extracted with ethyl acetate (20 mL×3). The organics were then combined, dried (phase separation cartridge) and concentrated. Purification on silica, eluting with a gradient of 0-20% ethyl acetate in cyclohexane, followed by MDAP (acidic conditions), afforded the title compound (380 mg). LCMS (A) m/z: 431/433 [M+1]$^+$, Rt 1.22 min (acidic).

Example 78

3-Chloro-N-{3,6-dimethyl-2-[3-(methyloxy)phenyl]thieno[2,3-b]pyridin-4-yl}benzenesulfonamide

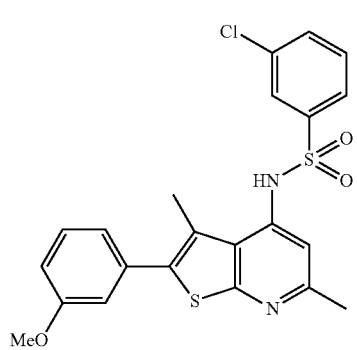 [SMILES: COc1cccc(-c2sc3nc(C)cc(NS(=O)(=O)c4cccc(Cl)c4)c3c2C)c1]

To a solution of N-(2-bromo-3,6-dimethylthieno[2,3-b]pyridin-4-yl)-3-chlorobenzenesulfonamide (Example 77) (100 mg, 0.232 mmol) in water (1 mL) and 1,4-dioxane (2 mL) was added [3-(methyloxy)phenyl]boronic acid (52.8 mg, 0.347 mmol), bis(triphenylphosphine)palladium(II) chloride (16.26 mg, 0.023 mmol), potassium carbonate (96 mg, 0.695 mmol) and the mixture heated to 100° C. for 15 min using a microwave reactor. The mixture was then filtered through celite, washing with ethyl acetate (30 mL) and DCM (20 mL). The organics were then combined, dried (phase separation cartridge) and concentrated. The residue was then purified by MDAP (basic conditions), to afford the title compound (36.8 mg). LCMS (A) m/z: 459 [M+1]$^+$, Rt 1.32 min (acidic).

Example 79

N-[2-(1-Benzofuran-2-yl)-3,6-dimethylthieno[2,3-b]pyridin-4-yl]-3-chlorobenzenesulfonamide

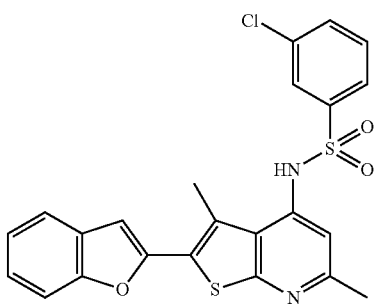 [SMILES: Cc1cc(NS(=O)(=O)c2cccc(Cl)c2)c2c(C)c(-c3cc4ccccc4o3)sc2n1]

To solution of N-(2-bromo-3,6-dimethylthieno[2,3-b]pyridin-4-yl)-3-chlorobenzenesulfonamide (Example 77) (100 mg, 0.232 mmol) in 1,4-dioxane (2 mL) and water (1 mL) was added 1-benzofuran-2-ylboronic acid (56.3 mg, 0.347 mmol), bis(triphenylphosphine)palladium(II) chloride (16.26 mg, 0.023 mmol) and potassium carbonate (112 mg, 0.811 mmol) and the reaction mixture heated at 100° C. using a microwave reactor for 30 min. The mixture was then filtered through celite, washing with DCM (20 mL×2) and the filtrate dried (phase separation cartridge) and concentrated. The residue was then purified by MDAP (acidic conditions), followed by MDAP (basic conditions) to afford the title compound (10.89 mg). LCMS (A) m/z: 469 [M+1]$^+$, Rt 1.42 min (acidic).

Example 80

3-Chloro-N-[3,6-dimethyl-2-(3-quinolinyl)thieno[2,3-b]pyridin-4-yl]benzenesulfonamide

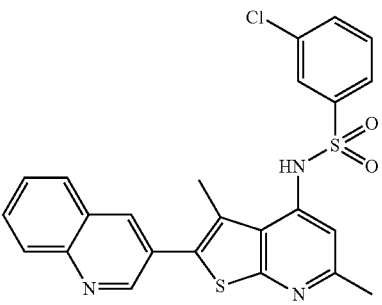 [SMILES: Cc1cc(NS(=O)(=O)c2cccc(Cl)c2)c2c(C)c(-c3cnc4ccccc4c3)sc2n1]

To a solution of N-(2-bromo-3,6-dimethylthieno[2,3-b]pyridin-4-yl)-3-chlorobenzenesulfonamide (Example 77) (90 mg, 0.208 mmol) in 1,4-dioxane (2 mL) and water (1 mL) was added 3-quinolinylboronic acid (72.1 mg, 0.417 mmol), bis (triphenylphosphine)palladium(II) chloride (14.63 mg, 0.021 mmol) and potassium carbonate (101 mg, 0.730 mmol) and

Example 81

3-Chloro-N-[3,6-dimethyl-2-(1H-pyrazol-3-yl)thieno[2,3-b]pyridin-4-yl]benzenesulfonamide

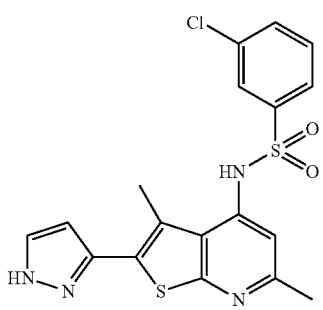 [SMILES: Cc1cc(NS(=O)(=O)c2cccc(Cl)c2)c2c(C)c(-c3cc[nH]n3)sc2n1]

To a solution of N-(2-bromo-3,6-dimethylthieno[2,3-b]pyridin-4-yl)-3-chlorobenzenesulfonamide (Example 77) (80 mg, 0.185 mmol), 1H-pyrazol-3-ylboronic acid (20.73 mg, 0.185 mmol) and bis(triphenylphosphine)palladium(II) chloride (13.01 mg, 0.019 mmol) in 1,4-dioxane (2 mL) and water (1 mL) was added potassium carbonate (90 mg, 0.649 mmol) and the mixture heated to 100° C. using a microwave reactor for 30 min. The mixture was then evaporated to dryness and purified by MDAP (acidic conditions), followed by MDAP (basic conditions), to afford the title compound (8.07 mg). LCMS (A) m/z: 417 [M−1]⁻, Rt 0.99 min (acidic).

Example 82

3-Chloro-N-(2-cyano-3,6-dimethylthieno[2,3-b]pyridin-4-yl)benzenesulfonamide

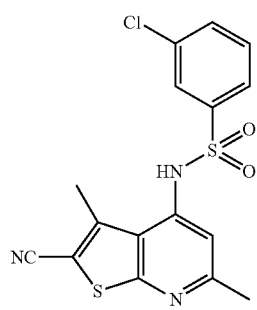 [SMILES: Cc1cc(NS(=O)(=O)c2cccc(Cl)c2)c2c(C)c(C#N)sc2n1]

To a solution of N-(2-bromo-3,6-dimethylthieno[2,3-b]pyridin-4-yl)-3-chlorobenzenesulfonamide (Example 77) (100 mg, 0.232 mmol) in 1-methylimidazole (1.5 mL, 18.82 mmol) was added potassium ferrocyanide (17.06 mg, 0.046 mmol) and copper(I) iodide (4.41 mg, 0.023 mmol) and the reaction stirred at 160° C. for 16 h. The reaction mixture was then cooled to RT before directly purifying on silica, eluting with a gradient of 0-20% 2M NH₃ in MeOH in DCM. Further purification by MDAP (acidic conditions), afforded the title compound (25.1 mg). LCMS (A) m/z: 378 [M+1]⁺, Rt 1.10 min (acidic).

Example 83

3-Chloro-N-[2-(4-isoxazolyl)-3,6-dimethylthieno[2,3-b]pyridin-4-yl]benzenesulfonamide

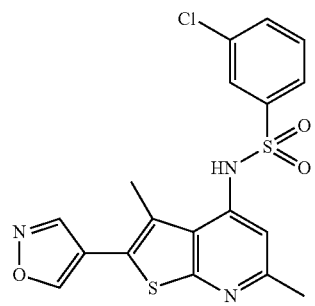 [SMILES: Cc1cc(NS(=O)(=O)c2cccc(Cl)c2)c2c(C)c(-c3cnoc3)sc2n1]

To a solution of N-(2-bromo-3,6-dimethylthieno[2,3-b]pyridin-4-yl)-3-chlorobenzenesulfonamide (Example 77) (80 mg, 0.185 mmol) in 1,4-dioxane (2 mL) and water (1 mL) was added 4-(4,4,5,5-tetramethyl-1,3,2-dioxaborolan-2-yl)isoxazole (36.1 mg, 0.185 mmol), bis(triphenylphosphine)palladium(II) chloride (13.01 mg, 0.019 mmol), and potassium carbonate (90 mg, 0.649 mmol) and the reaction mixture heated at 100° C. using a microwave reactor for 1.5 h. The reaction mixture was then filtered through celite, washing with DCM (30 mL) and the filtrate evaporated to dryness. The resulting material was then purified by MDAP (acidic conditions), to afford the title compound (4.67 mg). LCMS (A) m/z: 420 [M+1]⁺, Rt 1.09 min (acidic).

Example 84

3-Chloro-N-[2-(4-isoquinolinyl)-3,6-dimethylthieno[2,3-b]pyridin-4-yl]benzenesulfonamide

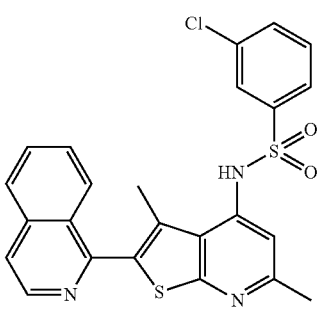 [SMILES: Cc1cc(NS(=O)(=O)c2cccc(Cl)c2)c2c(C)c(-c3nccc4ccccc34)sc2n1]

To a solution of N-(2-bromo-3,6-dimethylthieno[2,3-b]pyridin-4-yl)-3-chlorobenzenesulfonamide (Example 77) (100 mg, 0.232 mmol) in 1,4-dioxane (2 mL) and water (1 mL) was added 4-isoquinolinylboronic acid (40.1 mg, 0.232 mmol), bis(triphenylphosphine)palladium(II) chloride (16.26 mg, 0.023 mmol) and potassium carbonate (112 mg, 0.811 mmol) and the mixture heated at 100° C. for 1 h using a microwave reactor. The mixture was then filtered through celite, washing with ethyl acetate (30 mL) and the filtrate evaporated to

Example 85

3-Chloro-N-{2-(3-hydroxy-1-propyn-1-yl)-6-methyl-3-[3-(methyloxy)phenyl]thieno[2,3-b]pyridin-4-yl}benzenesulfonamide

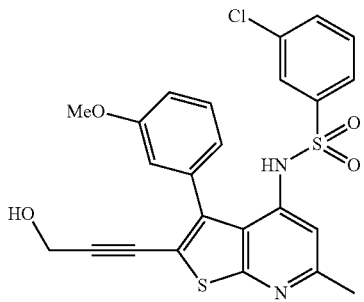 [SMILES: COc1cccc(-c2c(C#CCO)sc3nc(C)cc(NS(=O)(=O)c4cccc(Cl)c4)c23)c1]

A mixture of N-{2-bromo-6-methyl-3-[3-(methyloxy)phenyl]thieno[2,3-b]pyridin-4-yl}-3-chlorobenzenesulfonamide (Example 33) (195 mg, 0.372 mmol), propargyl alcohol (0.033 mL, 0.558 mmol), copper(I) iodide (7.09 mg, 0.037 mmol), bis(triphenylphosphine)palladium(II) chloride (10.45 mg, 0.015 mmol) and triethylamine (0.156 mL, 1.117 mmol) in THF (1.7 mL) was stirred under an atmosphere of nitrogen at 70° C. for 3 h. The mixture was allowed to cool to RT, with stirring, over the weekend. The mixture was then partitioned between a saturated aqueous solution of NaHCO₃ (25 mL) and ethyl acetate (50 mL). The aqueous phase was separated and extracted with additional ethyl acetate (25 mL). The organic extracts were combined, washed with brine (25 mL), dried with anhydrous MgSO₄, filtered and evaporated to dryness. The residue was purified on silica, eluting with a gradient of 0-100% cyclohexane in ethyl acetate. Further purification on silica, eluting with 0-50% cyclohexane in ethyl acetate, afforded the title compound (14 mg) LCMS (A) m/z: 499 [M+1]⁺, Rt 1.24 min (acidic).

Example 86

3-Chloro-N-{6-methyl-3-[3-(methyloxy)phenyl]-2-[3-(4-morpholinyl)-1-propyn-1-yl]thieno[2,3-b]pyridin-4-yl}benzenesulfonamide

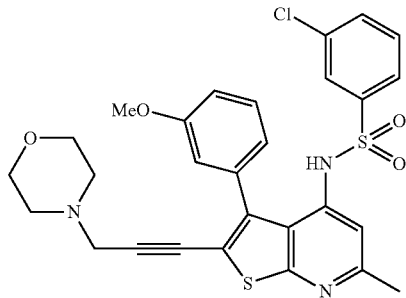 [SMILES: COc1cccc(-c2c(C#CCN3CCOCC3)sc3nc(C)cc(NS(=O)(=O)c4cccc(Cl)c4)c23)c1]

A mixture of 3-{4-{[(3-chlorophenyl)sulfonyl]amino}-6-methyl-3-[3-(methyloxy)phenyl]thieno[2,3-b]pyridin-2-yl}-2-propyn-1-yl methanesulfonate (Description 77) (14 mg, 0.024 mmol) and morpholine (21.14 µl, 0.243 mmol) in THF (221 µl) was stirred at 60° C. for 1 h. The mixture was evaporated to dryness and the residue purified on silica, eluting with a gradient of 0-10% 2M NH₃ in MeOH in DCM, to afford the title compound (12 mg). LCMS (A) m/z: 568 [M+1]⁺, Rt 1.02 min (acidic).

Example 87

3-Chloro-N-{6-methyl-3-[3-(methyloxy)phenyl]-2-[3-(4-morpholinyl)propyl]thieno[2,3-b]pyridin-4-yl}benzenesulfonamide

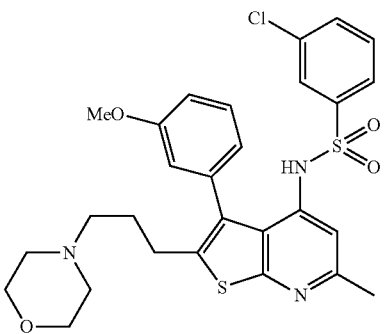 [SMILES: COc1cccc(-c2c(CCCN3CCOCC3)sc3nc(C)cc(NS(=O)(=O)c4cccc(Cl)c4)c23)c1]

A mixture of 3-chloro-N-{6-methyl-3-[3-(methyloxy)phenyl]-2-[3-(4-morpholinyl)-1-propyn-1-yl]thieno[2,3-b]pyridin-4-yl}benzenesulfonamide (Example 86) (6.8 mg, 0.012 mmol) and palladium on carbon (2.55 mg, 2.394 µmol) in ethanol (2.0 mL) was stirred under an atmosphere of hydrogen at RT for 20 h. The mixture was then filtered through celite, washing with ethanol, and evaporated to dryness. The residue was purified on silica, eluting with a gradient of 0-10% MeOH in DCM to afford the title compound (1.9 mg). 1H NMR (MeOD, 400 MHz) δ ppm: 1.76 (2H, m), 2.27-2.40 (6H, m), 2.54 (3H, s), 2.69 (2H, m), 3.61 (4H, m), 3.84 (3H, s), 6.76-6.81 (2H, m), 7.04-7.10 (1H, m), 7.27 (1H, s), 7.39-7.48 (3H, m), 7.52-7.60 (2H, m).

Example 88

3-Chloro-N-{2-[3-(dimethylamino)-1-propyn-1-yl]-6-methyl-3-[3-(methyloxy)phenyl]thieno[2,3-b]pyridin-4-yl}benzenesulfonamide

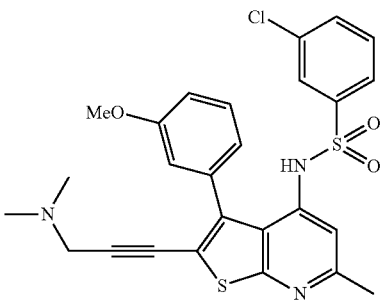 [SMILES: COc1cccc(-c2c(C#CCN(C)C)sc3nc(C)cc(NS(=O)(=O)c4cccc(Cl)c4)c23)c1]

A mixture of N-{2-bromo-6-methyl-3-[3-(methyloxy)phenyl]thieno[2,3-b]pyridin-4-yl}-3-chlorobenzenesulfonamide (Example 33) (122 mg, 0.233 mmol), N,N-dimethyl-2-propyn-1-amine (0.037 mL, 0.349 mmol), copper(I) iodide (4.44 mg, 0.023 mmol), bis(triphenylphosphine)palladium(II) chloride (6.54 mg, 9.32 µmol) and triethylamine (0.097 mL, 0.699 mmol) in THF (1.0 mL) was stirred under an atmosphere of nitrogen at 70° C. for 3 h. The mixture was allowed to cool to RT and was then partitioned between saturated aqueous NaHCO₃ (25 mL) and ethyl acetate (75 mL). The aqueous phase was separated and extracted with additional ethyl acetate (25 mL). The organic extracts were combined, washed with brine (25 mL), dried with anhydrous MgSO₄, filtered and evaporated to dryness. The residue was purified on silica, eluting with a gradient of 0-10% MeOH in DCM, and then further purified on silica, eluting with a gradient of 0-10% 2M NH₃ in MeOH in DCM to afford the title compound (4.9 mg). ¹H NMR (MeOD, 400 MHz) δ ppm: 2.42 (6H, s), 2.55 (3H, s), 3.80 (5H, s), 6.89 (2H, m), 7.01 (1H, d, J=7.7 Hz), 7.26 (1H, s), 7.32-7.48 (3H, m), 7.49-7.60 (2H, m).

Example 89

3-Chloro-N-[6-methyl-3-[3-(methyloxy)phenyl]-2-(1-methyl-1H-pyrazol-4-yl)thieno[2,3-b]pyridin-4-yl]benzenesulfonamide

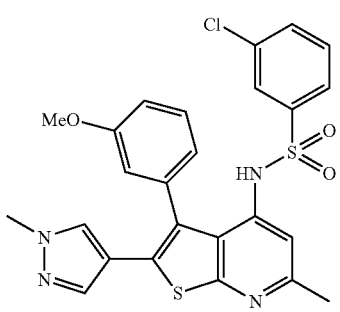 [SMILES: COc1cccc(-c2c(-c3cnn(C)c3)sc3nc(C)cc(NS(=O)(=O)c4cccc(Cl)c4)c23)c1]

A mixture of N-{2-bromo-6-methyl-3-[3-(methyloxy)phenyl]thieno[2,3-b]pyridin-4-yl}-3-chlorobenzenesulfonamide (Example 33) (50 mg, 0.095 mmol), tetrakis(triphenylphosphine)palladium(0) (5.51 mg, 4.77 µmol), sodium carbonate (20.23 mg, 0.191 mmol) and (1-methyl-1H-pyrazol-4-yl)boronic acid (12.02 mg, 0.095 mmol) in acetonitrile (1 mL) and water (0.250 mL) was heated at 80° C. under nitrogen, overnight (ca. 18 h). The reaction mixture was then cooled to RT and concentrated. The residue was purified by chromatography on silica, eluting with a gradient of 0-50% ethyl acetate in DCM, to give the title compound (17.5 mg). LCMS (A) m/z: 525 [M+1]⁺, Rt 1.34 min (acidic).

Example 90

3-Chloro-N-[6-methyl-3-[3-(methyloxy)phenyl]-2-(1H-pyrazol-3-yl)thieno[2,3-b]pyridin-4-yl]benzenesulfonamide

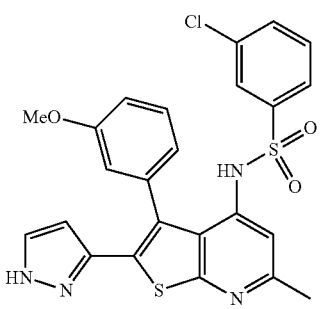 [SMILES: COc1cccc(-c2c(-c3cc[nH]n3)sc3nc(C)cc(NS(=O)(=O)c4cccc(Cl)c4)c23)c1]

To a solution of N-{2-bromo-6-methyl-3-[3-(methyloxy)phenyl]thieno[2,3-b]pyridin-4-yl}-3-chlorobenzenesulfonamide (Example 33) (160 mg, 0.305 mmol) in 1,4-dioxane (2.5 mL) was added 1H-pyrazol-3-ylboronic acid (51.3 mg, 0.458 mmol), bis(triphenylphosphine)palladium(II) chloride (21.44 mg, 0.031 mmol) and potassium carbonate (127 mg, 0.916 mmol). Then, water (1 mL) was added to the mixture. The reaction mixture was then heated at 100° C. in a microwave for 15 min (×2). Extra tetrakis(triphenylphosphine)palladium(0) (35.3 mg, 0.031 mmol) was added and the mixture heated at 100° C. for another 15 min. The solvent from was then removed in vacuo and the residue dissolved in ethyl acetate (20 mL) and washed with water (20 mL). The aqueous phase was re-extracted with ethyl acetate (20 mL×2). All organic phase were combined, dried over MgSO₄, filtered and the solvent removed in vacuo. The residue was purified on silica, eluting with a gradient of 0-50% ethyl acetate in cyclohexane and further purified using MDAP (acidic conditions), to give the title compound (16 mg). LCMS (A) m/z: 509 [M−1]⁻, Rt 1.23 min (acidic).

Example 91

3-Chloro-N-{2-(4-isoxazolyl)-6-methyl-3-[3-(methyloxy)phenyl]thieno[2,3-b]pyridin-4-yl}benzenesulfonamide

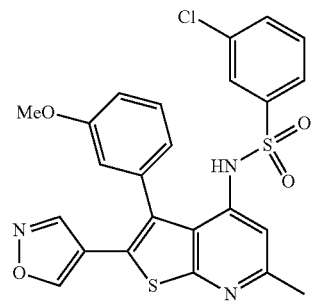 [SMILES: COc1cccc(-c2c(-c3cnoc3)sc3nc(C)cc(NS(=O)(=O)c4cccc(Cl)c4)c23)c1]

To a solution of N-{2-bromo-6-methyl-3-[3-(methyloxy)phenyl]thieno[2,3-b]pyridin-4-yl}-3-chlorobenzenesulfonamide (Example 33) (100 mg, 0.191 mmol) in 1,4-dioxane (2 mL) was added 4-(4,4,5,5-tetramethyl-1,3,2-dioxaborolan-2-yl)isoxazole (55.8 mg, 0.286 mmol), potassium carbonate (79 mg, 0.573 mmol) and bis(triphenylphosphine)palladium (II) chloride (13.40 mg, 0.019 mmol). Water (0.5 mL) was then added and the mixture heated at 100° C. in a microwave for 15 min. The solvent was then removed in vacuo and the residue dissolved in ethyl acetate (20 mL) and washed with water (20 mL). The aqueous phase was re-extracted with ethyl acetate (2×20 mL). All organic phases were combined, dried over MgSO₄, filtered and concentrated. The residue was purified on silica, eluting with a gradient of 0-40% ethyl acetate in cyclohexane, to give the title compound (22 mg). LCMS (A) m/z: 512 [M+1]⁺, Rt 1.36 min (acidic).

Example 92

3-Chloro-N-[6-methyl-3-[3-(methyloxy)phenyl]-2-(3-methyl-1H-pyrazol-4-yl)thieno[2,3-b]pyridin-4-yl]benzenesulfonamide

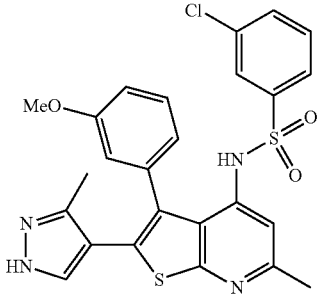 [SMILES: COc1cccc(-c2c(-c3c[nH]nc3C)sc3nc(C)cc(NS(=O)(=O)c4cccc(Cl)c4)c23)c1]

To a solution of N-{2-bromo-6-methyl-3-[3-(methyloxy)phenyl]thieno[2,3-b]pyridin-4-yl}-3-chlorobenzenesulfonamide (Example 33) (100 mg, 0.191 mmol) in 1,4-dioxane (2 mL) was added 3-methyl-4-(4,4,5,5-tetramethyl-1,3,2-dioxaborolan-2-yl)-1H-pyrazole (59.6 mg, 0.286 mmol), bis(triphenylphosphine)palladium(II) chloride (13.40 mg, 0.019 mmol) and potassium carbonate (79 mg, 0.573 mmol). Water (1 mL) was added and the mixture heated at 100° C. in a microwave for 15 min (×2). The solvent was removed in vacuo and the residue dissolved in ethyl acetate (20 mL) and washed with water (20 mL). The aqueous phase re-extracted with ethyl acetate (2×20 mL). All organic phases were combined, dried over MgSO₄, filtered and concentrated. The residue was purified on silica, eluting with a gradient of 0-80% ethyl acetate in cyclohexane and then further purified using MDAP (acidic conditions), to give the title compound (15 mg). LCMS (A) m/z: 525 [M+1]⁺, Rt 1.23 min (acidic).

Example 93

3-Chloro-N-{2-(3,5-dimethyl-1H-pyrazol-4-yl)-6-methyl-3-[3-(methyloxy)phenyl]thieno[2,3-b]pyridin-4-yl}benzenesulfonamide

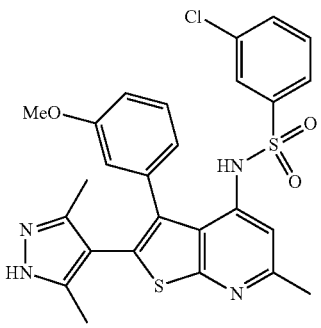 [SMILES: COc1cccc(-c2c(-c3c(C)n[nH]c3C)sc3nc(C)cc(NS(=O)(=O)c4cccc(Cl)c4)c23)c1]

To a solution of N-{2-bromo-6-methyl-3-[3-(methyloxy)phenyl]thieno[2,3-b]pyridin-4-yl}-3-chlorobenzenesulfonamide (Example 33) (140 mg, 0.267 mmol) in 1,4-dioxane (2 mL) was added 3,5-dimethyl-4-(4,4,5,5-tetramethyl-1,3,2-dioxaborolan-2-yl)-1H-pyrazole (89 mg, 0.401 mmol), bis(triphenylphosphine)palladium(II) chloride (18.76 mg, 0.027 mmol) and potassium carbonate (111 mg, 0.802 mmol). Water (1 mL) was added and the mixture heated at 100° C. in a microwave for 15 min (×2). Another portion of bis(triphenylphosphine)palladium(II) chloride (18.76 mg, 0.027 mmol) was then added and the reaction mixture degassed with nitrogen for 5 min and then heated at 100° C. in a microwave for 15 min (×2). The solvent was then removed in vacuo and the residue dissolved in ethyl acetate (20 mL) and washed with water (20 mL). The aqueous phase was re-extracted with ethyl acetate (20 mL×2). All organic phases were combined, dried over MgSO₄, filtered and concentrated. The residue was purified on silica, eluting with a gradient of 0-80% ethyl acetate in cyclohexane and then further purified using MDAP (acidic conditions), to give the title compound (36 mg). LCMS (A) m/z: 539 [M+1]⁺, Rt 1.47 min (acidic).

Example 94

3-Chloro-N-[6-methyl-3-[3-(methyloxy)phenyl]-2-(4-pyridinyl)thieno[2,3-b]pyridin-4-yl]benzenesulfonamide

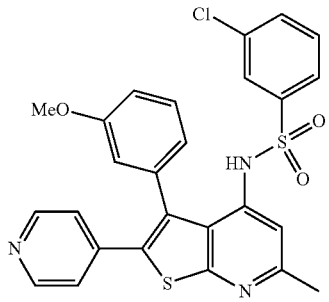 [SMILES: COc1cccc(-c2c(-c3ccncc3)sc3nc(C)cc(NS(=O)(=O)c4cccc(Cl)c4)c23)c1]

To a solution of N-{2-bromo-6-methyl-3-[3-(methyloxy)phenyl]thieno[2,3-b]pyridin-4-yl}-3-chlorobenzenesulfonamide (Example 33) (100 mg, 0.191 mmol) in 1,4-dioxane (2 mL) was added 4-(4,4,5,5-tetramethyl-1,3,2-dioxaborolan-2-yl)pyridine (58.7 mg, 0.286 mmol), bis(triphenylphosphine)palladium(II) chloride (13.40 mg, 0.019 mmol), potassium carbonate (79 mg, 0.573 mmol) and water (1 mL). The reaction mixture was heated at 100° C. in a microwave for 15 min (×2) and then for 30 min (×1). Another portion of 4-(4,4,5,5-tetramethyl-1,3,2-dioxaborolan-2-yl)pyridine (58.7 mg, 0.286 mmol) and additional bis(triphenylphosphine)palladium(II) chloride (13.40 mg, 0.019 mmol) were added and heating continued, at 100° C. in a microwave, for another 15 min. The solvent was then removed in vacuo and the residue dissolved in ethyl acetate (30 mL) and washed with water (30 mL). The aqueous phase was re-extracted with ethyl acetate (30 mL×2). All organic phases were combined, dried over MgSO₄, filtered and concentrated. The residue was purified on silica, eluting with a gradient of 0-50% ethyl acetate in cyclohexane and then further purified using MDAP (acidic conditions), to give the title compound (37 mg). LCMS (A) m/z: 520 [M−1]⁻, Rt 1.22 min (acidic).

Example 95

N-{2-Bromo-6-methyl-3-[3-(methyloxy)phenyl]thieno[2,3-b]pyridin-4-yl}cyclopropanesulfonamide

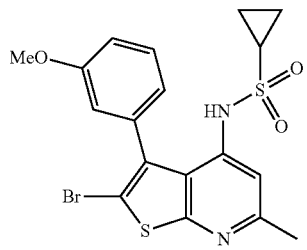 [SMILES: COc1cccc(-c2c(Br)sc3nc(C)cc(NS(=O)(=O)C4CC4)c23)c1]

To a stirred solution of 2-bromo-6-methyl-3-[3-(methyloxy)phenyl]thieno[2,3-b]pyridin-4-amine (Description 17) (303 mg, 0.868 mmol) in THF (5 mL) at RT, was added sodium tert-butoxide (214 mg, 2.227 mmol). The reaction mixture was stirred at RT for 15 min, followed by the addition of cyclopropanesulfonyl chloride (0.16 mL, 1.74 mmol). The reaction mixture was stirred at RT for 1.5 h, followed by the sequential of addition of DMF (2.5 mL), sodium tert-butoxide (202 mg) and cyclopropanesulfonyl chloride (0.16 mL, 1.741 mmol). The reaction mixture was stirred at RT for another 1.5 h, followed by the addition of water (25 mL) and ethyl acetate (25 mL). The aqueous layer was separated and extracted with ethyl acetate (3×25 mL). The combined organic extracts were washed with water (15 mL), dried (phase separating column) and concentrated to give a residue, which was purified on silica, eluting with a gradient of 0-75% ethyl acetate in cyclohexane, to give a residue (127 mg). Ca. 45 mg of this material was purified further by MDAP (acidic conditions) followed by trituration with diethyl ether, to give the title compound (9 mg). LCMS (A) m/z: 453/455 [M+1]$^+$, Rt 1.50 min (acidic).

Example 96

N-[6-Methyl-3-[3-(methyloxy)phenyl]-2-(1H-pyrazol-4-yl)thieno[2,3-b]pyridin-4-yl]cyclopropanesulfonamide

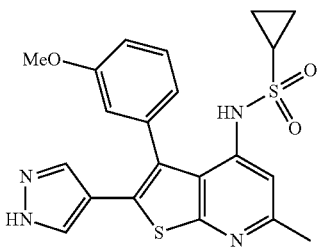 [SMILES: COc1cccc(-c2c(-c3cn[nH]c3)sc3nc(C)cc(NS(=O)(=O)C4CC4)c23)c1]

To a suspension of N-{2-bromo-6-methyl-3-[3-(methyloxy)phenyl]thieno[2,3-b]pyridin-4-yl}cyclopropanesulfonamide (Example 95) (58 mg, 0.128 mmol), K$_2$CO$_3$ (57 mg, 0.412 mmol) and 1H-pyrazol-4-ylboronic acid (30 mg, 0.268 mmol) in 1,4-dioxane (1 mL) and water (0.4 mL), was added tetrakis(triphenylphosphine)palladium(0) (15 mg, 0.013 mmol). The reaction mixture was heated at 130° C. in a microwave reactor for 1 h and was then directly loaded onto a silica column, eluting with a gradient of 0-75% of ethyl acetate in cyclohexane and further purified by MDAP (acidic then basic conditions) to give the desired product and a white solid thought to be a salt of the desired product. The solid material was subsequently dissolved in DCM (1 mL) and treated with acetic acid (ca. 0.5 mL). The solvent was then removed to give a residue which was combined with the initially obtained product and the mixture further purified on silica, eluting with a gradient of 0-75% ethyl acetate in cyclohexane, to give the title compound (18 mg). LCMS (A) m/z: 441 [M+1]$^+$, Rt 1.08 min (acidic).

Example 97

N-{2-Bromo-6-methyl-3-[3-(methyloxy)phenyl]thieno[2,3-b]pyridin-4-yl}methanesulfonamide

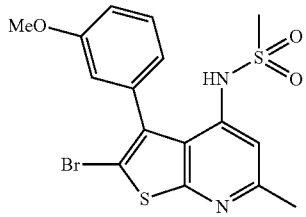 [SMILES: COc1cccc(-c2c(Br)sc3nc(C)cc(NS(C)(=O)=O)c23)c1]

To a stirred solution of 2-bromo-6-methyl-3-[3-(methyloxy)phenyl]thieno[2,3-b]pyridin-4-amine (Description 17) (277 mg, 0.793 mmol) in THF (2.5 mL) at RT, was added sodium tert-butoxide (220 mg, 2.289 mmol). The reaction mixture was stirred at RT for 15 min, followed by the addition of methane sulfonyl chloride (0.14 mL, 1.797 mmol). The reaction mixture was stirred at 1 h at RT, followed by the addition of DMF (2.5 mL), another portion of sodium tert-butoxide (203 mg, 2.112 mmol) and methane sulfonyl chloride (0.14 mL, 1.797 mmol). The reaction mixture was stirred for another 1 h at RT before the addition of water (20 mL) and ethyl acetate (20 mL). The aqueous layer was separated and extracted with ethyl acetate (3×25 mL). The combined organic extracts were washed with water (15 mL), dried (phase separating column) and concentrated to give a residue. Purification on silica (twice), eluting with a gradient of 0-75% ethyl acetate in cyclohexane afforded the title compound (109 mg) which was of sufficient purity for subsequent steps. In addition, some impure fractions were isolated and these were combined and further purified by MDAP (acidic conditions), to give an analytically pure sample of the title compound (9 mg). LCMS (A) m/z: 427/429 [M+1]$^+$, Rt 1.33 min (acidic).

Example 98

N-[6-Methyl-3-[3-(methyloxy)phenyl]-2-(1H-pyrazol-4-yl)thieno[2,3-b]pyridin-4-yl]methanesulfonamide

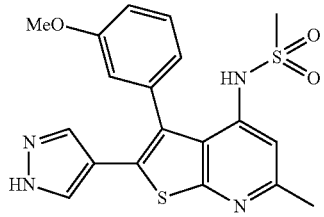 [SMILES: COc1cccc(-c2c(-c3cn[nH]c3)sc3nc(C)cc(NS(C)(=O)=O)c23)c1]

To a suspension of N-{2-bromo-6-methyl-3-[3-(methyloxy)phenyl]thieno[2,3-b]pyridin-4-yl}methanesulfonamide (Example 97) (109 mg, 0.255 mmol), 1H-pyrazol-4-ylboronic acid (60 mg, 0.536 mmol) and potassium carbonate (118 mg, 0.854 mmol) in 1,4-dioxane (1.5 mL) and water (0.6 mL), was added tetrakis(triphenylphosphine)palladium(0) (31 mg, 0.027 mmol). The reaction mixture was heated at 130° C. in a microwave reactor for 1 h, followed by the addition of another portion of 1H-pyrazol-4-ylboronic acid (41 mg, 0.366 mmol) and tetrakis(triphenylphosphine)palladium(0) (15 mg, 0.013 mmol). The reaction mixture was heated at 130° C. in a microwave reactor for another 1 h and was then directly loaded onto a silica column, eluting with a gradient of 0-75% of ethyl acetate in cyclohexane and then further purified by MDAP (acidic conditions), to give the title compound (36 mg). LCMS (A) m/z: 413 [M−1]$^-$, Rt 0.97 min (acidic).

Example 99

3-Chloro-N-[6-methyl-2-(1H-pyrazol-4-yl)thieno[2,3-b]pyridin-4-yl]benzenesulfonamide

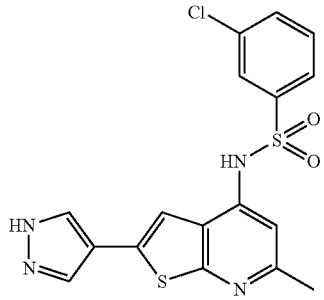 [SMILES: Cc1cc(NS(=O)(=O)c2cccc(Cl)c2)c2cc(-c3cn[nH]c3)sc2n1]

A mixture of ethyl 4-{[(3-chlorophenyl)sulfonyl]amino}-6-methyl-2-(1H-pyrazol-4-yl)thieno[2,3-b]pyridine-5-carboxylate (Description 73) (250 mg, 0.524 mmol) in DMSO (5 mL) and aqueous NaOH (2M) (1.048 mL, 5.24 mmol) was heated at 150° C. for ca. 1 h. After cooling to RT, the mixture was diluted with water (20 mL) and acidified with formic acid (pH ca. 4-5). The mixture was extracted with 10% MeOH in DCM (30 mL×5) and the combined organics dried and concentrated. The residue was passed through a C18 solid phase extractor cartridge, eluting with water (100 mL×4) and then with MeOH (100 mL×4) and the combined organics concentrated. The residue was taken-up in diphenyl ether (2.501 mL, 15.72 mmol) and DMSO (0.5 mL) and the mixture heated at 200° C. for ca. 45 min. After cooling to RT, the mixture was purified by normal phase chromatography, eluting with a gradient of 0-100% ethyl acetate in cyclohexane followed by a gradient of 0-10% MeOH in DCM and then further purified by MDAP (basic conditions), to give the title compound (49 mg). LCMS (A) m/z: 405 [M+1]$^+$, Rt 0.98 min (acidic).

Example 100

N-[3-Bromo-6-methyl-2-(1H-pyrazol-4-yl)thieno[2,3-b]pyridin-4-yl]-3-chlorobenzenesulfonamide

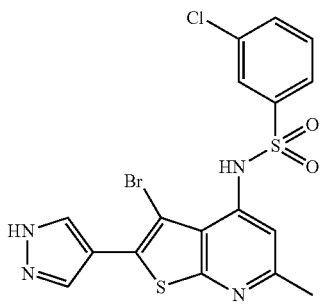 [SMILES: Cc1cc(NS(=O)(=O)c2cccc(Cl)c2)c2c(Br)c(-c3cn[nH]c3)sc2n1]

A mixture of ethyl 3-bromo-4-{[(3-chlorophenyl)sulfonyl]amino}-6-methyl-2-(1H-pyrazol-4-yl)thieno[2,3-b]pyridine-5-carboxylate (Description 74) (920 mg, 1.65 mmol) in DMSO (15 mL) and aqueous NaOH (5M) (3.31 mL, 16.55 mmol) was heated at 150° C. for ca. 1.5 h. After cooling to RT, the mixture was diluted with water (20 mL) and acidified with formic acid (ca. pH 4-5). The mixture was extracted with 10% MeOH/DCM (30 mL×5) and the combined organics dried and concentrated. The residue was passed through a C18 solid phase extractor cartridge, eluting with water (100 mL×4) and then with MeOH (100 mL×4) and the combined organics concentrated. The residue (877 mg) was taken-up in diphenyl ether (5.0 mL, 31.4 mmol) and DMSO (0.5 mL) and the mixture heated at 200° C. for ca. 1 h. After cooling to RT, the mixture was purified by chromatography on silica, eluting with a gradient of 0-100% ethyl acetate in cyclohexane, to give the title compound (430 mg). LCMS (A) m/z: 483/485 [M+1]$^+$, Rt 1.16 min (acidic).

Alternatively, a mixture of ethyl 3-bromo-4-{[(3-chlorophenyl)sulfonyl]amino}-6-methyl-2-(1H-pyrazol-4-yl)thieno[2,3-b]pyridine-5-carboxylate (Description 74) (8.2 g, 14.75 mmol) in DMSO (150 mL) and aqueous NaOH (5M) (11.80 mL, 59.0 mmol) was heated at 150° C. for ca. 15 min. Extra aqueous NaOH (5M) (11.80 mL, 59.0 mmol) was added and the mixture heated at 150° C. for another 45' min. After cooling to RT, the mixture was diluted with water (200 mL) and acidified with formic acid (ca. pH 4-5). The mixture was then extracted with 20% MeOH/DCM (75 mL×5) and the combined organics dried and concentrated. Water (100 mL) was added to the residue and a precipitate crashed-out which was collected by filtration and rinsed with water (50 mL×3). The solid was dried and subsequently taken-up in diphenyl ether (100 mL, 629 mmol) and DMSO (20 mL) and the mixture heated at 200° C. for ca. 35 min. After cooling to RT, the mixture was purified on silica, eluting with a gradient of 0-100% ethyl acetate in cyclohexane followed by 10% MeOH in DCM, to give the title compound (3.03 g).

Example 101

3-Chloro-N-[3-fluoro-6-methyl-2-(1H-pyrazol-4-yl)thieno[2,3-b]pyridin-4-yl]benzenesulfonamide

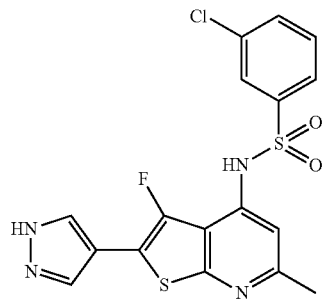 [SMILES: Cc1cc(NS(=O)(=O)c2cccc(Cl)c2)c2c(F)c(-c3cn[nH]c3)sc2n1]

A stirred solution of N-[3-bromo-6-methyl-2-(1H-pyrazol-4-yl)thieno[2,3-b]pyridin-4-yl]-3-chlorobenzenesulfonamide (Example 100) (120 mg, 0.248 mmol) in THF (1.5 mL) was cooled to −78° C. using a dry ice/acetone bath. n-BuLi (2.5M in Hexane) (0.109 mL, 0.273 mmol) was added dropwise and the mixture stirred at −78° C. for ca. 1.5 h. Then, N-fluorobenzenesulfonimide (82 mg, 0.260 mmol), pre-dissolved in THF (0.5 mL), was added dropwise and the mixture stirred at −78° C. for ca. 1 h and then left to stir at RT for 3 days (ca. 89 h). The reaction mixture was then quenched with saturated NH$_4$Cl solution (ca. 20 mL), extracted with ethyl acetate (20 mL×3) and the combined organics dried and concentrated. The residue was purified by normal phase chromatography, eluting with a gradient of 0-100% ethyl acetate in DCM and further purified by MDAP (acidic conditions), to give the title compound (5 mg). LCMS (A) m/z: 423 [M+1]$^+$, Rt 1.20 min (acidic).

Example 102

3-Chloro-N-[3-[3-(dimethylamino)phenyl]-6-methyl-2-(1H-pyrazol-4-yl)thieno[2,3-b]pyridin-4-yl]benzenesulfonamide

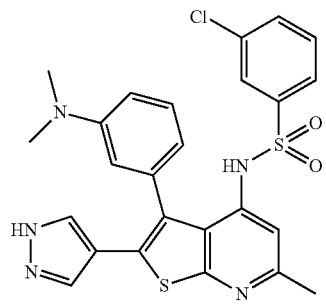 [SMILES: Cc1cc(NS(=O)(=O)c2cccc(Cl)c2)c2c(-c3cccc(N(C)C)c3)c(-c3cn[nH]c3)sc2n1]

A mixture of N-[3-bromo-6-methyl-2-(1H-pyrazol-4-yl)thieno[2,3-b]pyridin-4-yl]-3-chlorobenzenesulfonamide (Example 100) (100 mg, 0.207 mmol), 3-(N,N-dimethylamino)-phenylboronic acid (68.2 mg, 0.413 mmol) and tetrakis(triphenylphosphine)palladium(0) (11.9 mg, 10.34 µmol) and potassium carbonate (86 mg, 0.620 mmol) in 1,4-dioxane (1 mL), DMF (0.5 mL) and water (0.25 mL) was heated at 110° C. overnight (ca. 22 h). After cooling to RT, the reaction mixture was filtered through celite and the filtrate concentrated and purified by chromatography on silica, eluting with a gradient of 0-100% ethyl acetate in DCM. The material was then passed through an SCX cartridge, eluting with MeOH (ca. 60 mL) and 2M NH$_3$ in MeOH (60 mL), to give the title compound (8 mg). LCMS (A) m/z: 524 [M+1]$^+$, Rt 1.28 min (acidic).

Alternatively, 3 reactions were set up and the experimental procedures were as follows:

A mixture of 1,1-dimethylethyl 4-(3-bromo-4-{[(3-chlorophenyl)sulfonyl]amino}-6-methylthieno[2,3-t]pyridin-2-yl)-1H-pyrazole-1-carboxylate (Description 75) (100 mg, 0.171 mmol), 3-(N,N-dimethylamino)-phenylboronic acid (56.5 mg, 0.343 mmol), potassium carbonate (71.0 mg, 0.514 mmol) and tetrakis(triphenylphosphine)palladium(0) (4.95 mg, 4.28 µmol) were weighed into a microwave vial. 1,4-Dioxane (1.5 mL), DMF (0.75 mL) and water (0.38 mL) were added and the mixture heated in a microwave at 110° C. for 30 min. At this point, the three reaction mixture were combined and concentrated. The residue was passed through an SCX cartridge, eluted with MeOH (100 mL) and then with 2M NH$_3$ in MeOH (120 mL).

The basic methanolic solution was concentrated and the residue purified by MDAP (acidic conditions), to give the title compound (95.6 mg).

Example 103

3-Chloro-N-[6-methyl-3-[3-(4-morpholinyl)phenyl]-2-(1H-pyrazol-4-yl)thieno[2,3-b]pyridin-4-yl]benzenesulfonamide

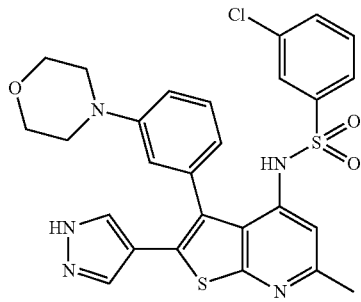 [SMILES: Cc1cc(NS(=O)(=O)c2cccc(Cl)c2)c2c(-c3cccc(N4CCOCC4)c3)c(-c3cn[nH]c3)sc2n1]

Two reactions were set up and the experimental procedures were as follows:

A mixture of 1,1-dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (100 mg, 0.171 mmol), 3-(morpholino)phenylboronic acid, pinacol ester (74.3 mg, 0.257 mmol), potassium carbonate (95 mg, 0.685 mmol) and tetrakis(triphenylphosphine)palladium(0) (3.96 mg, 3.43 µmol) were weighed into a microwave vial. 1,4-Dioxane (1.5 mL), DMF (0.75 mL) and water (0.38 mL) were added and the mixture heated in a microwave at 110° C. for 30 min. At this point, both reaction mixtures were combined and concentrated. Purification by chromatography on silica, eluting with a gradient of 0-100% ethyl acetate in DCM, followed by MDAP (acidic conditions), afforded the title compound (44 mg). LCMS (A) m/z: 566 [M+1]$^+$, Rt 1.24 min (acidic).

Alternatively, 5 reactions were set up and the experimental procedures were as follows:

A mixture of 1,1-dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (100 mg, 0.171 mmol), 3-(morpholino)phenylboronic acid, pinacol ester (99 mg, 0.343 mmol), tetrakis(triphenylphosphine)palladium(0) (19.79 mg, 0.017 mmol), bis(triphenylphosphine)palladium(II) chloride (12.02 mg, 0.017 mmol) and potassium carbonate (71.0 mg, 0.514 mmol) were weighed into a microwave vial. 1,4-Dioxane (1.5 mL), DMF (0.75 mL) and water (0.38 mL) were added and the mixture heated in a microwave at 120° C. for 15 min. At this point, the five reaction mixtures were combined and concentrated. The residue was passed through an SCX cartridge, eluting with MeOH (150 mL) and then 2M NH$_3$ in MeOH (200 mL). The basic methanolic solution was concentrated and the residue was purified by MDAP (acidic conditions), to give the title compound (115 mg).

Example 104

N-[3-[3,5-Bis(methyloxy)phenyl]-6-methyl-2-(1H-pyrazol-4-yl)thieno[2,3-b]pyridin-4-yl]-3-chlorobenzenesulfonamide

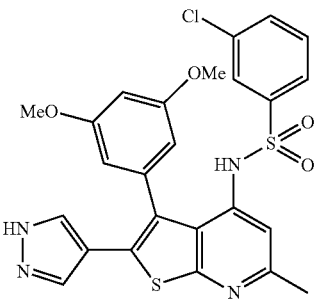 [SMILES: COc1cc(OC)cc(-c2c(-c3cn[nH]c3)sc3nc(C)cc(NS(=O)(=O)c4cccc(Cl)c4)c23)c1]

Two reactions were set up and the experimental procedures were as follows:

A mixture of 1,1-dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (100 mg, 0.171 mmol), 3,5-dimethoxyphenylboronic acid pinacol ester (90 mg, 0.343 mmol), potassium carbonate (95 mg, 0.685 mmol) and tetrakis(triphenylphosphine)palladium(0) (3.96 mg, 3.43 µmol) were weighed into a microwave vial. 1,4-Dioxane (1.5 mL), DMF (0.75 mL) and water (0.38 mL) were added and the mixture heated in a microwave at 110° C. for 30 min. At this point, both reaction mixtures were combined and concentrated. The residue was passed through an SCX cartridge, eluting with MeOH (75 mL) and then with 2M NH$_3$ in MeOH (100 mL). The basic methanolic solution was concentrated and purified by MDAP (acidic conditions), to give the title compound (45 mg). LCMS (A) m/z: 541 [M+1]$^+$, Rt 1.26 min (acidic).

Example 105

3-Chloro-N-{6-methyl-2-(1H-pyrazol-4-yl)-3-[3-(1-pyrrolidinyl)phenyl]thieno[2,3-b]pyridin-4-yl}benzenesulfonamide

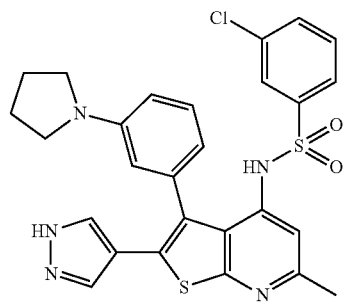 [SMILES: Cc1cc(NS(=O)(=O)c2cccc(Cl)c2)c2c(-c3cccc(N4CCCC4)c3)c(-c3cn[nH]c3)sc2n1]

1,1-Dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (350 mg, 0.599 mmol), 1-[3-(4,4,5,5-tetramethyl-1,3,2-dioxaborolan-2-yl)phenyl]pyrrolidine (327 mg, 1.2 mmol), tetrakis(triphenylphosphine)palladium(0) (34.6 mg, 0.03 mmol), bis(triphenylphosphine)palladium(II) chloride (21.04 mg, 0.030 mmol) and potassium carbonate (249 mg, 1.8 mmol) were charged into a microwave vial. DMF (2.5 mL) and water (1.0 mL) were added and the suspension degassed under nitrogen for ca. 5 min before being subjected to heating in a microwave at 100° C. for 30 min. The reaction mixture was then filtered through celite, rinsed with ethyl acetate (ca. 50 mL) and the solvent removed in vacuo. Purification by chromatography on silica, eluting with a gradient of 0-40% ethyl acetate in DCM followed by 0-20% MeOH in DCM and then further purification by MDAP (acidic conditions) afforded the title compound (20 mg). LCMS (A) m/z: 550 [M+1]$^+$, Rt 1.30 min (basic).

Alternatively, 4 reactions were set up and the experimental procedures were as follows:

A mixture of 1,1-dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (200 mg, 0.343 mmol), 1-[3-(4,4,5,5-tetramethyl-1,3,2-dioxaborolan-2-yl)phenyl]pyrrolidine (140 mg, 0.514 mmol), potassium carbonate (142 mg, 1.03 mmol), tetrakis(triphenylphosphine) palladium(0) (39.6 mg, 0.034 mmol) and bis(triphenylphosphine)palladium(II) chloride (24.04 mg, 0.034 mmol) were weighed into a microwave vial. 1,4-Dioxane (3.0 mL), DMF (1.5 mL) and water (0.75 mL) were added and the mixture heated in a microwave at 120° C. for 30 min. At this point, the four reaction mixtures were combined and concentrated. The residue was passed through an SCX cartridge, eluting with MeOH (250 mL) and then 2M NH$_3$ in MeOH (300 mL). The basic methanolic solution was concentrated and purified by normal phase chromatography eluting with 0-10% 2M NH$_3$ in MeOH in DCM. Further purification by normal phase chromatography eluting with 0-100% ethyl acetate in cyclohexane followed by MDAP (acidic conditions), afforded the title compound (190 mg).

Example 106

3-Chloro-N-[6-methyl-3-[3-(1-piperazinyl)phenyl]-2-(1H-pyrazol-4-yl)thieno[2,3-b]pyridin-4-yl]benzenesulfonamide hydrochloride

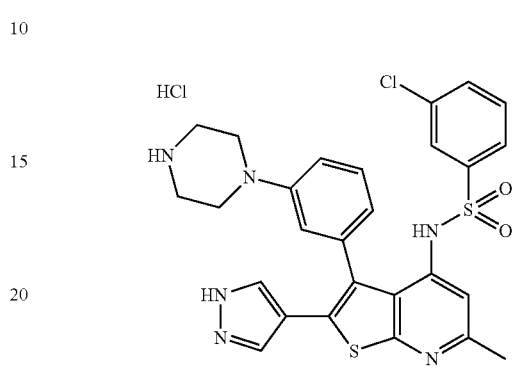

Three reactions were set up and the experimental procedures were as follows:

A mixture of 1,1-dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (100 mg, 0.171 mmol), 3-(4-tert-butoxycarbonylpiperazinyl)phenylboronic acid, pinacol ester (133 mg, 0.343 mmol), potassium carbonate (71.0 mg, 0.514 mmol), tetrakis(triphenylphosphine)palladium(0) (19.79 mg, 0.017 mmol) and bis(triphenylphosphine)palladium(II) chloride (12.02 mg, 0.017 mmol) were weighed into a microwave vial. 1,4-Dioxane (2 mL), DMF (1 mL) and water (0.5 mL) were added and the mixture heated in a microwave at 120° C. for 15 min. At this point, all three mixtures were combined and concentrated. The residue was then passed through an SCX cartridge, eluting with MeOH (150 mL) and then 2M NH$_3$ in MeOH (200 mL). The basic methanolic solution was concentrated and purified by normal phase chromatography, eluting with 0-100% ethyl acetate in DCM to give a residue (168 mg), which was subsequently taken-up in DCM (5 mL) and TFA (1 mL) added. The reaction mixture was stirred at RT for ca. 1 h and was then passed through an SCX cartridge, eluting with MeOH (100 mL) and then with 2M NH$_3$ in MeOH (150 mL). The basic methanolic solution was concentrated and purified by normal phase chromatography, eluting with 0-20% 2M NH$_3$ in MeOH in DCM to give a solid (ca. 125 mg). The solid was suspended in DCM (5 mL) and HCl (2M in diethyl ether) (0.128 mL, 0.257 mmol) was added. The mixture was stirred at RT for 30 min and solvent was then removed. The solid was triturated with DCM (5 mL×3) and then dried in vacuum oven, to give the title compound (102 mg) as hydrochloride salt. LCMS (A) m/z: 565 [M+1]$^+$, Rt 0.95 min (acidic).

Example 107

3-Chloro-N-[6-methyl-3-[5-(4-morpholinyl)-3-pyridinyl]-2-(1H-pyrazol-4-yl)thieno[2,3-b]pyridin-4-yl]benzenesulfonamide

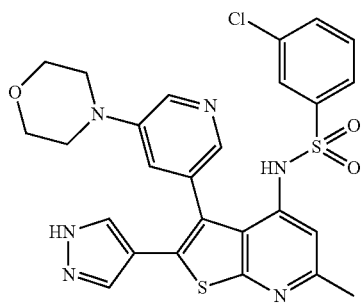 [SMILES: Cc1cc(NS(=O)(=O)c2cccc(Cl)c2)c2c(-c3cncc(N4CCOCC4)c3)c(-c3cn[nH]c3)sc2n1]

Two reactions were set up and the experimental procedures were as follows:

A mixture of 1,1-dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (100 mg, 0.171 mmol), 4-[5-(4,4,5,5-tetramethyl-1,3,2-dioxaborolan-2-yl)-3-pyridinyl]morpholine (Description 81) (214 mg, 0.737 mmol), potassium carbonate (71.0 mg, 0.514 mmol), tetrakis(triphenylphosphine)palladium(0) (19.79 mg, 0.017 mmol) and bis(triphenylphosphine)palladium(II) chloride (12.02 mg, 0.017 mmol) were weighed into a microwave vial. 1,4-Dioxane (2 mL), DMF (1 mL) and water (0.5 mL) were added and the mixture heated in a microwave at 120° C. for 15 min. At this point, both mixtures were combined and concentrated. The residue was passed through an SCX cartridge, eluting with MeOH (75 mL) and then with 2M NH$_3$ in MeOH (150 mL). The basic methanolic solution was concentrated and purified by normal phase chromatography, eluting with 0-10% MeOH in DCM, to give the title compound (65 mg). LCMS (A) m/z: 567 [M+1]$^+$, Rt 0.72 min (acidic).

Example 108

3-Chloro-N-{6-methyl-2-(1H-pyrazol-4-yl)-3-[5-(1-pyrrolidinyl)-3-pyridinyl]thieno[2,3-b]pyridin-4-yl}benzenesulfonamide

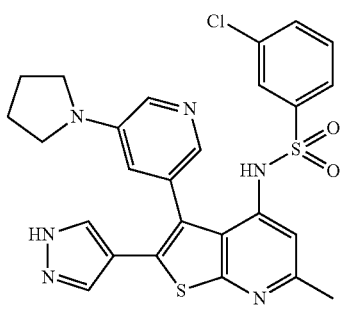 [SMILES: Cc1cc(NS(=O)(=O)c2cccc(Cl)c2)c2c(-c3cncc(N4CCCC4)c3)c(-c3cn[nH]c3)sc2n1]

Three reactions were set up and the experimental procedures were as follows:

A mixture of 1,1-dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (100 mg, 0.171 mmol), 3-(1-Pyrrolidinyl)-5-(4,4,5,5-tetramethyl-1,3,2-dioxaborolan-2-yl)pyridine (Description 79) (181 mg, 0.66 mmol), potassium carbonate (71.0 mg, 0.514 mmol), tetrakis(triphenylphosphine)palladium(0) (19.79 mg, 0.017 mmol) and bis(triphenylphosphine)palladium(II) chloride (12.02 mg, 0.017 mmol) were weighed into a microwave vial. 1,4-Dioxane (2 mL), DMF (1 mL) and water (0.5 mL) were added and the mixture heated in a microwave at 120° C. for 15 min. At this point, all three mixtures were combined and concentrated. The residue was passed through an SCX cartridge, eluting with MeOH (75 mL) and then 2M NH$_3$ in MeOH (150 mL). The basic methanolic solution was concentrated and purified by normal phase chromatography, eluting with 0-10% MeOH in DCM and then further purified by MDAP (acidic conditions), to give the title compound (61 mg). LCMS (A) m/z: 551 [M+1]$^+$, Rt 0.79 min (acidic).

Example 109

3-Chloro-N-[3-[5-(dimethylamino)-3-pyridinyl]-6-methyl-2-(1H-pyrazol-4-yl)thieno[2,3-b]pyridin-4-yl]benzenesulfonamide

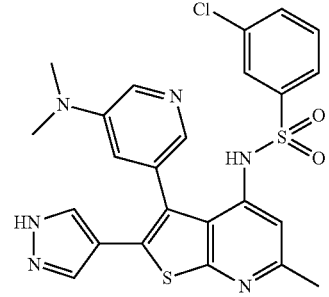 [SMILES: Cc1cc(NS(=O)(=O)c2cccc(Cl)c2)c2c(-c3cncc(N(C)C)c3)c(-c3cn[nH]c3)sc2n1]

Two reactions were set up and the experimental procedures were as follows:

A mixture of 1,1-dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (150 mg, 0.257 mmol), dimethylamino pyridine boronic acid (85 mg, 0.514 mmol), potassium carbonate (107 mg, 0.771 mmol), tetrakis(triphenylphosphine)palladium(0) (7.42 mg, 6.42 µmol) and bis(triphenylphosphine)palladium(II) chloride (4.51 mg, 6.42 µmol) were weighed into a microwave vial. 1,4-Dioxane (2.0 mL), DMF (1.0 mL) and water (0.5 mL) were added and the mixture heated in a microwave at 110° C. for 30 min. At this point, both reaction mixtures were combined and concentrated. The residue was passed through an SCX cartridge, eluting with MeOH (100 mL) and then with 2M NH$_3$ in MeOH (150 mL). The basic methanolic solution was concentrated and purified by MDAP (acidic conditions) and then further purified by normal phase chromatography, eluting with a gradient of 0-10% MeOH in DCM, to give the title compound (63 mg). LCMS (A) m/z: 523 [M−1]$^−$, Rt 0.78 min (acidic).

Example 110

3-Chloro-N-[6-methyl-3-[5-(methyloxy)-3-pyridinyl]-2-(1H-pyrazol-4-yl)thieno[2,3-b]pyridin-4-yl]benzenesulfonamide

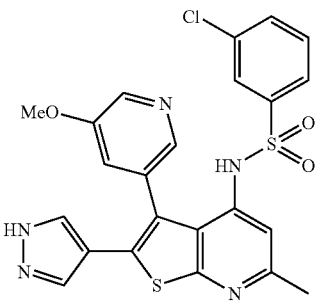

Two reactions were set up and the experimental procedures were as follows:

A mixture of 1,1-dimethylethyl 4-(3-bromo-4-{[(3-chlorophenyl)sulfonyl]amino}-6-methylthieno[2,3-b]pyridin-2-yl)-1H-pyrazole-1-carboxylate (Description 75) (100 mg, 0.171 mmol), 3-methoxy-5-pyridineboronic acid pinacol ester (81 mg, 0.343 mmol), potassium carbonate (71.0 mg, 0.514 mmol), tetrakis(triphenylphosphine)palladium(0) (4.95 mg, 4.28 µmol) and bis(triphenylphosphine)palladium (II) chloride (3.01 mg, 4.28 µmol) were weighed into a microwave vial. 1,4-Dioxane (1.5 mL), DMF (0.75 mL) and water (0.38 mL) were added and the mixture heated in a microwave at 110° C. for 30 min. At this point, both reaction mixtures were combined and concentrated. The residue was passed through an SCX cartridge, eluting with MeOH (100 mL) and then 2M NH$_3$ in MeOH (150 mL). The basic methanolic solution was concentrated and purified by MDAP (acidic conditions), to give the title compound (95 mg). LCMS (A) m/z: 512 [M+1]$^+$, Rt 0.88 min (acidic).

Example 111

3-Chloro-N-[6-methyl-3-(3-methylphenyl)-2-(1H-pyrazol-4-yl)thieno[2,3-b]pyridin-4-yl]benzenesulfonamide

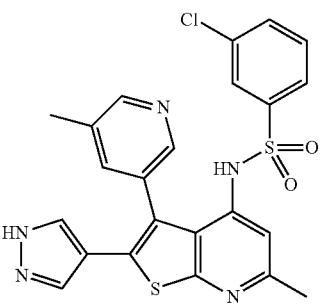 [SMILES: Cc1cncc(-c2c(-c3cn[nH]c3)sc3nc(C)cc(NS(=O)(=O)c4cccc(Cl)c4)c23)c1]

A suspension of N-[2-bromo-6-methyl-3-(3-methylphenyl)thieno[2,3-b]pyridin-4-yl]-3-chlorobenzenesulfonamide (Description 60) (214 mg, 0.421 mmol), 1-tert-butoxylcarbonyl-1H-pyrazole-4-boronic acid, pinacol ester (124 mg, 0.421 mmol), tetrakis(triphenylphosphine)palladium(0) (48.7 mg, 0.042 mmol) and aqueous sodium carbonate (2M) (0.421 mL, 0.843 mmol) was degassed under a nitrogen atmosphere for ca. 10 min before being subjected to microwave heating at 120° C. for 30 min. The reaction mixture was then partitioned between ethyl acetate and water (ca. 30 mL each). The aqueous layer was separated and re-extracted with ethyl acetate (ca. 25 mL) and the combined organic layer passed through a phase separator and the solvent removed in vacuo. Purification by chromatography on silica, eluting with a gradient of 0-80% ethyl acetate in cyclohexane, afforded the title compound (75 mg). LCMS (A) m/z: 495 [M+1]$^+$, Rt 1.31 min (acidic).

Example 112

3-Chloro-N-{6-methyl-3-[3-(1-pyrrolidinyl)phenyl]thieno[2,3-b]pyridin-4-yl}benzenesulfonamide

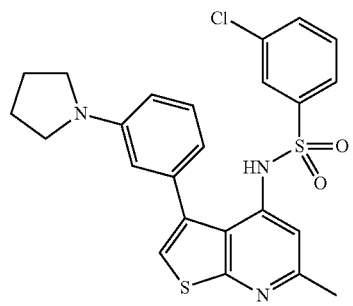 [SMILES: Cc1cc(NS(=O)(=O)c2cccc(Cl)c2)c2c(-c3cccc(N4CCCC4)c3)csc2n1]

To a mixture of N-[3-(3-bromophenyl)-6-methylthieno[2,3-b]pyridin-4-yl]-3-chloro-N-({[2-(trimethylsilyl)ethyl]oxy}methyl)benzenesulfonamide (Description 54) (960 mg, 1.538 mmol), BINAP (57.5 mg, 0.092 mmol), Pd$_2$(dba)$_3$ (28.2 mg, 0.031 mmol) and sodium tert-butoxide (443 mg, 4.61 mmol) in toluene (10 mL) was added pyrrolidine (0.254 mL, 3.08 mmol) and the mixture heated at 120° C. for ca. 2 h. After cooling to RT, the mixture was passed through celite, washed with DCM (ca. 20 mL×5) and the filtrate concentrated. The residue was purified by normal phase chromatography, eluting with 0-50% ethyl acetate in cyclohexane to give a residue which was subsequently taken-up in DCM (5 mL) and TFA (2.37 mL, 30.8 mmol) added. The mixture was stirred at RT overnight (ca. 16 h) and was then quenched with NaHCO$_3$ solution (ca. 50 mL) and extracted with DCM (30 mL×3). The combined organics were dried and concentrated and the residue purified by normal phase chromatography, eluting with a gradient of 0-100% ethyl acetate in cyclohexane and then further purified by MDAP (basic conditions). Final purification by normal phase chromatography, eluting with 0-100% ethyl acetate in DCM, afforded the title compound (197 mg). LCMS (A) m/z: 484 [M+1]$^+$, Rt 1.53 min (acidic).

Example 113

N-{6-Methyl-2-(1H-pyrazol-4-yl)-3-[5-(1-pyrrolidinyl)-3-pyridinyl]thieno[2,3-b]pyridin-4-yl}benzenesulfonamide

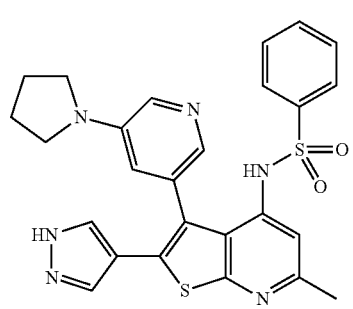 [SMILES: Cc1cc(NS(=O)(=O)c2ccccc2)c2c(-c3cncc(N4CCCC4)c3)c(-c3cn[nH]c3)sc2n1]

Three reactions were set up and the experimental procedures were as follows:

A mixture of 1,1-dimethylethyl 4-{3-bromo-6-methyl-4-[(phenylsulfonyl)amino]thieno[2,3-b]pyridin-2-yl}-1H-pyrazole-1-carboxylate (Description 71) (200 mg, 0.364 mmol), 3-(1-pyrrolidinyl)-5-(4,4,5,5-tetramethyl-1,3,2-dioxaborolan-2-yl)pyridine (Description 79) (399 mg, 0.73 mmol), potassium carbonate (151 mg, 1.09 mmol), tetrakis(triphenylphosphine)palladium(0) (42.1 mg, 0.036 mmol) and bis(triphenylphosphine)palladium(II) chloride (25.5 mg, 0.036 mmol) were weighed into a microwave vial. 1,4-Dioxane (3 mL), DMF (1.5 mL) and water (0.75 mL) were added and the mixture heated in a microwave at 120° C. for 30 min. At this point, all three reaction mixtures were combined and concentrated. The residue was passed through an SCX cartridge, eluting with MeOH (150 mL) and then with 2M $NH_3$ in MeOH (200 mL). The basic methanolic solution was concentrated and purified by normal phase chromatography, eluting with 0-100% ethyl acetate in DCM, followed by trituration with DCM (10 mL×3), to give the title compound (185 mg). LCMS (A) m/z: 517 [M+1]$^+$, Rt 0.76 min (acidic).

Example 114

N-{6-Methyl-2-(1H-pyrazol-4-yl)-3-[3-(1-pyrrolidinyl)phenyl]thieno[2,3-b]pyridin-4-yl}benzenesulfonamide

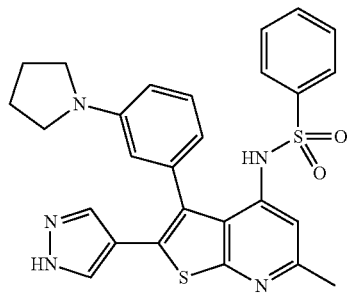 [SMILES: Cc1cc(NS(=O)(=O)c2ccccc2)c2c(-c3cccc(N4CCCC4)c3)c(-c3cn[nH]c3)sc2n1]

To a mixture of N-{3-(3-bromophenyl)-6-methyl-2-[1-({[2-(trimethylsilyl)ethyl]oxy}methyl)-1H-pyrazol-4-yl]thieno[2,3-b]pyridin-4-yl}-N-({[2-(trimethylsilyl)ethyl]oxy}methyl)benzenesulfonamide (Description 51) (485 mg, 0.617 mmol), BINAP (23.05 mg, 0.037 mmol), Pd$_2$(dba)$_3$ (11.30 mg, 0.012 mmol) and sodium tert-butoxide (178 mg, 1.851 mmol) in toluene (5 mL) was added pyrrolidine (0.102 mL, 1.234 mmol) and the mixture was heated at 120° C. for ca. 2 h. After cooling to RT, the mixture was passed through celite, washed with DCM (ca. 20 mL×5) and the filtrate concentrated. The residue was purified by normal phase chromatography, eluting with 0-50% ethyl acetate in cyclohexane to give a residue which was subsequently taken-up in DCM (5 mL) and TFA (0.475 mL, 6.17 mmol) added. The mixture was stirred at RT overnight (ca. 24 h). Extra TFA (0.475 mL, 6.17 mmol) was added and stirring continued at RT for ca. 4 h. Extra TFA (0.475 mL, 6.17 mmol) was added and stirring continued at RT overnight (ca. 20 h). The reaction mixture was then passed through SCX cartridge, eluting with MeOH (150 mL), then with 2M $NH_3$ in MeOH (200 mL). The basic methanolic solution was concentrated and the residue purified by normal phase chromatography, eluting with 0-100% ethyl acetate in cyclohexane and then further purified by MDAP (acidic conditions) and then by MDAP (basic conditions), to afford the title compound (113 mg). LCMS (A) m/z: 516 [M+1]$^+$, Rt 1.28 min (acidic).

Example 115

3-Chloro-N-{2-methyl-6-(methyloxy)-3-[3-(methyloxy)phenyl]thieno[2,3-b]pyridin-4-yl}benzenesulfonamide

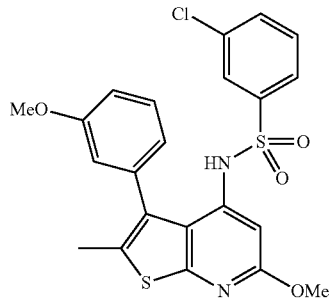 [SMILES: COc1cccc(-c2c(C)sc3nc(OC)cc(NS(=O)(=O)c4cccc(Cl)c4)c23)c1]

To a solution of 2-methyl-6-(methyloxy)-3-[3-(methyloxy)phenyl]thieno[2,3-b]pyridin-4-amine (Description 37) (16.5 mg, 0.055 mmol) in THF (0.5 mL) at −78° C. under a nitrogen atmosphere was added LiHMDS (1M solution in THF) (0.055 mL, 0.055 mmol). The solution was stirred at −78° C. for ca. 10 min before the addition of 3-chlorobenzenesulfonyl chloride (7.73 μL, 0.055 mmol). The reaction mixture was then warmed to RT under a nitrogen atmosphere overnight and was then partitioned between water and ethyl acetate (ca. 10 mL each). The aqueous layer was separated and re-extracted with ethyl acetate (ca. 10 mL). The combined organic layer was passed through phase separator and the solvent concentrated in vacuo. The residue was purified by MDAP (acidic conditions), to give the title compound (11 mg). LCMS (A) m/z: 475 [M+1]$^+$, Rt 1.63 min (acidic).

Example 116

3-Chloro-N-{2-methyl-3-[3-(methyloxy)phenyl]-6-oxo-6,7-dihydrothieno[2,3-b]pyridin-4-yl}benzenesulfonamide

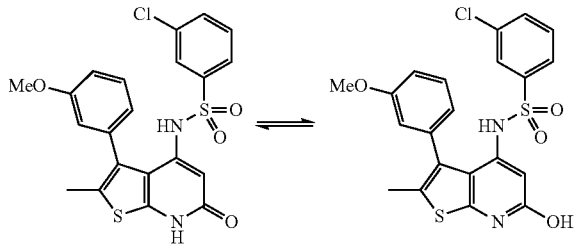 [SMILES: COc1cccc(-c2c(C)sc3[nH]c(=O)cc(NS(=O)(=O)c4cccc(Cl)c4)c23)c1 ; COc1cccc(-c2c(C)sc3nc(O)cc(NS(=O)(=O)c4cccc(Cl)c4)c23)c1]

A solution of 3-chloro-N-{2-methyl-6-(methyloxy)-3-[3-(methyloxy)phenyl]thieno[2,3-b]pyridin-4-yl}benzenesulfonamide (Example 115) (98 mg, 0.206 mmol) in 37% HCl (2 mL, 24.35 mmol) was heated to 100° C. under nitrogen atmosphere overnight. The reaction mixture was cooled to RT, diluted with MeOH and concentrated in vacuo. The residue was purified by MDAP (acidic conditions), to afford the title compound (58 mg). LCMS (A) m/z: 461 [M+1]$^+$, Rt 1.27 min (acidic).

Alternatively, a solution of 3-chloro-N-{2-methyl-6-(methyloxy)-3-[3-(methyloxy)phenyl]thieno[2,3-b]pyridin-4-yl}benzenesulfonamide (Example 115) (710 mg, 1.495 mmol) in 37% HCl (8 mL, 97 mmol) was heated to 100° C. under nitrogen atmosphere overnight. The reaction mixture was cooled to RT, diluted with DCM (ca. 50 mL) and washed with water (ca. 50 mL×2). The combined aqueous layer was re-extracted with DCM (ca. 25 mL) and the combined organic layers passed through phase separator and the solvent concentrated in vacuo. The residue was further triturated with DCM, to afford the title compound (407 mg).

Example 116 exhibits tautomerism and each tautomer shown above is included in the present invention.

Example 117

3-Chloro-N-{6-chloro-2-methyl-3-[3-(methyloxy) phenyl]thieno[2,3-b]pyridin-4-yl}benzenesulfonamide

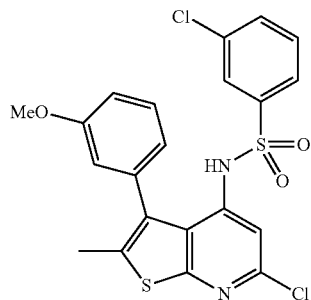 [SMILES: COc1cccc(-c2c(C)sc3nc(Cl)cc(NS(=O)(=O)c4cccc(Cl)c4)c23)c1]

A solution of 3-chloro-N-{2-methyl-3-[3-(methyloxy) phenyl]-6-oxo-6,7-dihydrothieno[2,3-b]pyridin-4-yl}benzenesulfonamide (Example 116) (150 mg, 0.325 mmol) in phenylphosphonic dichloride (1.5 mL, 10.72 mmol) was heated to 200° C. under a nitrogen atmosphere. The reaction mixture was cooled to RT, poured dropwise onto ice and left for ca. 30 min. The aqueous layer was extracted with DCM (ca. 25 mL×2), the combined organics passed through phase separator and the solvent removed in vacuo. The residue was then purified by normal phase chromatography, eluting with a gradient of 0-50% ethyl acetate in cyclohexane and then further purified by MDAP (acidic conditions), to afford the title compound (37 mg). LCMS (A) m/z: 479 [M+1]$^+$, Rt 1.62 min (acidic).

Example 118

3-Chloro-N-{6-cyano-2-methyl-3-[3-(methyloxy) phenyl]thieno[2,3-b]pyridin-4-yl}benzenesulfonamide

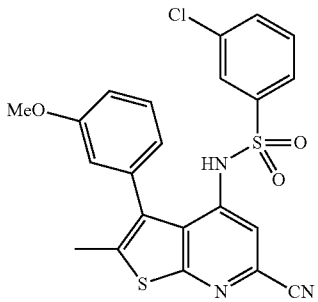 [SMILES: COc1cccc(-c2c(C)sc3nc(C#N)cc(NS(=O)(=O)c4cccc(Cl)c4)c23)c1]

To a stirred solution of 3-chloro-N-{6-chloro-2-methyl-3-[3-(methyloxy)phenyl]thieno[2,3-b]pyridin-4-yl}benzenesulfonamide (Example 117) (70 mg, 0.146 mmol) in 1-methylimidazole (1 mL) at RT was added potassium ferrocyanide (12.34 mg, 0.029 mmol) and copper(I) iodide (2.78 mg, 0.015 mmol). The reaction mixture was heated to 160° C. under a nitrogen atmosphere. Extra potassium ferrocyanide (12.34 mg, 0.029 mmol) and copper(I) iodide (2.78 mg, 0.015 mmol) were added and the mixture heated to 180° C. overnight. The reaction mixture was then cooled to RT and purified by normal phase chromatography, eluting with a gradient of 0-40% ethyl acetate in DCM and then further purified by MDAP (acidic conditions), to give the title compound (5 mg). LCMS (A) m/z: 470 [M+1]$^+$, Rt 1.53 min (acidic).

Example 119

4-Bromo-N-{2,6-dimethyl-3-[3-(methyloxy)phenyl] thieno[2,3-b]pyridin-4-yl}benzenesulfonamide

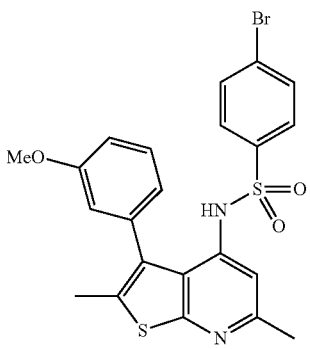 [SMILES: COc1cccc(-c2c(C)sc3nc(C)cc(NS(=O)(=O)c4ccc(Br)cc4)c23)c1]

To a solution of 2,6-dimethyl-3-[3-(methyloxy)phenyl] thieno[2,3-b]pyridin-4-amine (Description 4) (100 mg, 0.352 mmol) in THF (2 mL) cooled in an ice bath was added LiHMDS (1M solution in THF) (0.774 mL, 0.774 mmol). The resulting reaction mixture was stirred for 45 min before addition of 4-bromobenzenesulfonyl chloride (225 mg, 0.879 mmol). The reaction mixture was then stirred at RT for a further 12 h. The reaction mixture was diluted with water (15 mL) and the aqueous layer re-extracted with DCM (30 mL×3). The organics were combined, dried over a phase separating column and concentrated. To the residue was added MeOH (ca. 0.5 mL) and a solid crashed-out which was collected by filtration and rinsed with MeOH (ca. 2 mL). The solid was then dried, to afford the title compound (104 mg). LCMS (A) m/z: 503/505 [M+1]$^+$, Rt 1.11 min (basic).

Example 120

3-Chloro-N-{3-[4-(1,1-dimethylethyl)phenyl]-2,6-dimethylthieno[2,3-b]pyridin-4-yl}benzenesulfonamide

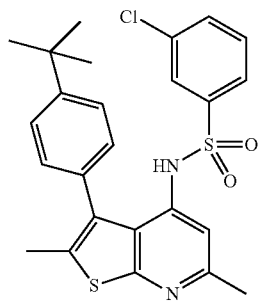 [SMILES: Cc1cc(NS(=O)(=O)c2cccc(Cl)c2)c2c(-c3ccc(C(C)(C)C)cc3)c(C)sc2n1]

Under nitrogen, N-(3-bromo-2,6-dimethylthieno[2,3-b] pyridin-4-yl)-3-chlorobenzenesulfonamide (Example 61) (100 mg, 0.232 mmol) was dissolved in toluene (2 mL) and [4-(1,1-dimethylethyl)phenyl]boronic acid (61.9 mg, 0.347 mmol), PdCl$_2$(dppf).DCM (18.91 mg, 0.023 mmol) and Cs$_2$CO$_3$ (226 mg, 0.695 mmol) were added. The mixture was then heated in a microwave at 150° C. for 30 min. Water (10 mL) was added and the mixture extracted with ethyl acetate (3×10 mL). The organic layer was dried over MgSO$_4$, filtered and concentrated. The residue was purified by normal phase chromatography, eluting with a gradient of 0-20% ethyl acetate in cyclohexane, to give the title compound (51 mg). LCMS (A) m/z: 485 [M+1]$^+$, Rt 1.70 min (basic).

Example 121

N-{4-{[(3-Chlorophenyl)sulfonyl]amino}-6-methyl-3-[3-(methyloxy)phenyl]thieno[2,3-b]pyridin-2-yl}acetamide

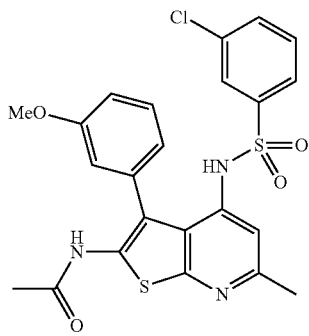 [SMILES: COc1cccc(-c2c(NC(C)=O)sc3nc(C)cc(NS(=O)(=O)c4cccc(Cl)c4)c23)c1]

To a stirred solution of N-{2-amino-6-methyl-3-[3-(methyloxy)phenyl]thieno[2,3-b]pyridin-4-yl}-3-chlorobenzenesulfonamide (Description 85) (40 mg, 0.087 mmol) in DCM (3 mL) was added triethylamine (0.036 mL, 0.261 mmol) and acetyl chloride (7.42 ul, 0.104 mmol) and the mixture stirred at RT for ca. 1 h. NaHCO$_3$ solution (25 mL) was then added and the mixture extracted with DCM (20 mL×3) and the combined organics dried and concentrated. The residue was purified by normal phase chromatography, eluting with a gradient of 0-50% ethyl acetate in DCM and was then further purified by MDAP (acidic conditions), to give the title compound (5.8 mg). LCMS (A) m/z: 502 [M+1]$^+$, Rt 1.05 min (acidic).

Example 122

N-{2,6-Dimethyl-3-[3-(methyloxy)phenyl]thieno[2,3-b]pyridin-4-yl}-1-phenylmethanesulfonamide

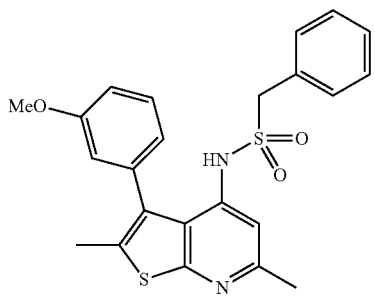 [SMILES: COc1cccc(-c2c(C)sc3nc(C)cc(NS(=O)(=O)Cc4ccccc4)c23)c1]

To a stirred solution of 2,6-dimethyl-3-[3-(methyloxy)phenyl]thieno[2,3-b]pyridin-4-amine (100 mg, 0.352 mmol) (Description 4) in THF (2 mL) cooled in an ice bath was added LiHMDS (1M solution in THF) (0.774 mL, 0.774 mmol). The reaction mixture was stirred at RT for 45 min before the addition of phenylmethanesulfonyl chloride (168 mg, 0.879 mmol). The reaction mixture was stirred at RT for a further 16 h and was then cooled in an ice bath before the addition of LiHMDS (1M solution in THF) (0.352 mL, 0.352 mmol). The reaction mixture was then stirred at RT for 1 h before the addition of phenylmethanesulfonyl chloride (67.2 mg, 0.352 mmol). The reaction mixture was stirred at RT for a further 16 h and then diluted with water (10 mL) and the aqueous layer extracted with DCM (3×20 mL). The combined organic extracts were dried over a phase separating column and concentrated. The residue was purified by MDAP (basic conditions), to afford the title compound (10 mg). LCMS (A) m/z: 439 [M+1]$^+$, Rt 1.31 min (basic).

Example 123

1-(4-Chlorophenyl)-N-{2,6-dimethyl-3-[3-(methyloxy)phenyl]thieno[2,3-b]pyridin-4-yl}methane sulfonamide

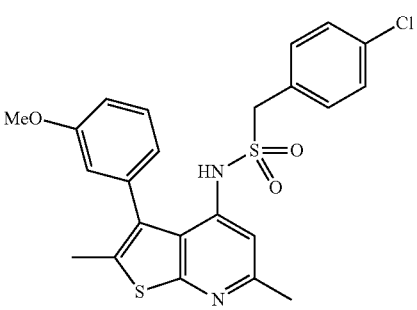 [SMILES: COc1cccc(-c2c(C)sc3nc(C)cc(NS(=O)(=O)Cc4ccc(Cl)cc4)c23)c1]

To a stirred solution of 2,6-dimethyl-3-[3-(methyloxy) phenyl]thieno[2,3-b]pyridin-4-amine (100 mg, 0.352 mmol) (Description 4) in THF (2 mL) cooled in an ice bath was added LiHMDS (1M solution in THF) (0.774 mL, 0.774 mmol). The reaction mixture was stirred at RT for 45 min before the addition of 4-chlorobenzylsulfonyl chloride (198 mg, 0.879 mmol). The reaction mixture was then stirred at RT for a further 16 h and was then cooled in an ice bath before the addition of LiHMDS (1M solution in THF) (0.352 mL, 0.352 mmol). The reaction mixture was stirred at RT for 1 h before the addition of 4-chlorobenzylsulfonyl chloride (79.2 mg, 0.352 mmol). The reaction mixture was stirred at RT for a further 16 h and then diluted with water (10 mL) and the aqueous layer extracted with DCM (3×20 mL). The combined organic extracts were dried over a phase separating column and concentrated. The residue was purified by MDAP (basic conditions), to afford the title compound (22 mg). LCMS (A) m/z: 473 [M+1]$^+$, Rt 1.42 min (basic).

Example 124

1-(2-Chlorophenyl)-N-{2,6-dimethyl-3-[3-(methyloxy)phenyl]thieno[2,3-b]pyridin-4-yl}methanesulfonamide

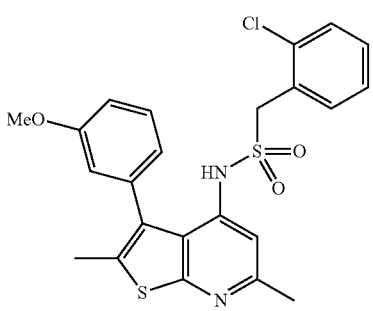 [SMILES: COc1cccc(-c2c(C)sc3nc(C)cc(NS(=O)(=O)Cc4ccccc4Cl)c23)c1]

To a stirred solution of 2,6-dimethyl-3-[3-(methyloxy) phenyl]thieno[2,3-b]pyridin-4-amine (100 mg, 0.352 mmol) (Description 4) in THF (2 mL) cooled in an ice bath was added LiHMDS (1M solution in THF) (0.774 mL, 0.774 mmol). The reaction mixture was stirred at RT for 45 min before the addition of 2-chlorobenzylsulfonyl chloride (198 mg, 0.879 mmol). The reaction mixture was stirred at RT for a further 16 h and was then cooled in an ice bath before the addition of LiHMDS (1M solution in THF) (0.352 mL, 0.352 mmol). The reaction mixture was stirred at RT for 1 h before the addition of 2-chlorobenzylsulfonyl chloride (79.2 mg, 0.352 mmol). The reaction mixture was then stirred at RT for a further 16 h and then diluted with water (10 mL) and the aqueous layer extracted with DCM (3×20 mL). The combined organic extracts were dried over a phase separating column and concentrated. The residue was purified by MDAP (basic conditions), to afford the title compound (6 mg). LCMS (A) m/z: 473 [M+1]$^+$, Rt 1.07 min (basic).

Example 125

4-Chloro-N-{2,6-dimethyl-3-[3-(methyloxy)phenyl]thieno[2,3-b]pyridin-4-yl}-4-piperidinesulfonamide

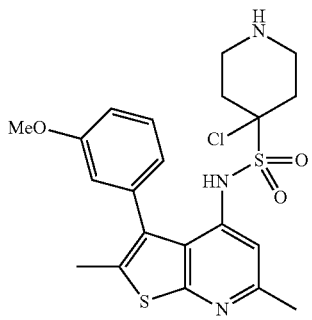 [SMILES: COc1cccc(-c2c(C)sc3nc(C)cc(NS(=O)(=O)C4(Cl)CCNCC4)c23)c1]

Phenylmethyl 4-chloro-4-[({2,6-dimethyl-3-[3-(methyloxy)phenyl]thieno[2,3-b]pyridin-4-yl}amino)sulfonyl]-1-piperidinecarboxylate (Example 10) (80 mg, 0.133 mmol) was taken-up in EtOH (5 mL), MeOH (5 mL) and acetic acid (1 mL). 10% Palladium on carbon (14.19 mg, 0.013 mmol) was then added and the reaction mixture was stirred at RT under 2 Bar of hydrogen for 48 h. The reaction mixture was then filtered through celite and the celite was washed with 50 mL of MeOH. The solvent was concentrated to give a residue which was purified by normal phase chromatography, eluting with a gradient from 0-10% 2N NH$_3$ in MeOH in DCM and then further purified by MDAP (basic conditions), to afford the title compound (7 mg). LCMS (A) m/z: 466 [M+1]$^+$, Rt 0.81 min (basic).

Example 126

3-Chloro-N-[2,6-dimethyl-3-(1H-pyrrol-3-yl)thieno[2,3-b]pyridin-4-yl]benzenesulfonamide

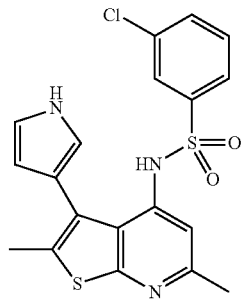 [SMILES: Cc1cc(NS(=O)(=O)c2cccc(Cl)c2)c2c(-c3cc[nH]c3)c(C)sc2n1]

Under nitrogen, N-(3-bromo-2,6-dimethylthieno[2,3-b]pyridin-4-yl)-3-chlorobenzenesulfonamide (Example 61) (100 mg, 0.232 mmol) was dissolved in 1,4-dioxane (2.5 mL) and water (1 mL). 1,1-Dimethylethyl 3-(4,4,5,5-tetramethyl-1,3,2-dioxaborolan-2-yl)-1H-pyrrole-1-carboxylate (102 mg, 0.347 mmol), bis(triphenylphosphine)palladium(II) chloride (16.26 mg, 0.023 mmol) and potassium carbonate (96 mg, 0.695 mmol) were added and the mixture heated in a microwave at 100° C. for 10 min. The solution was then concentrated, ethyl acetate (10 mL) added and the mixture washed with water (2×5 mL). The organic layer was dried over MgSO$_4$, filtered and the solvent removed in vacuo. The residue was purified by normal phase chromatography, eluting with a gradient of 0-30% ethyl acetate in cyclohexane and then further purified by MDAP (acidic conditions), to give the title compound (19.8 mg). LCMS (A) m/z: 416 [M−1]$^-$, Rt 1.47 min (acidic).

Biological Data

As stated above, the compounds according to Formula I are NOX2 inhibitors, and are useful in the treatment of a variety of diseases include neurodegenerative diseases such as amyotrophic lateral sclerosis, Parkinson's disease, Alzheimer's disease and Huntington's disease; neuroinflammatory diseases such as multiple sclerosis; cardiovascular diseases such as hypertension, atherosclerosis, cardiac hypertrophy, cardiac fibrosis and stroke; ocular diseases such as diabetic macular edema, diabetic retinopathy, age-related macular degeneration and glaucoma; spinal cord injury; and traumatic brain injury. The biological activities of the compounds according to Formula I can be determined using any suitable assay for determining the activity of a candidate compound as a NOX2 inhibitor, as well as tissue and in vivo models.

In resting cells, NOX2 contains the membrane bound catalytic subunit gp91 and a p22 subunit, the cytosolic components p47, p67 and rac2 as well as an FAD and NADPH binding site. Upon stimulation, the p47 subunit becomes phosphorylated and the cytosolic components assemble with the membrane components to produce an active NOX2 complex. The following assays were designed to measure the in vitro production of superoxide (O$_2$—) by NOX2 through reduction of oxygen using NADPH/NADH as an electron donor.

In one embodiment, the invention relates to a fluorescence assay for determining the activity of a candidate compounds as a NOX2 inhibitor. In the fluorescence assay, superoxide production by NOX2 is measured by coupling the disproportionation of superoxide, which forms H$_2$O$_2$, to horse radish peroxidase (HRP) and amplex red.

Fluoresence Assay

In the high throughput fluorescence assay, superoxide production by NOX2 is measured by coupling the disproportionation of superoxide, which forms H$_2$O$_2$, to horse radish peroxidase (HRP) and amplex red. The final product is a fluorescent resorufin signal at an excitation and emission of 560 nm and 590 nm, respectively.

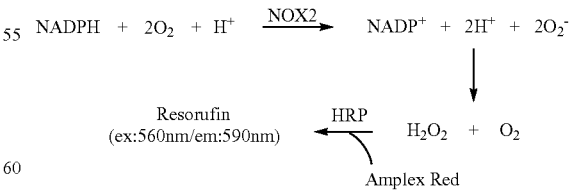

Materials

Baby Hamster Kidney (BHK) cells were transfected with the NOX 2 enzyme complex membrane bound subunits gp91$^{phox}$ and p22$^{phox}$ and membranes prepared using a Waring Blender and stocks prepared in a storage buffer of 50 mM Hepes, 1 mM EDTA, 25 ug/ml Bacitracin and 0.1 mM Leupeptin. Native Human-H6-P47, Human-H6-P67 and Human-H6-RAC2 were each baculovirus expressed and purified from 10 L of Sf9 cells freshly harvested by NiNTA agarose and Superdex 200 and prepared in a storage buffer of 25 mM Hepes pH7.4, 150 mM NaCl, 0.5 mM DTT, 1 mM MgCl2 with estimated Purity of 90% by gel densitometry.

Flavin Adenine Dinucleotide (FAD), Catalase-Agarose, Dibasic and Monobasic Potassium Phosphate, EGTA, MgCl2, NADPH, Horseradish Peroxidase (HRP), Glycerol, Arachidonic Acid (from Porcine Liver) were purchased from Sigma (St. Louis, Mo.; catalog #s F6625, C9284-50KU, P8584, P5379, E4378, M-1028, N-0411, P-8250, G-5516 and A3555, respectively). GTP-γ-S (Guanosine-5'-O-(3-thiotriphosphate), tetralithium salt, powder) was purchased from Roche Diagnostics (catalog #10220647001). Amplex Red was purchased from Molecular Probes, Inc. (Invitrogen catalog #A12222). Diphenyleneiodonium chloride (DPI) was purchased from Biomol International (Plymouth Meeting, Pa.; catalog #CN-240). Dimethyl sulfoxide (DMSO) from EMD Chemicals (VWR catalog #MX1456-1). 384 well and 1536 well micro-titer plates were purchased from Greiner Bio-One Inc (Monroe, N.C.; catalog #s784076 and 782076, respectively). 50, 250 and 500 ml Conical Centrifuge Tubes were supplied by Corning Life Sciences (Lowell, Mass.). Eppendorf Centrifuge 5804 was supplied by Eppendorf SA, (Hamburg Germany). Multidrop Combi liquid dispenser was supplied by Thermo Electron Corporation (Waltham, Mass.). Cybi-Well liquid dispenser was supplied by Cybio Inc. (Jena, Germany). Hummingbird nanoliter liquid dispenser was supplied by Genomic Solutions (Ann Arbor, Mich.). Viewlux Imager Plate Reader and Envision Plate Reader were supplied by Perkin Elmer (Waltham, Mass.). Infinite F500 Reader and Freedom Evo liquid handler supplied by Tecan Group Ltd (Switzerland). Spectromax spectrophotometer supplied by Molecular Devices (Silicon Valley, Calif.)

Assay 1:
1×NOX2 Fluorescence Assay Buffer:
All stock solutions were placed on ice, except for the FAD solution, which was placed at RT. The final concentrations in the 1×NOX2 fluorescence assay buffer were 50 mM KPO4 pH 7, 10 uM FAD, 1 mM EGTA, 4 mM MgCl2, 1 uM GTPgS.

2× Substrate Solution:
Catalase-Agarose beads were kept on ice, Amplex Red solution was kept on a 37° C. heat block, 1× assay buffer was kept at room temperature. The 2× substrate solution was made by mixing 1×NOX2 fluorescence assay buffer with catalase beads and NADPH. The 2× substrate solution with catalase beads were incubated for 30 minutes at RT and filtered using a 0.2 micron Nalgene filter. Homogenized Amplex Red was then added in the dark. Final 2× substrate solution concentrations in 1× assay buffer were 50 U/mL catalase beads, 100 uM NADPH, 40 uM Amplex Red.

2× Enzyme/NOX2 Complex Solution:
1×NOX2 fluorescence assay buffer at RT was mixed with HRP, Human-H6-RAC2, Human-H6-P47, Human-H6-P67 and gp91/p22 BHK membranes. Arachidonic acid was then added. Final 2× enzyme/NOX2 Complex solution concentrations in 1× assay buffer were 4 U/mL HRP, 40 nM RAC2, 200 nM P47, 300 nM P67, 0.0092 ug/uL gp91/p22 BHK membranes and 40 uM Arachidonic acid.

Reaction Mixture and Assay:
50 nL or 100 nL volumes of 100× stock compounds in DMSO for single-shot and dose response testing were dispensed from source plates into black 1536 well or 384 well assay plates, respectively, with a Hummingbird nanoliter liquid dispenser. Full inhibition controls were dispensed using 100 nL/well of 5 mM DPI to column 18 of a 384 well plate or 50 nL/well 5 mM DPI to columns 35 and 36 of a 1536 well plate. Full activity controls were dispensed using 100 mL/well of 100% DMSO to column 6 of a 384 well plate or 50 nL/well 100% DMSO to columns 11 and 12 of a 1536 well plate. 2.5 uL or 5 uL volumes of 2× enzyme solution were dispensed using Cybi-well or Multidrop Combi into black 1536 well or 384 well assay plates, respectively, and allowed to pre-incubate with compound/DMSO for 15 minutes at room temperature. The substrate addition was performed in a dark environment as follows: 2.5 uL or 5 uL volumes of 2× substrate solution were dispensed using Cybi-well or Multidrop Combi into black 1536 well or 384 well assay plates, respectively, and centrifuged for approximately 10 seconds at 1000 rpm. Fluorescence readings were taken following 5 minutes at room temperature with a Viewlux imager plate reader using excitation at 525/20 nm and emission at 598/25 nm.

Assay 2
1×NOX2 Fluorescence Assay Buffer:
Same as described in Assay 1 above.

2.5× Enzyme Solution:
Final concentrations in the 2.5× enzyme solution: 5 U/mL HRP, 50 nM RAC2, 250 nM p47, 375 nM p67, 0.0115 ug/uL gp91/p22 BHK membranes, 50 uM Arachidonic Acid 2.5× Substrate Solution Preparation:
Final concentrations in the 2.5× substrate solution: 125 U/mL catalase beads, 125 uM NADPH, 50 uM Amplex Red.

Compound Dilution and Assay:
Serial dilution (1:3.16 fold serial dilution) of the compound was performed in 100% DMSO in 96 well plate—Rows B-H, Col 1-10. Row A=DPI. Starting concentration was 10E-2M (10 mM). Final maximum compound concentration in the assay was 10E-4M (100 uM). DPI in column 11 and 100% DMSO in column 12 provide the positive and negative controls respectively with regards to NOX inhibition. Compounds were diluted 20 fold in 1× buffer using Tecan Freedom Evo. 10 ul of compounds were transferred to 190 ul/well 1× assay buffer. 4 ul compounds from 96 well compound plates were added to 384 well assay plate using Tecan Freedom Evo.

8 ul/well of 2.5× enzyme solution was added to the 384 well assay plate using Combi Multidrop dispensed using the micro-cassette. The plate was centrifuged for approximately 10 seconds up to 1000 rpm. Enzyme was pre-incubated with compound for 15 minutes at room temperature in the dark after which time 8 ul/well of 2.5× substrate solution was added to the 384 well assay plate using Combi Multidrop using the micro-cassette. The plate was centrifuged for approximately 10 seconds up to 1000 rpm. Fluorescence at ex535 nm/25 nm and em590 nm/20 nm was read using the Tecan Infinite F500 plate reader.

Absorbance Assay
In the orthogonal absorbance assay, superoxide production by NOX2 is measured via the reduction of Cytochrome C at an absorbance wavelength of 550 nm (Abo et al. (1992) *J. Biol. Chem.* 267:16767-16770).

Materials
Corning Low Volume 384 Well Black with Clear Flat Bottom Polystyrene Not Treated Microplate, Non-Sterile, Corning Life Sciences Inc. (Big Flats, N.Y.). Cytochrome C (from horse heart), and CHAPS were purchased from Sigma (St. Louis, Mo.; catalog #s C7752 and C3023, respectively).

1×NOX2 Absorbance Assay Buffer:
Same as described in Assay 1 above.

2× Substrate Solution:

6 mL of HPLC grade water was added to 5 mg of NADPH to dilute to a 1 mM stock. 1×NOX2 absorbance assay buffer was mixed with 1.0 mL 1 mM NADPH at RT. Final 2× substrate solution concentrations in 1× assay buffer was 100 uM NADPH.

2× Enzyme/NOX2 Complex Solution:

The following were added to a Corning tube: 1×NOX2 absorbance assay buffer at RT, Human-H6-RAC2, Human-H6-P47, Human-H6-P67, gp91/p22 BHK membranes. Arachidonic acid was then added. Final 2× enzyme/NOX2 Complex solution concentrations in 1× assay buffer were: 80 nM RAC2, 400 nM P47, 600 nM P67, 0.0184 ug/ul gp91/p22 BHK membranes and 40 uM Arachidonic Acid.

Reaction Mixture and Assay:

100 nl volumes of 200× stock compounds in DMSO for single-shot and dose response testing were dispensed from source plates into black clear bottom Corning 384 well assay plates with a Hummingbird nanoliter liquid dispenser. Full inhibition controls were dispensed using 100 nL/well of 5 mM DPI to column 18 of a 384 well plate. Full activity controls were dispensed using 100 nL/well of 100% DMSO to column 6 of a 384 well plate. 10 uL volumes of 2× enzyme solution were dispensed using Cybi-well into black clear bottom Corning 384 well assay plates, and allowed to pre-incubate with compound/DMSO for 15 minutes at room temperature. 10 uL volumes of 2× substrate solution were dispensed using Cybi-well into black clear bottom Corning 384 well assay plates and centrifuged for approximately 10 seconds at 1000 rpm. Absorbance readings were measured kinetically on the SpectrMax plate reader for 20 minutes (1 read/minute) at 550 nm. The slope from data points from reads time=4 minutes to 19 minutes were obtained and used for calculations.

Results

All exemplified compounds (Examples 1-126) were tested in the fluorescence assay and the absorbance assay described above. All exemplified compounds exhibited a pIC50>4 in at least one of the assays.

Cell-Based Assays

In the cell-based assay, superoxide production by NOX2 was measured in differentiated HL60 cells, a human myelomonocytic leukemia cell line, using either Oxyburst (Assay1) or L012 (Assay2). Differentiation of HL-60 cells to granulocytes increases NOX2 expression. The phorbol 12-myristate 13-acetate (PMA) was used to stimulate the production of superoxide in HL60 cells by activating protein kinase C, which then activated the NADPH oxidase (NOX) enzymes. Inhibition of NOX2 enzyme was detected by the reversal of fluorescence signal (Assay1) or luminescence signal (Assay2). The control inhibitor used was diphenyleneiodonium chloride (DPI), a flavonoid inhibitor capable of non-selectively inhibiting superoxide produced by NOX enzymes.

Assay 1: in this high-throughput screening assay, oxyburst green bovine serum albumin (BSA) was used to detect superoxide production in HL60 cells. Oxidation of Oxyburst green BSA by hydrogen peroxide as a result of the activation of NOX2 by PMA. Oxyburst green BSA fluorescence was measured at excitation 485 nm and emission 530 nm.

Assay 2: in this assay, a chemiluminescence probe, L-012 was used to detect superoxide production in HL60 cells. L-012 reacted with various types of reactive oxygen species generated by PMA-activated HL60 cells. Luminescence was measured using Tecan Infinite 500.

Materials

The HL60 cells were differentiated into neutrophil-like cells by adding 1.3% DMSO in the media for 3-7 days (Hua, J et al. (2000) *Journal of Leukocyte Biology.* 68:216-224). Iscove's Modified Dulbecco's Media (IMDM) with L-Glutamine and 25 mM HEPES buffer, Fetal Bovine Serum (FBS), Penicillin/Streptomycin, Oxyburst Green BSA, PBS, and HBSS buffer with Calcium Chloride and Magnesium Chloride were purchased from Invitrogen (Catalog #s: 12440-061, 10500-064, 15140-163, O-13291, 14190-250, and 14025-134 respectively). Phorbol 12-myristate 13-acetate (PMA), glucose, and CHAPS were purchased from Sigma (Catalog #s: 79346, D-9434, and C5070 respectively). Diphenyleneiodonium chloride (DPI) was purchased from Toronto Research Chemicals (Catalog #: D491500). L-012 was purchased from Wako Chemical (Catalog #: 120-04891). Dimethyl sulfoxide (DMSO) was purchased EMD Chemicals (VWR Catalog #: MX1456-1). Multidrop combi was purchased from Thermo Electron Corporation (Waltham, Mass., USA). Hummingbird nanoliter liquid dispenser was purchased from Genomics Solution (Ann Arbor, Mich., USA). 384 well low-volume plates and polypropylene 384 well clear plates were purchased from Greiner (Catalog #: 784076 and 781280 respectively). 96 well plate and 384 well plate black assay plates were purchased from Greiner (Catalog #: 655094 and 781098). 96 well plate for compound serial dilution was purchased from Corning (Catalog #: 9017). Acquest or Analyst fluorescence plate reader was purchased from LJL Biosystems/Molecular Devices (California, USA). Tecan Infinite 500 was purchased from Tecan (Switzerland).

Cells Media

Media for HL60 cells were kept at 4° C. for storage and were warmed to 37° C. in a water bath before use. The media components were IMDM media with 20% FBS and 1% Penicillin/Streptomycin.

Compound Buffer

Buffer to be used for compound addition and compound dilution consisted of HBSS buffer with 0.1% glucose.

Cells Buffer

Buffer to be used for cells consisted of HBSS buffer with 0.1% glucose and 0.01% CHAPS.

HL60 cells were thawed and resuspended in Cells media. The cells were centrifuged at 1200 rpm for 8 minutes. Media was aspirated and the cells were resuspended in Cells buffer. The cells were counted and resuspended to $1 \times 10^6$ cells/mL.

Assay1:

Compound Dilution and Assay:

Full inhibition controls were dispensed using 100 nL/well of 1 mM DPI in DMSO to column 18 of a 384 well plate. Compounds were dispensed using 100 nL/well. Full activity controls were dispensed using 100 nL/well of 4 uM PMA in DMSO. Oxyburst Green BSA was added to cell solution at 10 ug/mL. Using the Multidrop, 10 uL cell solution was added to the entire assay plate. The assay plate was incubated at room temperature for 100 minutes. Fluorescence reading was taken after 100 minutes at excitation 485 and emission 530 using 505 Dichroic on the Acquest or Analyst.

Assay 2:

Compound Dilution:

Serial dilution (1:3.10 fold serial dilution) of the compounds was performed in 100% DMSO in 96 well plate—Row B-H Column 1-10. Row A, Column 1-10 contained DPI serial dilution. Starting concentration was $10^{-2}$ M (10 mM). Final concentration in assay was $10^{-4}$ M (100 uM). Compounds were diluted 10 fold in compounds buffer by transferring 10 uL/well of compounds sample in DMSO into 90 uL/well of compounds buffer using Tecan Freedom Evo.

For Assay in 96 Well Plate:

12.5 uL of compounds were dispensed into assay plate column 1-10 using Tecan Freedom Evo. Full inhibition controls were dispensed manually at 12.5 uL/well of 500 uM DPI in DMSO to column 11.10% DMSO was dispensed to column 12, at 12.5 uL/well. Cells were dispensed to all wells at density $0.5 \times 10^6$ cells/mL, 50 uL/well, using Multidrop Combi large dispensing head. Cells with compounds were incubated in assay plates for 10-15 minutes at room temperature. 12.5 uL of 120 nM PMA were dispensed to the entire assay plate. Detection reagent, L012, was dispensed as 2.5× solution, 12.5 uL/well, to the entire assay plate. Luminescence reading was taken at 60 min time point using Tecan Infinite 500.

For Assay in 384 Well Plates:

5 uL of compounds were dispensed into assay plate column 1-10 using Tecan Freedom Evo. Full inhibition controls were dispensed at 5 uL/well of 500 uM DPI in DMSO to column 21 and 22.10% DMSO was dispensed to column 23 and 24, at 5 uL/well. Cells were dispensed to all wells at density $0.5 \times 10^6$ cells/mL, 20 uL/well, using Multidrop Combi small dispensing head. Cells with compounds were incubated in assay plates for 10-15 minutes at room temperature. 5 uL of 120 nM PMA were dispensed to the entire assay plate. Detection reagent, L012, was dispensed as 2.5× solution, 20 uL/well, to the entire assay plate. Luminescence reading was taken at 60 min time point using Tecan Infinite 500.

Results

All exemplified compounds except Examples 4, 5, 22, 24-26, 28, 30, 35, 38-40, 60, 71-75, 119-124 and 126 were tested in at least one of the HL60 assays described above. Of the compounds tested, Examples 1, 8, 10, 18, 20, 31-34, 36, 41, 42, 44, 45, 47, 48, 52, 57, 58, 62, 63, 67, 69, 70, 76, 78-80, 84-96, 100, 102-114 and 117 were found to exhibit a pIC50 greater than 4 in at least one of the assays.

Methods of Use

The compounds of the invention are inhibitors of NOX2 and can be useful in the treatment of diseases mediated by NOX2. Examples of such diseases include neurodegenerative diseases such as amyotrophic lateral sclerosis, Parkinson's disease, Alzheimer's disease and Huntington's disease; neuroinflammatory diseases such as multiple sclerosis; cardiovascular diseases such as hypertension, atherosclerosis, cardiac hypertrophy, cardiac fibrosis and stroke; ocular diseases such as diabetic macular edema, diabetic retinopathy, age-related macular degeneration and glaucoma; spinal cord injury; and traumatic brain injury. Accordingly, in another aspect the invention is directed to methods of treating such diseases.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion, intradermal, extraocular and intraocular administration. Intraocular administration includes intravitreal, subretinal, subscleral, intrachoroidal and subconjuctival administration. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.1 mg to 1000 mg.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In one embodiment, the invention relates to the use of the compounds of the invention in the preparation of a medicament for the treatment of diseases mediated by NOX2. Examples of such diseases include neurodegenerative diseases such as amyotrophic lateral sclerosis, Parkinson's disease, Alzheimer's disease and Huntington's disease; neuroinflammatory diseases such as multiple sclerosis; cardiovascular diseases such as hypertension, atherosclerosis, cardiac hypertrophy, cardiac fibrosis and stroke; ocular diseases such as diabetic macular edema, diabetic retinopathy, age-related macular degeneration and glaucoma; spinal cord injury; and traumatic brain injury.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 0.1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

The invention claimed is:

1. A compound of Formula (I) or a pharmaceutically acceptable salt thereof

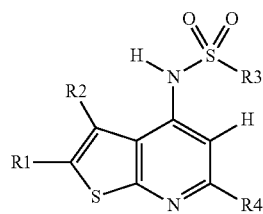

Formula (I)

wherein:
R1 is selected from the group consisting of:
  H, halo, CN, $(CH_2)_n$NRaRa, C(O)NRaRa, C(O)ORb, NRbC(O)Rb, $(CH_2)_m$ORb,
  C1-C6 alkyl optionally substituted with heterocycloalkyl,
  heterocycloalkyl,
  C1-C6 alkynyl optionally substituted with OH, C1-C3 alkoxy, NRaRa or heterocycloalkyl,
  $(CH_2)_n$Rc wherein Rc is optionally substituted with one or more substituents selected from the group consisting of C1-C3 alkoxy, C1-C3 alkyl, NRaRa and halo, and
  $(CH_2)_n$Rd wherein Rd is optionally substituted with one or more substituents selected from the group consisting of C1-C3 alkoxy, C1-C3 alkyl, NRaRa and halo;
R2 is selected from the group consisting of:
  H, halo, CN, C(O)NRaRa,
  C1-C6 alkyl,
  heterocycloalkyl,
  $(CH_2)_n$Rc wherein Rc is optionally substituted with one or more substituents selected from the group consisting of C1-C3 alkoxy, $(CH_2)_n$NRaC(O)ORa, $(CH_2)_n$NRaRa, halo, C1-C4 alkyl optionally substituted with one to three F, and heterocycloalkyl optionally substituted with C(O)ORb, and
  $(CH_2)_n$Rd wherein Rd is optionally substituted with one or more substituents selected from the group consisting of C1-C4 alkyl, C1-C3 alkoxy, halo, heterocycloalkyl and $(CH_2)_n$NRaRa;
R3 is selected from the group consisting of:
  C1-C6 alkyl optionally substituted with Rc wherein Rc is optionally substituted with halo,
  heterocycloalkyl optionally substituted with one or more substituents selected from the group consisting of halo and C(O)ORb wherein Rb is optionally substituted with phenyl,
  cycloalkyl,
  Rc optionally substituted with one or more substituents selected from the group consisting of C1-C3 alkoxy, NRaRa, $NO_2$, halo, and C1-C4 alkyl optionally substituted with one to three F, and
  Rd optionally substituted with one or more substituents selected from the group consisting of C1-C4 alkyl, C1-C3 alkoxy, halo and phenyl;
R4 is H, C1-C6 alkyl, C1-C3 alkoxy, halo, or OH;
each Ra is H or C1-C6 alkyl or both Ra groups, independently in each instance, taken together with the nitrogen atom to which they are attached form a 5 to 7 membered heterocycloalkyl ring;
each Rb is H or C1-C6 alkyl;
each Rc is phenyl;
each Rd is heteroaryl;
each m is 1 or 2; and
each n is 0, 1, 2 or 3.

2. A compound or salt according to claim 1, wherein R1 is C1-C3 alkyl or H.

3. A compound or salt according to claim 1, wherein R1 is pyrazolyl.

4. A compound or salt according to claim 1, wherein R2 is phenyl substituted with one or more substituents selected from the group consisting of dimethylamino, F, pyrrolidinyl and morpholinyl.

5. A compound or salt according to claim 1, wherein R2 is pyridinyl substituted with dimethylamino, pyrrolidinyl or morpholinyl.

6. A compound or salt according to claim 1, wherein R3 is phenyl optionally substituted with one or more Cl or C1-C3 alkoxy.

7. A compound or salt according to claim 1, wherein R3 is heteroaryl optionally substituted with C1-C4 alkyl.

8. A compound or salt according to claim 1, wherein R4 is methyl or H.

9. A compound of Formula (I) or a salt thereof according to claim 1, wherein the compound is selected from:
  3-Chloro-N-{6-methyl-2-(1H-pyrazol-4-yl)-3-[3-(1-pyrrolidinyl)phenyl]thieno[2,3-b]pyridin-4-yl}benzenesulfonamide (E105);
  3-Chloro-N-{6-methyl-2-(1H-pyrazol-4-yl)-3-[5-(1-pyrrolidinyl)-3-pyridinyl]thieno[2,3-b]pyridin-4-yl}benzenesulfonamide (E108);
  3-Chloro-N-{6-methyl-3-[3-(1-pyrrolidinyl)phenyl]thieno[2,3-b]pyridin-4-yl}benzenesulfonamide (E112);
  N-{6-Methyl-2-(1H-pyrazol-4-yl)-3-[5-(1-pyrrolidinyl)-3-pyridinyl]thieno[2,3-b]pyridin-4-yl}benzenesulfonamide (E113); and
  N-{6-Methyl-2-(1H-pyrazol-4-yl)-3-[3-(1-pyrrolidinyl)phenyl]thieno[2,3-b]pyridin-4-yl}benzenesulfonamide (E114).

10. A pharmaceutical composition which comprises a compound according to claim 1 or a pharmaceutically acceptable salt thereof and a pharmaceutically acceptable carrier or excipient.

* * * * *